(12) United States Patent
Tarabrin et al.

(10) Patent No.: US 10,599,048 B2
(45) Date of Patent: Mar. 24, 2020

(54) METROLOGY APPARATUS, METHOD OF MEASURING A STRUCTURE, DEVICE MANUFACTURING METHOD

(71) Applicant: ASML Netherlands B.V., Veldhoven (NL)

(72) Inventors: Sergey Tarabrin, Eindhoven (NL); Armand Eugene Albert Koolen, Nuth (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 16/169,514

(22) Filed: Oct. 24, 2018

(65) Prior Publication Data

US 2019/0129315 A1 May 2, 2019

(30) Foreign Application Priority Data

Oct. 31, 2017 (EP) .................................... 17199439
Feb. 19, 2018 (EP) .................................... 18157411

(51) Int. Cl.
*G01J 3/18* (2006.01)
*G03F 7/20* (2006.01)
(Continued)

(52) U.S. Cl.
CPC ............ *G03F 7/70633* (2013.01); *G01J 3/18* (2013.01); *G01N 21/8806* (2013.01);
(Continued)

(58) Field of Classification Search
CPC ........... G01N 21/9501; G01N 21/8806; G01N 21/956; G01N 21/47; G01N 2021/95676;
(Continued)

(56) References Cited

U.S. PATENT DOCUMENTS 6,642,531 B1  11/2003 Powers
6,952,253 B2  10/2005 Lof et al.
(Continued)

FOREIGN PATENT DOCUMENTS

CN  101104173 A  1/2008
CN  105964626 A  9/2016
(Continued)

OTHER PUBLICATIONS

International Search Report and Written Opinion of the International Searching Authority directed to related International Patent Application No. PCT/EP2018/077598, dated Mar. 21, 2019; 12 pages.
(Continued)

*Primary Examiner* — Michael P Stafira
(74) *Attorney, Agent, or Firm* — Sterne, Kessler, Goldstein & Fox P.L.L.C.

(57) ABSTRACT

Metrology apparatus and methods are disclosed for measuring a structure formed on a substrate. In one arrangement, different components of a radiation beam are selectively extracted after reflection from the structure and independently detected. For each component, radiation is selected from one of a plurality of predetermined regions in a downstream pupil plane of the optical system downstream from the structure. Radiation is further selected from one of two predetermined orthogonal polarization states. The predetermined orthogonal polarization states are oriented differently as a pair for each of at least a subset of components comprising radiation selected from different predetermined regions in the downstream pupil plane.

15 Claims, 20 Drawing Sheets

(51) Int. Cl.
*G03F 9/00* (2006.01)
*G01N 21/88* (2006.01)

(52) U.S. Cl.
CPC ........ *G03F 7/7065* (2013.01); *G03F 7/70191* (2013.01); *G03F 7/70566* (2013.01); *G03F 7/70616* (2013.01); *G03F 7/70625* (2013.01); *G03F 7/70641* (2013.01); *G03F 9/7023* (2013.01)

(58) Field of Classification Search
CPC ......... G01N 21/4788; G01N 21/95607; G01N 2201/06113; G01N 2201/062; G01N 2201/12; G01N 21/93; G01N 2201/10; G01N 2201/1296; G01N 2021/8822; G01N 21/255; G01N 21/88; G01N 21/8851; G01N 21/95623; G01N 2201/061; G01N 2201/0638; G01N 2201/068; G01N 2201/08; G01N 2021/8848; G01N 21/21; G01N 21/211; G01N 21/94; G01N 21/9515; G01N 2201/0683; G01B 11/272; G01B 2210/56; G01B 11/24; G01B 11/0616; G01B 11/14; G01B 11/26; G01B 11/02; G01B 11/0625; G01B 11/30; G01B 2290/70; G01B 9/02042; G01B 9/02081; G01B 9/02083; G01J 3/18; G01J 1/4257; G01J 2003/283; G01J 3/447; G02B 21/242; G02B 26/004; G02B 27/0068; G02B 3/14; G02B 6/0008; G02B 6/10; G02B 21/0016; G02B 21/082; G02B 21/10; G02B 21/14; G02B 21/365; G02B 26/0833; G02B 27/0075; G02B 27/286; G02B 27/58

See application file for complete search history.

(56) References Cited

U.S. PATENT DOCUMENTS

| | | |
|---|---|---|
| 2003/0011763 A1 | 1/2003 | Taniguchi et al. |
| 2004/0218157 A1 | 11/2004 | Bakker et al. |
| 2006/0033921 A1 | 2/2006 | Den Boef et al. |
| 2006/0066855 A1 | 3/2006 | Boef et al. |
| 2007/0091287 A1 | 4/2007 | Chang et al. |
| 2007/0256258 A1 | 11/2007 | Takayanagi |
| 2010/0078846 A1 | 4/2010 | Resnick et al. |
| 2010/0201963 A1 | 8/2010 | Cramer et al. |
| 2010/0328655 A1 | 12/2010 | Den Boef |
| 2011/0026032 A1 | 2/2011 | Den Boef et al. |
| 2011/0027704 A1 | 2/2011 | Cramer et al. |
| 2011/0037960 A1 | 2/2011 | Scaccabarozzi et al. |
| 2011/0043791 A1 | 2/2011 | Smilde et al. |
| 2011/0102753 A1 | 5/2011 | Van De Kerkhof et al. |
| 2011/0249244 A1 | 10/2011 | Leewis et al. |
| 2011/0310388 A1* | 12/2011 | Hill ...................... G01N 21/474 356/369 |
| 2012/0044470 A1 | 2/2012 | Smilde et al. |
| 2012/0242970 A1 | 9/2012 | Smilde et al. |
| 2013/0141730 A1* | 6/2013 | Quintanilha ............. G02B 6/10 356/446 |
| 2013/0235357 A1 | 9/2013 | Delgado et al. |
| 2014/0354983 A1* | 12/2014 | Kolchin ............... H05K 999/99 356/237.5 |
| 2014/0361152 A1 | 12/2014 | Maleev et al. |
| 2015/0279609 A1 | 10/2015 | Tanii et al. |
| 2016/0313654 A1* | 10/2016 | Zeng ................... G03F 7/70633 |
| 2016/0370717 A1* | 12/2016 | Den Boef ........... G03F 7/70633 |
| 2017/0102620 A1* | 4/2017 | Zijp .................... G03F 7/70133 |
| 2017/0255112 A1 | 9/2017 | Van Leest et al. |
| 2019/0201943 A1 | 7/2019 | Maas et al. |

FOREIGN PATENT DOCUMENTS

| | | |
|---|---|---|
| EP | 1 329 773 A2 | 7/2003 |
| EP | 1 628 164 A2 | 2/2006 |
| EP | 2 365 347 A1 | 9/2011 |
| WO | WO 2009/078708 A1 | 6/2009 |
| WO | WO 2009/106279 A1 | 9/2009 |
| WO | WO 2009/129960 A1 | 10/2009 |
| WO | WO 2015/143378 A1 | 9/2015 |

OTHER PUBLICATIONS

International Search Report directed to related International Patent Application No. PCT/EP2018/082964, dated Jan. 8, 2019; 5 pages.
Li Lifeng, "Symmetries of cross-polarization diffraction coefficients of gratings," Journal of the Optical Society of America A, vol. 17, No. 5, May 2000; pp. 881-887.
International Search Report and Written Opinion of the International Searching Authority directed to related International Patent Application No. PCT/EP2018/082964, dated Jan. 8, 2019; 9 pages.
Office Action directed to related Taiwanese Patent Application No. 107145861, dated Nov. 14, 2019, with attached English-language translation; 20 pages.

* cited by examiner

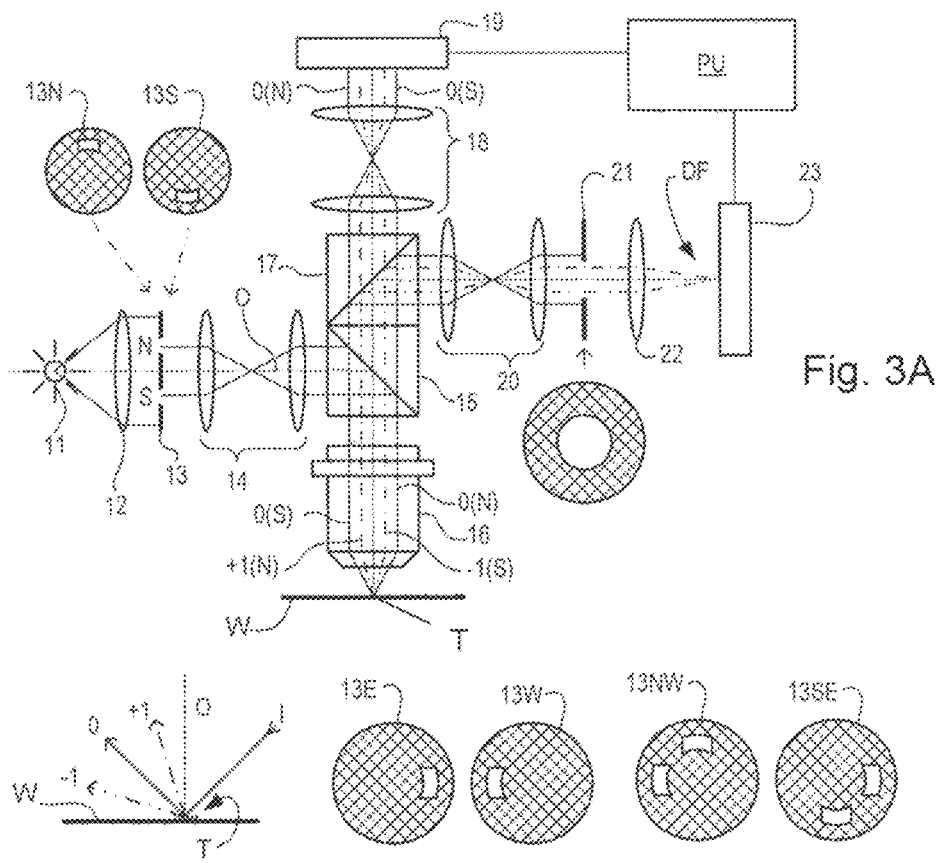
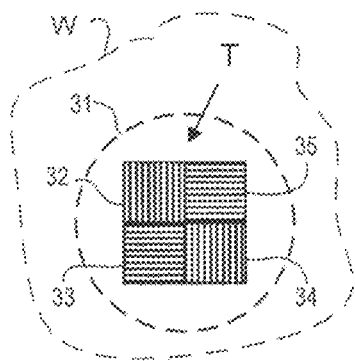
Fig. 4
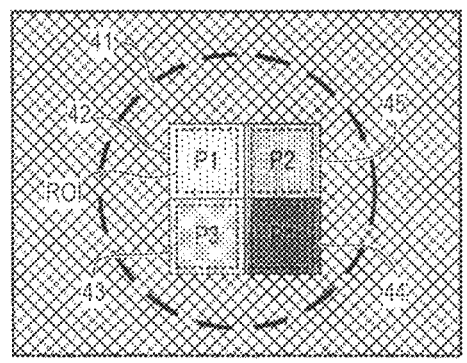
Fig. 5

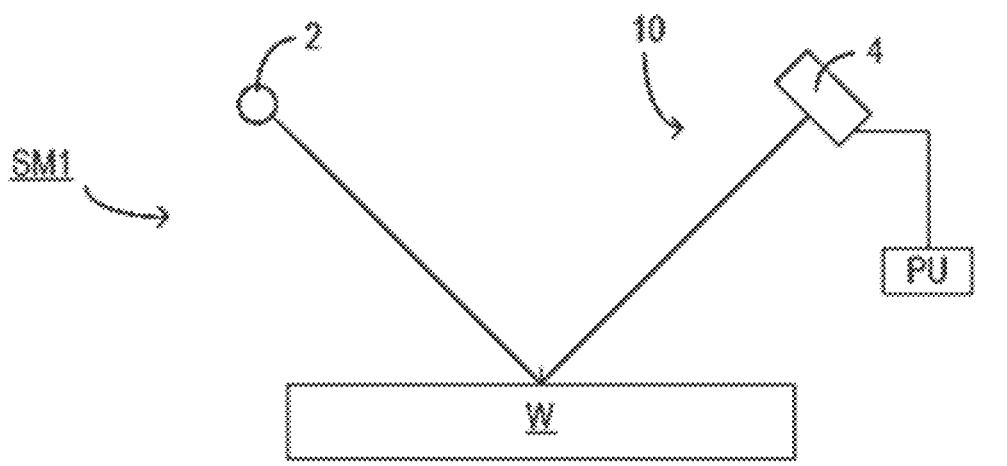
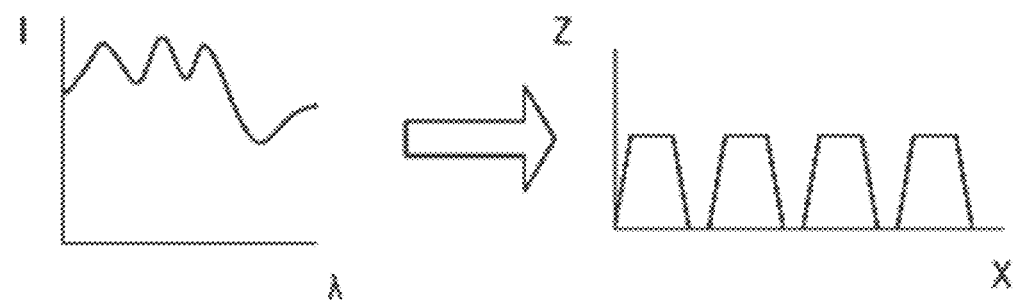
Fig.6

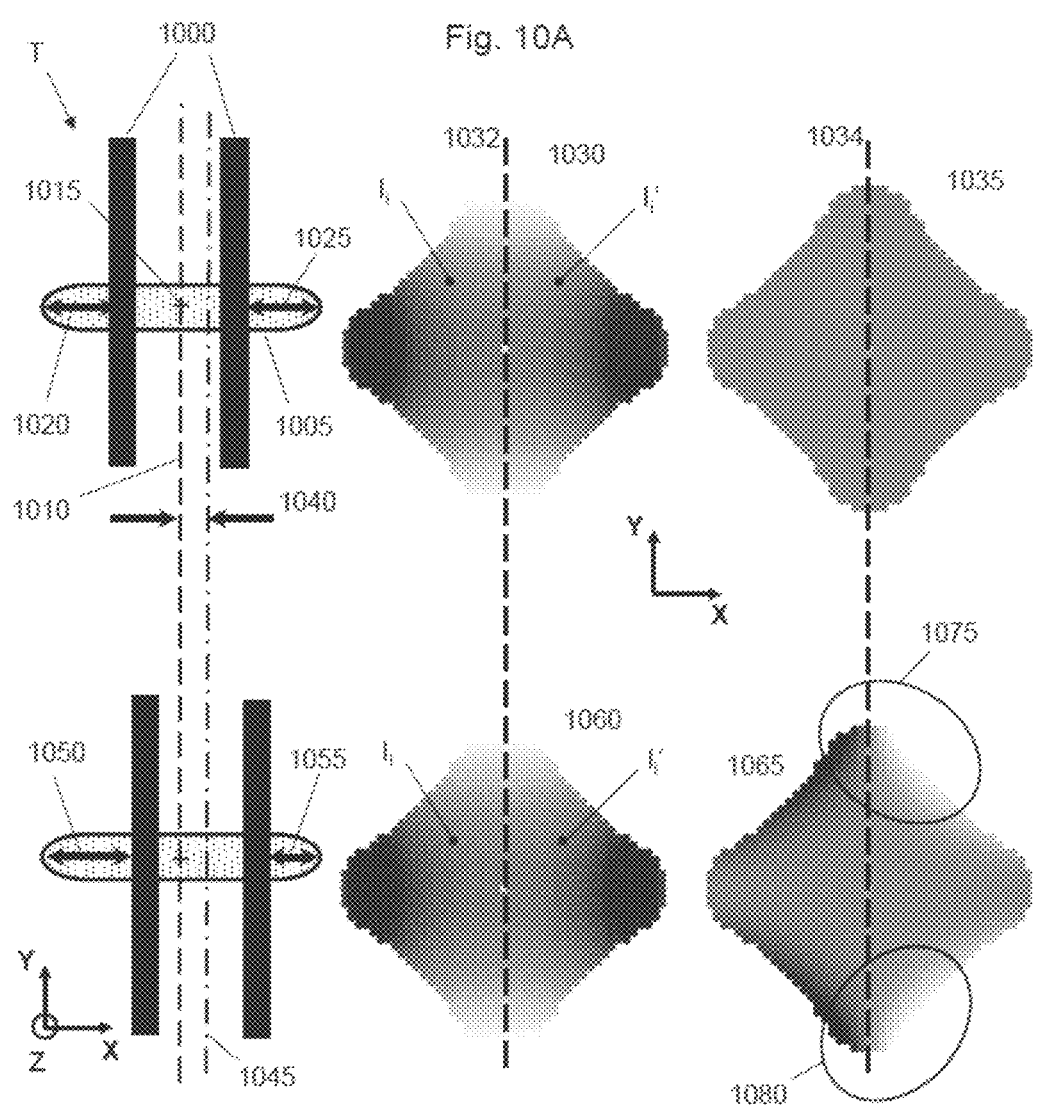

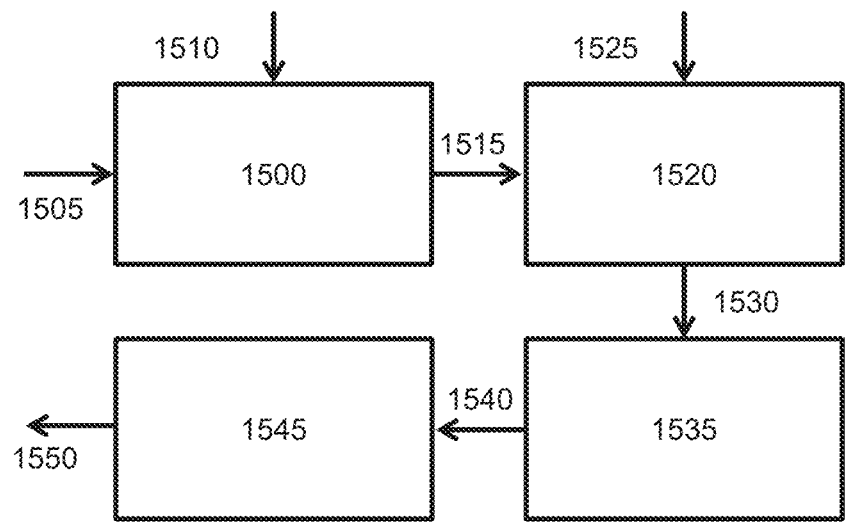
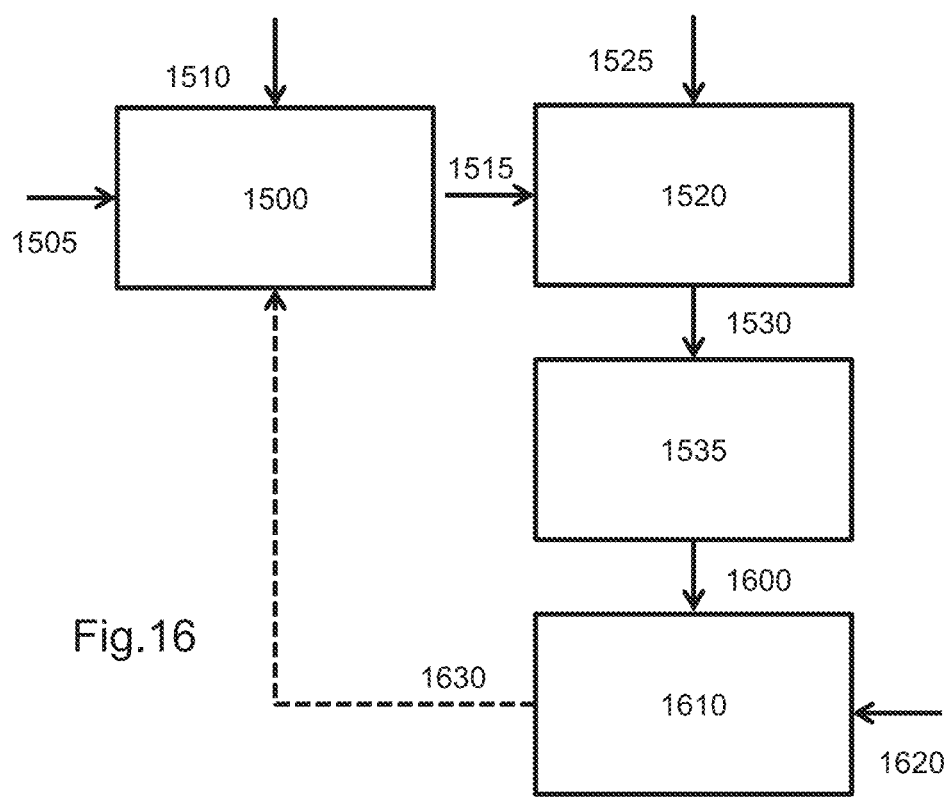
Fig.15
Fig.16

METROLOGY APPARATUS, METHOD OF MEASURING A STRUCTURE, DEVICE MANUFACTURING METHOD

FIELD

The present description relates to a metrology apparatus for measuring a structure formed on a substrate, a method of measuring a structure formed on a substrate, and a device manufacturing method.

BACKGROUND

A lithographic apparatus is a machine that applies a desired pattern onto a substrate, usually onto a target portion of the substrate. A lithographic apparatus can be used, for example, in the manufacture of integrated circuits (ICs) or other devices designed to be functional. In that instance, a patterning device, which is alternatively referred to as a mask or a reticle, may be used to generate a circuit pattern to be formed on an individual layer of the device designed to be functional. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

Manufacturing devices, such as semiconductor devices, typically involves processing a substrate (e.g., a semiconductor wafer) using a number of fabrication processes to form various features and often multiple layers of the devices. Such layers and/or features are typically manufactured and processed using, e.g., deposition, lithography, etch, chemical-mechanical polishing, and ion implantation. Multiple devices may be fabricated on a plurality of dies on a substrate and then separated into individual devices. This device manufacturing process may be considered a patterning process. A patterning process involves a pattern transfer step, such as optical and/or nanoimprint lithography using a lithographic apparatus, to provide a pattern on a substrate and typically, but optionally, involves one or more related pattern processing steps, such as resist development by a development apparatus, baking of the substrate using a bake tool, etching the pattern by an etch apparatus, etc. Further, one or more metrology processes are involved in the patterning process.

Metrology processes are used at various steps during a patterning process to monitor and/or control the process. For example, metrology processes are used to measure one or more characteristics of a substrate, such as a relative location (e.g., registration, overlay, alignment, etc.) or dimension (e.g., line width, critical dimension (CD), thickness, etc.) of features formed on the substrate during the patterning process, such that, for example, the performance of the patterning process can be determined from the one or more characteristics. If the one or more characteristics are unacceptable (e.g., out of a predetermined range for the characteristic(s)), one or more variables of the patterning process may be designed or altered, e.g., based on the measurements of the one or more characteristics, such that substrates manufactured by the patterning process have an acceptable characteristic(s).

With the advancement of lithography and other patterning process technologies, the dimensions of functional elements have continually been reduced while the amount of the functional elements, such as transistors, per device has been steadily increased over decades. In the meanwhile, the requirement of accuracy in terms of overlay, critical dimension (CD), etc. has become more and more stringent. Error, such as error in overlay, error in CD, etc., will inevitably be produced in the patterning process. For example, imaging error may be produced from optical aberration, patterning device heating, patterning device error, and/or substrate heating and can be characterized in terms of, e.g., overlay, CD, etc. Additionally or alternatively, error may be introduced in other parts of the patterning process, such as in etch, development, bake, etc. and similarly can be characterized in terms of, e.g., overlay, CD, etc. The error may cause a problem in terms of the functioning of the device, including failure of the device to function or one or more electrical problems of the functioning device. Accordingly, it is desirable to be able to characterize one or more these errors and take steps to design, modify, control, etc. a patterning process to reduce or minimize one or more of these errors.

SUMMARY

According to an aspect, there is provided a metrology apparatus for measuring a structure formed on a substrate, comprising: an optical system configured to focus radiation onto the structure and direct radiation after reflection from the structure onto a detection system; and a beam processing device configured to selectively extract a plurality of different components of the radiation beam after reflection from the structure, and to direct each of the extracted components to the detection system such that each component can be detected independently of each other component, wherein: the selective extraction comprises, for each component: 1) selecting radiation from one of a plurality of predetermined regions in a downstream pupil plane of the optical system downstream from the structure, the selected predetermined region being different for each of at least a subset of the components; and 2) selecting radiation from one of two predetermined orthogonal polarization states, the predetermined orthogonal polarization states being oriented differently as a pair for each of at least a subset of the components comprising radiation selected from different predetermined regions in the downstream pupil plane.

According to an aspect, there is provided a method of measuring a structure formed on a substrate, comprising: focusing radiation onto the structure and directing radiation after reflection from the structure onto a detection system; and selectively extracting a plurality of different components of the radiation beam after reflection from the structure, and detecting each of the extracted components independently of each other component using the detection system, wherein: the selective extraction comprises, for each component: 1) selecting radiation from one of a plurality of predetermined regions in a downstream pupil plane of the optical system downstream from the structure, the selected predetermined region being different for each of at least a subset of the components; and 2) selecting radiation from one of two predetermined orthogonal polarization states, the predetermined orthogonal polarization states being oriented differently as a pair for each of at least a subset of the components comprising radiation selected from different predetermined regions in the downstream pupil plane.

According to an aspect, there is provided a device manufacturing method, comprising: using a patterning process to form a structure on a substrate; focusing radiation onto the structure and directing radiation after reflection from the structure onto a detection system; and selectively extracting a plurality of different components of the radiation beam after reflection from the structure, and detecting each of the extracted components independently of each other component using the detection system, wherein: the selective extraction comprises, for each component: 1) selecting radiation from one of a plurality of predetermined regions in a downstream pupil plane of the optical system downstream from the structure, the selected predetermined region being different for each of at least a subset of the components; and 2) selecting radiation from one of two predetermined orthogonal polarization states, the predetermined orthogonal polarization states being oriented differently as a pair for each of at least a subset of the components comprising radiation selected from different predetermined regions in the downstream pupil plane.

BRIEF DESCRIPTION OF THE DRAWINGS

Embodiments will now be described, by way of example only, with reference to the accompanying drawings in which:

FIG. 3A is schematic diagram of a measurement apparatus for use in measuring targets according to an embodiment using a first pair of illumination apertures providing certain illumination modes;

FIG. 3B is a schematic detail of a diffraction spectrum of a target for a given direction of illumination;

FIG. 3C is a schematic illustration of a second pair of illumination apertures providing further illumination modes in using a measurement apparatus for diffraction based overlay measurements;

FIG. 3D is a schematic illustration of a third pair of illumination apertures combining the first and second pairs of apertures providing further illumination modes in using a measurement apparatus for diffraction based overlay measurements;

FIG. 4 schematically depicts a form of multiple periodic structure (e.g., multiple grating) target and an outline of a measurement spot on a substrate;

FIG. 5 schematically depicts an image of the target of FIG. 4 obtained in the apparatus of FIG. 3;

FIG. 6 schematically depicts an example metrology apparatus and metrology technique;

FIG. 10A schematically depicts an example unit cell, an associated pupil representation, and an associated derived pupil representation;

FIG. 10B schematically depicts an example unit cell, an associated pupil representation, and an associated derived pupil representation;

FIG. 15 depicts a high-level flow of an embodiment of a data driven technique in combination with a physical geometric model;

FIG. 16 depicts a high-level flow of an embodiment of a data driven technique in combination with a physical geometric model;

DETAILED DESCRIPTION

Before describing embodiments in detail, it is instructive to present an example environment in which embodiments may be implemented.

Figure 1:
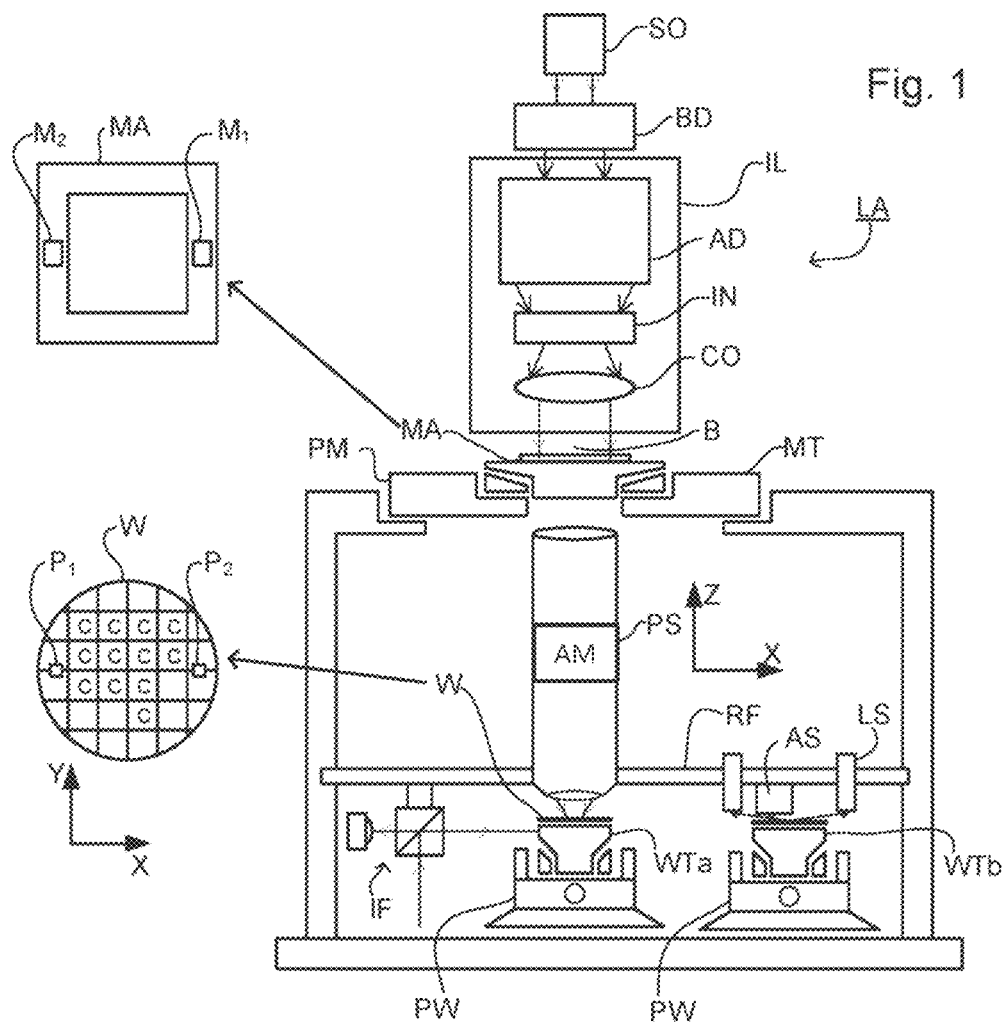
FIG. 1 schematically depicts an embodiment of a lithographic apparatus.

FIG. 1 schematically depicts a lithographic apparatus LA. The apparatus comprises:
  an illumination system (illuminator) IL configured to condition a radiation beam B (e.g. UV radiation or DUV radiation);

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W, the projection system supported on a reference frame (RF).

The illumination system may include various types of optical components, such as refractive, reflective, magnetic, electromagnetic, electrostatic or other types of optical components, or any combination thereof, for directing, shaping, or controlling radiation.

The support structure supports the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a pattern in a target portion of the substrate. In an embodiment, a patterning device is any device that can be used to impart a radiation beam with a pattern in its cross-section so as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The projection system PS has an optical transfer function which may be non-uniform, which can affect the pattern imaged on the substrate W. For unpolarized radiation such effects can be fairly well described by two scalar maps, which describe the transmission (apodization) and relative phase (aberration) of radiation exiting the projection system PS as a function of position in a pupil plane thereof. These scalar maps, which may be referred to as the transmission map and the relative phase map, may be expressed as a linear combination of a complete set of basis functions. A particularly convenient set is the Zernike polynomials, which form a set of orthogonal polynomials defined on a unit circle. A determination of each scalar map may involve determining the coefficients in such an expansion. Since the Zernike polynomials are orthogonal on the unit circle, the Zernike coefficients may be determined by calculating the inner product of a measured scalar map with each Zernike polynomial in turn and dividing this by the square of the norm of that Zernike polynomial.

The transmission map and the relative phase map are field and system dependent. That is, in general, each projection system PS will have a different Zernike expansion for each field point (i.e. for each spatial location in its image plane). The relative phase of the projection system PS in its pupil plane may be determined by projecting radiation, for example from a point-like source in an object plane of the projection system PS (i.e. the plane of the patterning device MA), through the projection system PS and using a shearing interferometer to measure a wavefront (i.e. a locus of points with the same phase). A shearing interferometer is a common path interferometer and therefore, advantageously, no secondary reference beam is required to measure the wavefront. The shearing interferometer may comprise a diffraction grating, for example a two dimensional grid, in an image plane of the projection system (i.e. the substrate table WT) and a detector arranged to detect an interference pattern in a plane that is conjugate to a pupil plane of the projection system PS. The interference pattern is related to the derivative of the phase of the radiation with respect to a coordinate in the pupil plane in the shearing direction. The detector may comprise an array of sensing elements such as, for example, charge coupled devices (CCDs).

The projection system PS of a lithography apparatus may not produce visible fringes and therefore the accuracy of the determination of the wavefront can be enhanced using phase stepping techniques such as, for example, moving the diffraction grating. Stepping may be performed in the plane of the diffraction grating and in a direction perpendicular to the scanning direction of the measurement. The stepping range may be one grating period, and at least three (uniformly distributed) phase steps may be used. Thus, for example, three scanning measurements may be performed in the y-direction, each scanning measurement being performed for a different position in the x-direction. This stepping of the diffraction grating effectively transforms phase variations into intensity variations, allowing phase information to be determined. The grating may be stepped in a direction perpendicular to the diffraction grating (z direction) to calibrate the detector.

The transmission (apodization) of the projection system PS in its pupil plane may be determined by projecting radiation, for example from a point-like source in an object plane of the projection system PS (i.e. the plane of the patterning device MA), through the projection system PS and measuring the intensity of radiation in a plane that is conjugate to a pupil plane of the projection system PS, using a detector. The same detector as is used to measure the wavefront to determine aberrations may be used.

The projection system PS may comprise a plurality of optical (e.g., lens) elements and may further comprise an adjustment mechanism AM configured to adjust one or more of the optical elements so as to correct for aberrations (phase variations across the pupil plane throughout the field). To achieve this, the adjustment mechanism may be operable to manipulate one or more optical (e.g., lens) elements within the projection system PS in one or more different ways. The projection system may have a co-ordinate system wherein its optical axis extends in the z direction. The adjustment mechanism may be operable to do any combination of the following: displace one or more optical elements; tilt one or more optical elements; and/or deform one or more optical elements. Displacement of an optical element may be in any direction (x, y, z or a combination thereof). Tilting of an optical element is typically out of a plane perpendicular to the optical axis, by rotating about an axis in the x and/or y directions although a rotation about the z axis may be used for a non-rotationally symmetric aspherical optical element. Deformation of an optical element may include a low frequency shape (e.g. astigmatic) and/or a high frequency shape (e.g. free form aspheres). Deformation of an optical element may be performed for example by using one or more actuators to exert force on one or more sides of the optical element and/or by using one or more heating elements to heat one or more selected regions of the optical element. In general, it may not be possible to adjust the projection system PS to correct for apodization (transmission variation across the pupil plane). The transmission map of a projection system PS may be used when designing a patterning device (e.g., mask) MA for the lithography apparatus LA. Using a computational lithography technique, the patterning device MA may be designed to at least partially correct for apodization.

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more tables (e.g., two or more substrate tables WTa, WTb, two or more patterning device tables, a substrate table WTa and a table WTb below the projection system without a substrate that is dedicated to, for example, facilitating measurement, and/or cleaning, etc.). In such "multiple stage" machines the additional tables may be used in parallel, or preparatory steps may be carried out on one or more tables while one or more other tables are being used for exposure. For example, alignment measurements using an alignment sensor AS and/or level (height, tilt, etc.) measurements using a level sensor LS may be made.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-) magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
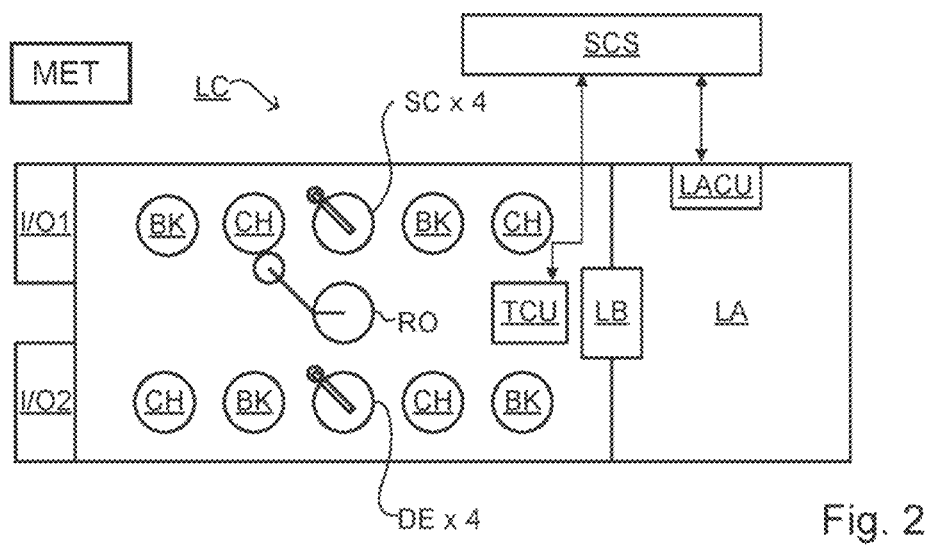
FIG. 2 schematically depicts an embodiment of a lithographic cell or cluster.

As shown in FIG. 2, the lithographic apparatus LA may form part of a lithographic cell LC, also sometimes referred to a lithocell or cluster, which also includes apparatuses to perform pre- and post-exposure processes on a substrate. Conventionally these include one or more spin coaters SC to deposit one or more resist layers, one or more developers DE to develop exposed resist, one or more chill plates CH and/or one or more bake plates BK. A substrate handler, or robot, RO picks up one or more substrates from input/output port I/O1, I/O2, moves them between the different process apparatuses and delivers them to the loading bay LB of the lithographic apparatus. These apparatuses, which are often collectively referred to as the track, are under the control of a track control unit TCU which is itself controlled by the supervisory control system SCS, which also controls the lithographic apparatus via lithography control unit LACU. Thus, the different apparatuses can be operated to maximize throughput and processing efficiency.

In order that a substrate that is exposed by the lithographic apparatus is exposed correctly and consistently, it is desirable to inspect an exposed substrate to measure or determine one or more properties such as overlay (which can be, for example, between structures in overlying layers or between structures in a same layer that have been provided separately to the layer by, for example, a double patterning process), line thickness, critical dimension (CD), focus offset, a material property, etc. Accordingly a manufacturing facility in which lithocell LC is located also typically includes a metrology system MET which receives some or all of the substrates W that have been processed in the lithocell. The metrology system MET may be part of the lithocell LC, for example it may be part of the lithographic apparatus LA.

Metrology results may be provided directly or indirectly to the supervisory control system SCS. If an error is detected, an adjustment may be made to exposure of a subsequent substrate (especially if the inspection can be done soon and fast enough that one or more other substrates of the batch are still to be exposed) and/or to subsequent exposure of the exposed substrate. Also, an already exposed substrate may be stripped and reworked to improve yield, or discarded, thereby avoiding performing further processing on a substrate known to be faulty. In a case where only some target portions of a substrate are faulty, further exposures may be performed only on those target portions which are good.

Within a metrology system MET, a metrology apparatus is used to determine one or more properties of the substrate, and in particular, how one or more properties of different substrates vary or different layers of the same substrate vary from layer to layer. The metrology apparatus may be integrated into the lithographic apparatus LA or the lithocell LC or may be a stand-alone device. To enable rapid measurement, it is desirable that the metrology apparatus measure one or more properties in the exposed resist layer immediately after the exposure. However, the latent image in the resist has a low contrast—there is only a very small difference in refractive index between the parts of the resist which have been exposed to radiation and those which have not—and not all metrology apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of a faulty substrate but may still provide useful information.

To enable the metrology, one or more targets can be provided on the substrate. In an embodiment, the target is specially designed and may comprise a periodic structure. In an embodiment, the target is a part of a device pattern, e.g., a periodic structure of the device pattern. In an embodiment, the device pattern is a periodic structure of a memory device (e.g., a Bipolar Transistor (BPT), a Bit Line Contact (BLC), etc. structure).

In an embodiment, the target on a substrate may comprise one or more 1-D periodic structures (e.g., gratings), which are printed such that after development, the periodic structural features are formed of solid resist lines. In an embodiment, the target may comprise one or more 2-D periodic structures (e.g., gratings), which are printed such that after development, the one or more periodic structures are formed of solid resist pillars or vias in the resist. The bars, pillars or vias may alternatively be etched into the substrate (e.g., into one or more layers on the substrate).

In an embodiment, one of the parameters of interest of a patterning process is overlay. Overlay can be measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated in their entirety by reference. Further developments of the technique have been described in U.S. patent application publications US2011-0027704, US2011-0043791 and US2012-0242970, which are hereby incorporated in their entirety by reference. Diffraction-based overlay using dark-field detection of the diffraction orders enables overlay measurements on smaller targets. These targets can be smaller than the illumination spot and may be surrounded by device product structures on a substrate. In an embodiment, multiple targets can be measured in one radiation capture.

A metrology apparatus suitable for use in embodiments to measure, e.g., overlay is schematically shown in FIG. 3A. A target T (comprising a periodic structure such as a grating) and diffracted rays are illustrated in more detail in FIG. 3B. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by an output 11 (e.g., a source such as a laser or a xenon lamp or an opening connected to a source) is directed onto substrate W via a prism 15 by an optical system comprising lenses 12, 14 and objective lens 16. These lenses are arranged in a double sequence of a 4F arrangement. A different lens arrangement can be used, provided that it still provides a substrate image onto a detector.

In an embodiment, the lens arrangement allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done, for example, by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis illumination from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode may interfere with the desired measurement signals.

As shown in FIG. 3B, target T is placed with substrate W substantially normal to the optical axis O of objective lens 16. A ray of illumination I impinging on target T from an angle off the axis O gives rise to a zeroth order ray (solid line 0) and two first order rays (dot-chain line +1 and double dot-chain line −1). With an overfilled small target T, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitch and illumination angle can be designed or adjusted so that the first order rays entering the objective lens are closely aligned with the central optical axis. The rays illustrated in FIGS. 3A and 3B are shown somewhat off axis, purely to enable them to be more easily distinguished in the diagram. At least the 0 and +1 orders diffracted by the target on substrate W are collected by objective lens 16 and directed back through prism 15.

Returning to FIG. 3A, both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16. Thus, in an embodiment, measurement results are obtained by measuring the target twice under certain conditions, e.g., after rotating the target or changing the illumination mode or changing the imaging mode to obtain separately the −1st and the +1st diffraction order intensities. Comparing these intensities for a given target provides a measurement of asymmetry in the target, and asymmetry in the target can be used as an indicator of a parameter of a lithography process, e.g., overlay. In the situation described above, the illumination mode is changed.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements. The pupil plane image can also be used for other measurement purposes such as reconstruction, as described further hereafter.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane of the objective lens 16. Aperture stop 21 functions to block the zeroth order diffracted beam so that the image of the target formed on sensor 23 is formed from the −1 or +1 first order beam. Data regarding the images measured by sensors 19 and 23 are output to processor and controller PU, the function of which will depend on the particular type of measurements being performed. Note that the term 'image' is used in a broad sense. An image of the periodic structure features (e.g., grating lines) as such will not be formed, if only one of the −1 and +1 orders is present.

The particular forms of aperture plate 13 and stop 21 shown in FIG. 3 are purely examples. In another embodiment, on-axis illumination of the target is used and an aperture stop with an off-axis aperture is used to pass substantially only one first order of diffracted radiation to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Note that aperture plate 13N or 13S are used to measure a periodic structure of a target oriented in one direction (X or Y depending on the set-up). For measurement of an orthogonal periodic structure, rotation of the target through 90° and 270° might be implemented. Different aperture plates are shown in FIGS. 3C and D. FIG. 3C illustrates two further types of off-axis illumination mode. In a first illumination mode of FIG. 3C, aperture plate 13E provides off-axis illumination from a direction designated, for the sake of description only, as 'east' relative to the 'north' previously described. In a second illumination mode of FIG. 3C, aperture plate 13W is used to provide similar illumination, but from an opposite direction, labeled 'west'. FIG. 3D illustrates two further types of off-axis illumination mode. In a first illumination mode of FIG. 3D, aperture plate 13NW provides off-axis illumination from the directions designated 'north' and 'west' as previously described. In a second illumination mode, aperture plate 13SE is used to provide similar illumination, but from an opposite direction, labeled 'south' and 'east' as previously described. The use of these, and numerous other variations and applications of the apparatus are described in, for example, the prior published patent application publications mentioned above.

FIG. 4 depicts an example composite metrology target T formed on a substrate. The composite target comprises four periodic structures (in this case, gratings) 32, 33, 34, 35 positioned closely together. In an embodiment, the periodic structure layout may be made smaller than the measurement spot (i.e., the periodic structure layout is overfilled). Thus, in an embodiment, the periodic structures are positioned closely together enough so that they all are within a measurement spot 31 formed by the illumination beam of the metrology apparatus. In that case, the four periodic structures thus are all simultaneously illuminated and simultaneously imaged on sensors 19 and 23. In an example dedicated to overlay measurement, periodic structures 32, 33, 34, 35 are themselves composite periodic structures (e.g., composite gratings) formed by overlying periodic structures, i.e., periodic structures are patterned in different layers of the device formed on substrate W and such that at least one periodic structure in one layer overlays at least one periodic structure in a different layer. Such a target may have outer dimensions within 20 μm×20 μm or within 16 μm×16 μm. Further, all the periodic structures are used to measure overlay between a particular pair of layers. To facilitate a target being able to measure more than a single pair of layers, periodic structures 32, 33, 34, 35 may have differently biased overlay offsets in order to facilitate measurement of overlay between different layers in which the different parts of the composite periodic structures are formed. Thus, all the periodic structures for the target on the substrate would be used to measure one pair of layers and all the periodic structures for another same target on the substrate would be used to measure another pair of layers, wherein the different bias facilitates distinguishing between the layer pairs.

Returning to FIG. 4, periodic structures 32, 33, 34, 35 may also differ in their orientation, as shown, so as to diffract incoming radiation in X and Y directions. In one example, periodic structures 32 and 34 are X-direction periodic structures with biases of +d, −d, respectively. Periodic structures 33 and 35 may be Y-direction periodic structures with offsets +d and −d respectively. While four periodic structures are illustrated, another embodiment may include a larger matrix to obtain desired accuracy. For example, a 3×3 array of nine composite periodic structures may have biases −4d, −3d, −2d, −d, 0, +d, +2d, +3d, +4d. Separate images of these periodic structures can be identified in an image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3D. While the sensor 19 cannot resolve the different individual periodic structures 32 to 35, the sensor 23 can do so. The dark rectangle represents the field of the image on the sensor, within which the illuminated spot 31 on the substrate is imaged into a corresponding circular area 41. Within this, rectangular areas 42-45 represent the images of the periodic structures 32 to 35. The target can be positioned in among device product features, rather than or in addition to in a scribe lane. If the periodic structures are located in device product areas, device features may also be visible in the periphery of this image field. Processor and controller PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an example of such a parameter.

In an embodiment, one of the parameters of interest of a patterning process is feature width (e.g., CD). FIG. 6 depicts a highly schematic example metrology apparatus (e.g., a scatterometer) that can enable feature width determination. It comprises a broadband (white light) radiation projector 2 which projects radiation onto a substrate W. The redirected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 6. In general, for the reconstruction the general form of the structure is known and some variables are assumed from knowledge of the process by which the structure was made, leaving only a few variables of the structure to be determined from the measured data. Such a metrology apparatus may be configured as a normal-incidence metrology apparatus or an oblique-incidence metrology apparatus. Moreover, in addition to measurement of a parameter by reconstruction, angle resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement in this manner are described, for example, in U.S. patent application publication US2006-066855, which is incorporated herein in its entirety.

Figure 7:
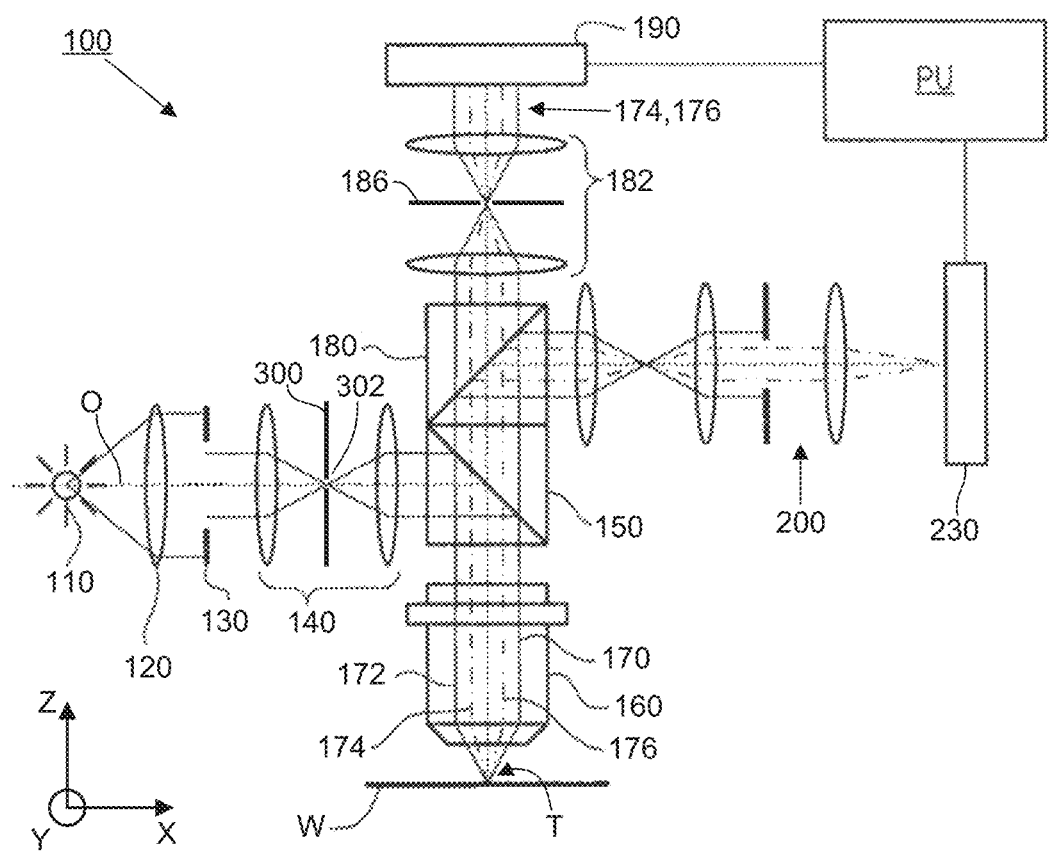
FIG. 7 schematically depicts an example metrology apparatus.

FIG. 7 illustrates an example of a metrology apparatus 100 suitable for use in embodiments of the invention disclosed herein. The principles of operation of this type of metrology apparatus are explained in more detail in the U.S. Patent Application Nos. US 2006-033921 and US 2010-201963, which are incorporated herein in their entireties by reference. An optical axis, which has several branches throughout the apparatus, is represented by a dotted line O. In this apparatus, radiation emitted by source 110 (e.g., a xenon lamp) is directed onto substrate W via by an optical system comprising: lens system 120, aperture plate 130, lens system 140, a partially reflecting surface 150 and objective lens 160. In an embodiment these lens systems 120, 140, 160 are arranged in a double sequence of a 4F arrangement. In an embodiment, the radiation emitted by radiation source 110 is collimated using lens system 120. A different lens arrangement can be used, if desired. The angular range at which the radiation is incident on the substrate can be selected by defining a spatial intensity distribution in a plane that presents the spatial spectrum of the substrate plane. In particular, this can be done by inserting an aperture plate 130 of suitable form between lenses 120 and 140, in a plane which is a back-projected image of the objective lens pupil plane. Different intensity distributions (e.g., annular, dipole, etc.) are possible by using different apertures. The angular distribution of illumination in radial and peripheral directions, as well as properties such as wavelength, polarization and/or coherency of the radiation, can all be adjusted to obtain desired results. For example, one or more interference filters 130 (see FIG. 9) can be provided between source 110 and partially reflecting surface 150 to select a wavelength of interest in the range of, say, 400-900 nm or even lower, such as 200-300 nm. The interference filter may be tunable rather than comprising a set of different filters. A grating could be used instead of an interference filter. In an embodiment, one or more polarizers 170 (see FIG. 9) can be provided between source 110 and partially reflecting surface 150 to select a polarization of interest. The polarizer may be tunable rather than comprising a set of different polarizers.

As shown in FIG. 7, the target T is placed with substrate W normal to the optical axis O of objective lens 160. Thus, radiation from source 110 is reflected by partially reflecting surface 150 and focused into an illumination spot S (see FIG. 8) on target T on substrate W via objective lens 160. In an embodiment, objective lens 160 has a high numerical aperture (NA), desirably at least 0.9 or at least 0.95. An immersion metrology apparatus (using a relatively high refractive index fluid such as water) may even have a numerical aperture over 1.

Rays of illumination 170, 172 focused to the illumination spot from angles off the axis O gives rise to diffracted rays 174, 176. It should be remembered that these rays are just one of many parallel rays covering an area of the substrate including target T. Each element within the illumination spot is within the field of view of the metrology apparatus. Since the aperture in plate 130 has a finite width (necessary to admit a useful quantity of radiation), the incident rays 170, 172 will in fact occupy a range of angles, and the diffracted rays 174, 176 will be spread out somewhat. According to the point spread function of a small target, each diffraction order will be further spread over a range of angles, not a single ideal ray as shown.

At least the $0^{th}$ order diffracted by the target on substrate W is collected by objective lens 160 and directed back through partially reflecting surface 150. An optical element 180 provides at least part of the diffracted beams to optical system 182 which forms a diffraction spectrum (pupil plane image) of the target T on sensor 190 (e.g. a CCD or CMOS sensor) using the zeroth and/or first order diffractive beams. In an embodiment, an aperture 186 is provided to filter out certain diffraction orders so that a particular diffraction order is provided to the sensor 190. In an embodiment, the aperture 186 allows substantially or primarily only zeroth order radiation to reach the sensor 190. In an embodiment, the sensor 190 may be a two-dimensional detector so that a two-dimensional angular scatter spectrum of a substrate target T can be measured. The sensor 190 may be, for example, an array of CCD or CMOS sensors, and may use an integration time of, for example, 40 milliseconds per frame. The sensor 190 may be used to measure the intensity of redirected radiation at a single wavelength (or narrow wavelength range), the intensity separately at multiple wavelengths or integrated over a wavelength range. Furthermore, the sensor may be used to separately measure the intensity of radiation with transverse magnetic- and/or transverse electric-polarization and/or the phase difference between transverse magnetic- and transverse electric-polarized radiation.

Optionally, optical element 180 provides at least part of the diffracted beams to measurement branch 200 to form an image of the target on the substrate W on a sensor 230 (e.g. a CCD or CMOS sensor). The measurement branch 200 can be used for various auxiliary functions such as focusing the metrology apparatus (i.e., enabling the substrate W to be in focus with the objective 160), and/or for dark field imaging of the type mentioned in the introduction.

In order to provide a customized field of view for different sizes and shapes of grating, an adjustable field stop 300 is provided within the lens system 140 on the path from source 110 to the objective lens 160. The field stop 300 contains an aperture 302 and is located in a plane conjugate with the plane of the target T, so that the illumination spot becomes an image of the aperture 302. The image may be scaled according to a magnification factor, or the aperture and illumination spot may be in 1:1 size relation. In order to make the illumination adaptable to different types of measurement, the aperture plate 300 may comprise a number of aperture patterns formed around a disc, which rotates to bring a desired pattern into place. Alternatively or in addition, a set of plates 300 could be provided and swapped, to achieve the same effect. Additionally or alternatively, a programmable aperture device such as a deformable mirror array or transmissive spatial light modulator can be used also.

Typically, a target will be aligned with its periodic structure features running either parallel to the Y axis or parallel to the X axis. With regard to its diffractive behavior, a periodic structure with features extending in a direction parallel to the Y axis has periodicity in the X direction, while the a periodic structure with features extending in a direction parallel to the X axis has periodicity in the Y direction. In order to measure the performance in both directions, both types of features are generally provided. While for simplicity there will be reference to lines and spaces, the periodic structure need not be formed of lines and space. Moreover, each line and/or space between lines may be a structure formed of smaller sub-structures. Further, the periodic structure may be formed with periodicity in two dimensions at once, for example where the periodic structure comprises posts and/or via holes.

Figure 8:
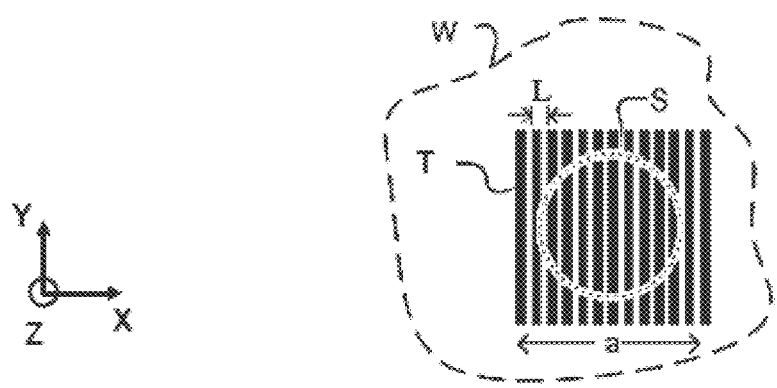
FIG. 8 illustrates the relationship between an illumination spot of a metrology apparatus and a metrology target.

FIG. 8 illustrates a plan view of a typical target T, and the extent of illumination spot S in the apparatus of FIG. 7. To obtain a diffraction spectrum that is free of interference from surrounding structures, the target T, in an embodiment, is a periodic structure (e.g., grating) larger than the width (e.g., diameter) of the illumination spot S. The width of spot S may be smaller than the width and length of the target. The target in other words is 'underfilled' by the illumination, and the diffraction signal is essentially free from any signals from product features and the like outside the target itself. This simplifies mathematical reconstruction of the target as it can be regarded as infinite.

Figure 9:
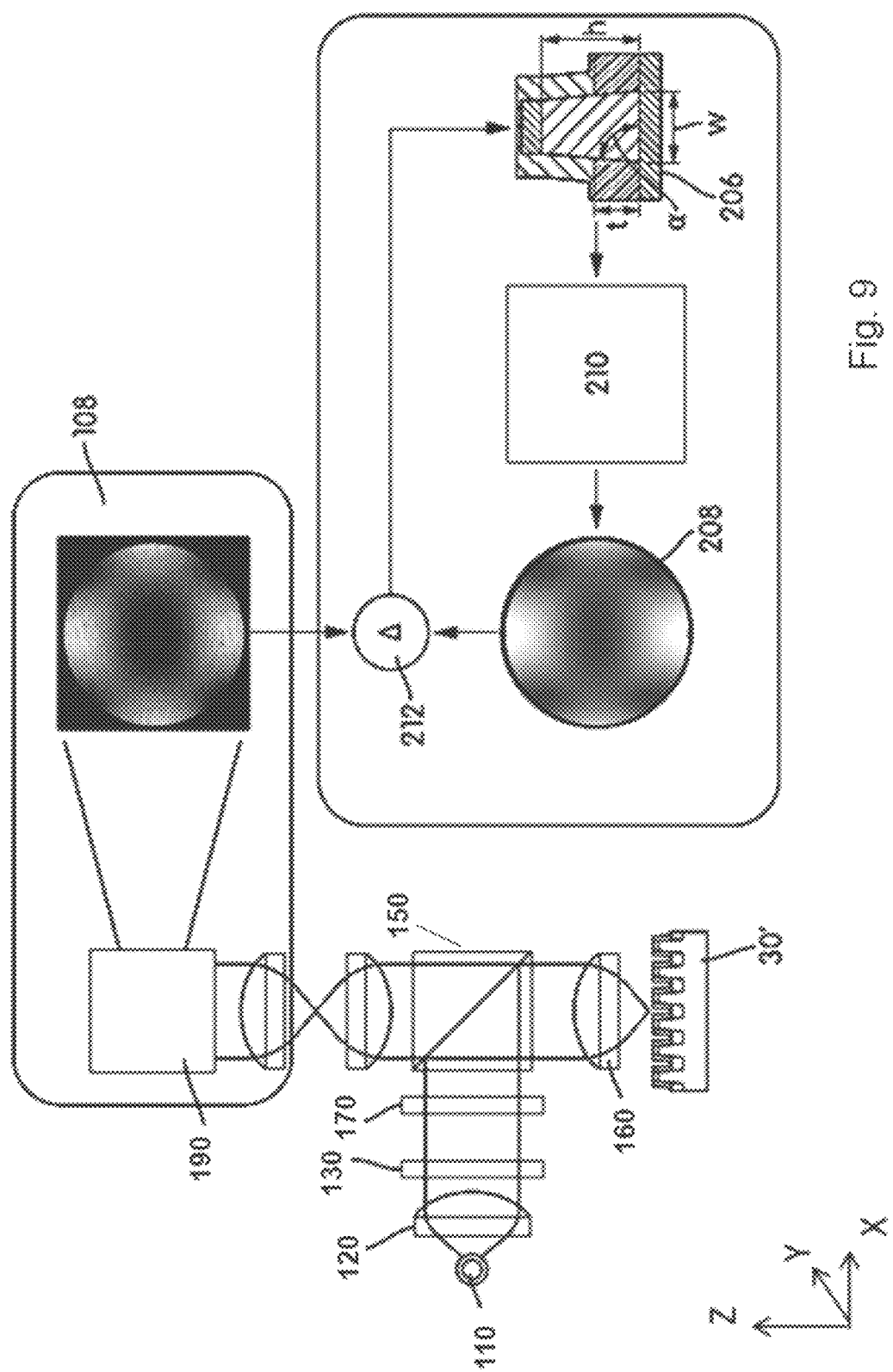
FIG. 9 schematically depicts a process of deriving one or more variables of interest based on measurement data.

FIG. 9 schematically depicts an example process of the determination of the value of one or more variables of interest of a target pattern 30' based on measurement data obtained using metrology. Radiation detected by the detector 190 provides a measured radiation distribution 108 for target 30'.

For the given target 30', a radiation distribution 208 can be computed/simulated from a parameterized mathematical model 206 using, for example, a numerical Maxwell solver 210. The parameterized mathematical model 206 shows example layers of various materials making up, and associated with, the target. The parameterized mathematical model 206 may include one or more of variables for the features and layers of the portion of the target under consideration, which may be varied and derived. As shown in FIG. 9, the one or more of the variables may include the thickness t of one or more layers, a width w (e.g., CD) of one or more features, a height h of one or more features, a sidewall angle α of one or more features, and/or relative position between features (herein considered overlay). Although not shown, the one or more of the variables may further include, but is not limited to, the refractive index (e.g., a real or complex refractive index, refractive index tensor, etc.) of one or more of the layers, the extinction coefficient of one or more layers, the absorption of one or more layers, resist loss during development, a footing of one or more features, and/or line edge roughness of one or more features. One or more values of one or more parameters of a 1-D periodic structure or a 2-D periodic structure, such as a value of width, length, shape or a 3-D profile characteristic, may be input to the reconstruction process from knowledge of the patterning process and/or other measurement processes. For example, the initial values of the variables may be those expected values of one or more parameters, such as a value of CD, pitch, etc., for the target being measured.

In some cases, a target can be divided into a plurality of instances of a unit cell. To help ease computation of the radiation distribution of a target in that case, the model 206 can be designed to compute/simulate using the unit cell of the structure of the target, where the unit cell is repeated as instances across the full target. Thus, the model 206 can compute using one unit cell and copy the results to fit a whole target using appropriate boundary conditions in order to determine the radiation distribution of the target.

Additionally or alternatively to computing the radiation distribution 208 at the time of reconstruction, a plurality of radiation distributions 208 can be pre-computed for a plurality of variations of variables of the target portion under consideration to create a library of radiation distributions for use at the time of reconstruction.

The measured radiation distribution 108 is then compared at 212 to the computed radiation distribution 208 (e.g., computed near that time or obtained from a library) to determine the difference between the two. If there is a difference, the values of one or more of the variables of the parameterized mathematical model 206 may be varied, a new computed radiation distribution 208 obtained (e.g., calculated or obtained from a library) and compared against the measured radiation distribution 108 until there is sufficient match between the measured radiation distribution 108 and the radiation distribution 208. At that point, the values of the variables of the parameterized mathematical model 206 provide a good or best match of the geometry of the actual target 30'. In an embodiment, there is sufficient match when a difference between the measured radiation distribution 108 and the computed radiation distribution 208 is within a tolerance threshold.

In these metrology apparatuses, a substrate support may be provided to hold the substrate W during measurement operations. The substrate support may be similar or identical in form to the substrate table WT of FIG. 1. In an example where the metrology apparatus is integrated with the lithographic apparatus, it may even be the same substrate table. Coarse and fine positioners may be provided to accurately position the substrate in relation to a measurement optical system. Various sensors and actuators are provided for example to acquire the position of a target of interest, and to bring it into position under the objective lens. Typically many measurements will be made on target instances at different locations across the substrate W. The substrate support can be moved in X and Y directions to acquire different target instances, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

In an embodiment, the measurement accuracy and/or sensitivity of a target may vary with respect to one or more attributes of the beam of radiation provided onto the target, for example, the wavelength of the radiation beam, the polarization of the radiation beam, the intensity distribution (i.e., angular or spatial intensity distribution) of the radiation beam, etc. Thus, a particular measurement strategy can be selected that desirably obtains, e.g., good measurement accuracy and/or sensitivity of the target.

In order to monitor the patterning process (e.g., a device manufacturing process) that includes at least one pattern transfer step (e.g., an optical lithography step), the patterned substrate is inspected and one or more parameters of the patterned substrate are measured/determined. The one or more parameters may include, for example, overlay between successive layers formed in or on the patterned substrate, critical dimension (CD) (e.g., critical linewidth) of, for example, features formed in or on the patterned substrate, focus or focus error of an optical lithography step, dose or dose error of an optical lithography step, optical aberrations of an optical lithography step, placement error (e.g., edge placement error), etc. This measurement may be performed on a target of the product substrate itself and/or on a dedicated metrology target provided on the substrate. The measurement can be performed after-development of a resist but before etching or can be performed after-etch.

In an embodiment, a parameter obtained from a measurement process is a parameter derived from a parameter determined directly from the measurement process. As an example, a derived parameter obtained from a measurement parameter is edge placement error for the patterning process. The edge placement error provides a variation in the location of an edge of a structure created by the patterning process. In an embodiment, the edge placement error is derived from an overlay value. In an embodiment, the edge placement error is derived from a combination of an overlay value and CD value. In an embodiment, the edge placement is derived from a combination of an overlay value, a CD value and a value corresponding to a local variation (e.g., edge roughness, shape asymmetry, etc. of the individual structures). In an embodiment, the edge placement error comprises an extreme value (e.g., 3 standard deviations, i.e., 3σ) of overlay and CD errors combined. In an embodiment, in a multi-patterning process involving creating structures and involving "cutting" structures by removing a portion of structure through etching of a pattern provided by the patterning process in relation to the structure, the edge placement error has the following form (or comprises one or more of the following terms):

$$\sqrt{(3\sigma_{overlay})^2 + \left(\frac{3\sigma_{CDU\ structures}}{2}\right)^2 + \left(\frac{3\sigma_{CDU\ cuts}}{2}\right)^2 + \frac{3\sigma_{OPE,PBA}}{2} + 6\sigma_{LER,LPE}},$$

wherein σ is standard deviation, $\sigma_{overlay}$ corresponds to the standard deviation of overlay, $\sigma_{CDU\ structures}$ corresponds to the standard deviation of the critical dimension uniformity (CDU) of structures created in the patterning process, $\sigma_{CDU\ cuts}$ corresponds to the standard deviation of the critical dimension uniformity (CDU) of cuts, if any, created in the patterning process, $\sigma_{OPE,\ PBA}$ corresponds to the standard deviation of optical proximity effects (OPE) and/or proximity bias average (PBA) which is a difference between CD at pitch to a reference CD, and $\sigma_{LER,\ LPE}$ corresponds to the standard deviation of line edge roughness (LER) and/or local placement error (LPE). While formulation above is in relation standard deviation, it can be formulated in a different comparable statistical manner, such as variance.

There are various techniques for making measurements of the structures formed in the patterning process, including the use of a scanning electron microscope, an image-based measurement tool and/or various specialized tools. As discussed above, a fast and non-invasive form of specialized metrology tool is one in which a beam of radiation is directed onto a target on the surface of the substrate and properties of the scattered (diffracted/reflected) beam are measured. By evaluating one or more properties of the radiation scattered by the substrate, one or more properties of the substrate can be determined. This may be termed diffraction-based metrology. One such application of this diffraction-based metrology is in the measurement of feature asymmetry within a target. This can be used as a measure of overlay, for example, but other applications are also known. For example, asymmetry can be measured by comparing opposite parts of the diffraction spectrum (for example, comparing the −1st and +1$^{st}$ orders in the diffraction spectrum of a periodic grating). This can be done as described above and as described, for example, in U.S. patent application publication US2006-066855, which is incorporated herein in its entirety by reference. Another application of diffraction-based metrology is in the measurement of feature width (CD) within a target. Such techniques can use the apparatus and methods described above in respect of FIGS. 6-9.

Now, while these techniques are effective, it is desirable to provide a new measurement technique that derives feature asymmetry within a target (such as overlay, CD asymmetry, sidewall angle asymmetry, etc.). This technique can be effective for specially designed metrology targets or perhaps more significantly, for determining feature asymmetry directly on a device pattern.

Figure 10C:
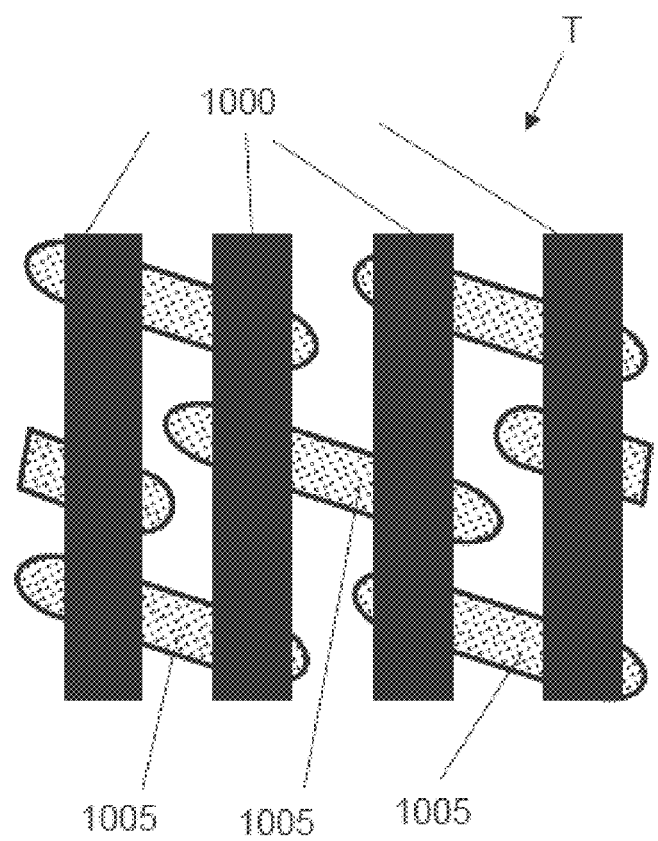
FIG. 10C schematically depicts an example target comprising one or more physical instances of a unit cell.

Referring to FIG. 10, principles of this measurement technique are described in the context of an overlay embodiment. In FIG. 10A, a geometrically symmetric unit cell of a target T is shown. The target T can comprise just a single physical instance of a unit cell or can comprise a plurality of physical instances of the unit cell as shown in FIG. 10C.

The target T can be a specially designed target. In an embodiment, the target is for a scribe lane. In an embodiment, the target can be an in-die target, i.e., the target is among the device pattern (and thus between the scribe lanes). In an embodiment, the target can have a feature width or pitch comparable to device pattern features. For example, the target feature width or pitches can be less than or equal to 300% of the smallest feature size or pitch of the device pattern, be less than or equal to 200% of the smallest feature size or pitch of the device pattern, be less than or equal to 150% of the smallest feature size or pitch of the device pattern, or be less than or equal to 100% of the smallest feature size or pitch of the device pattern.

The target T can be a device structure. For example, the target T can be a portion of a memory device (which often has one or more structures that are, or can be, geometrically symmetric as discussed further below).

In an embodiment, the target T or a physical instance of the unit cell can have an area of less than or equal to 2400 square microns, an area of less than or equal to 2000 square microns, an area of less than or equal to 1500 square microns, an area of less than or equal to 1000 square microns, an area of less than or equal to 400 square microns, less than or equal to 200 square microns, less than or equal to 100 square microns, less than or equal to 50 square microns, less than or equal to 25 square microns, less than or equal to 10 square microns, less than or equal to 5 square microns, less than or equal to 1 square micron, less than or equal to 0.5 square microns, or less than or equal to 0.1 square microns. In an embodiment, the target T or a physical instance of the unit cell has a cross-sectional dimension parallel to the plane of the substrate of less than or equal to 50 microns, less than or equal to 30 microns, less than or equal to 20 microns, less than or equal to 15 microns, less than or equal to 10 microns, less than or equal to 5 microns, less than or equal to 3 microns, less than or equal to 1 micron, less than or equal to 0.5 microns, less than or equal to 0.2 microns, or less than or equal to 0.1 microns.

In an embodiment, the target T or a physical instance of the unit cell has a pitch of structures of less than or equal to less than or equal to 5 microns, less than or equal to 2 microns, less than or equal to 1 micron, less than or equal to 500 nm, less than or equal to 400 nm, less than or equal to 300 nm, less than or equal to 200 nm, less than or equal to 150 nm, less than or equal to 100 nm, less than or equal to 75 nm, less than or equal to 50 nm, less than or equal to 32 nm, less than or equal to 22 nm, less than or equal to 16 nm, less than or equal to 10 nm, less than or equal to 7 nm or less than or equal to 5 nm.

In an embodiment, the target T has a plurality of physical instances of the unit cell. Thus, a target T could typically have the higher dimensions listed here, while the physical instances of the unit cell will have the lower dimensions listed here. In an embodiment, the target T comprises 50,000 or more physical instances of the unit cell, 25,000 or more physical instances of the unit cell, 15,000 or more physical instances of the unit cell, 10,000 or more physical instances of the unit cell, 5,000 or more physical instances of the unit cell, 1000 or more physical instances of the unit cell, 500 or more physical instances of the unit cell, 200 or more physical instances of the unit cell, 100 or more physical instances of the unit cell, 50 or more physical instances of the unit cell, or 10 or more physical instances of the unit cell.

Desirably, the physical instance of the unit cell or the plurality of physical instances of the unit cell collectively fills a beam spot of the metrology apparatus. In that case, the measured results comprise essentially only information from the physical instance of the unit cell (or its plurality of instances). In an embodiment, the beam spot has a cross-sectional width of 50 microns or less, 40 microns or less, 30 microns or less, 20 microns or less, 15 microns or less, 10 microns or less, 5 microns or less, or 2 microns or less.

The unit cell in FIG. 10A comprises at least two structures that are, or will be, physically instantiated on the substrate. A first structure 1000 comprises lines and a second structure 1005 comprises an oval-type shape. Of course, the first and second structures 1000, 1005 can be different structures than depicted.

Further, in this example, there can be a relative shift between the first and second structures 1000, 1005 from their expected position due to their separate transfer onto the substrate so as to have an error in overlay. In this example, the first structure 1000 is located in a higher layer on a substrate than the second structure 1005. Thus, in an embodiment, the second structure 1005 can be produced in a first lower layer in a first execution of a patterning process and the first structure 1000 can be produced in a second higher layer than the first lower layer in a second execution of the patterning process. Now, it is not necessary that the first and second structures 1000, 1005 be located in different layers. For example, in a double patterning process (including, for example, an etching process as part thereof), the first and second structures 1000, 1005 could be produced in a same layer to form essentially a single pattern but there could still be an "overlay" concern in terms of their relative placement within the same layer. In this single layer example, both the first and second structures 1000, 1005 could have, for example, the form of lines like shown in FIG. 10A for the first structure 1000 but the lines of the second structure 1005, already provided on the substrate by a first pattern transfer process, could be interleaved with the lines of the structure 1000 provided in a second pattern transfer process.

Significantly, the unit cell has, or is capable of having, a geometric symmetry with respect to an axis or point. For example, the unit cell in FIG. 10A has reflection symmetry with respect to, for example, axis 1010 and point/rotational symmetry with respect to, for example, point 1015. Similarly, it can be seen that a physical instance of the unit cell (and thus a combination of physical instances of the unit cell) in FIG. 10C has a geometric symmetry.

In an embodiment, the unit cell has a geometric symmetry for a certain feature (such as overlay). Embodiments herein focus on the unit cell having zero overlay when it is geometrically symmetric. However, instead, the unit cell can have zero overlay for a certain geometric asymmetry. Appropriate offsets and calculations would then be used to account for the unit cell having a zero overlay when it has a certain geometric asymmetry. Pertinently, the unit cell should be capable of change in symmetry (e.g., become asymmetry, or become further asymmetric, or become symmetric from an asymmetric situation) depending on the certain feature value.

In the example of FIG. 10A, the unit cell has a geometric symmetry for a zero overlay (although it need not be zero overlay). This is represented by the arrows 1020 and 1025 which shows that the lines of the first structure 1000 are evenly aligned with respect to the oval-type shape of the second structure 1005 (and which even alignment at least in part enables the unit cell to have geometric symmetry as shown in FIG. 10A). So, in this example, when the unit cell has geometric symmetry, there is zero overlay. However, when there is an error in overlay (e.g., a non-zero overlay), the unit cell is no longer geometrically symmetric and by definition the target is no longer geometrically symmetric.

Further, where a target comprises a plurality of physical instances of the unit, the instances of the unit cell are arranged periodically. In an embodiment, the instances of the unit cell are arranged in a lattice. In an embodiment, the periodic arrangement has a geometric symmetry within the target.

So, in this technique, as discussed further hereafter, advantage is taken of the change in geometric symmetry (e.g., a change to a geometric asymmetry, or change to a further geometric asymmetry, or a change from geometric asymmetry to geometric symmetry) related to a feature asymmetry of interest (e.g., non-zero overlay) to be able to determine the feature asymmetry (e.g., non-zero overlay).

A target comprising a physical instance of the unit cell of FIG. 10A can be illuminated with radiation using, for example, the metrology apparatus of FIG. 7. The radiation redirected by the target can be measured, e.g., by detector 190. In an embodiment, a pupil of the redirected radiation is measured, i.e., a Fourier transform plane. An example measurement of such a pupil is depicted as pupil image 1030. While the pupil image 1030 has a diamond-type shape, it need not have such a shape. The term pupil and pupil plane herein includes any conjugates thereof unless the context otherwise requires (for example, where a pupil plane of a particular optical system is being identified). The pupil image 1030 is effectively an image, specified in terms of an optical characteristic (in this case intensity), of a pupil of the redirected radiation.

For convenience, the discussion herein will focus on intensity as an optical characteristic of interest. But, the techniques herein may be used with one or more alternative or additional optical characteristics, such as phase and/or reflectivity.

Further, for convenience, the discussion herein focuses on detecting and processing images of redirected radiation and in particular pupil images. However, the optical properties of the redirected radiation can be measured and represented in different manners than images. For example, the redirected radiation can be processed in terms of one or more spectrums (e.g., intensity as a function of wavelength). Thus, a detected image of redirected radiation can be considered as an example of an optical representation of the redirected radiation. So, in the case of a pupil plane image, a pupil image is an example of a pupil representation.

Further, the redirected radiation can be polarized or non-polarized. In an embodiment, the measurement beam radiation is polarized radiation. In an embodiment, the measurement beam radiation is linearly polarized.

In an embodiment, a pupil representation is of primarily, or substantially, one diffraction order of redirected radiation from the target. For example, the radiation can be 80% or more, 85% or more, 90% or more, 95% or more, 98% or more or 99% or more, of a particular order of the radiation. In an embodiment, the pupil representation is of primarily, or substantially, zeroth order redirected radiation. This can occur, for example, when the pitch of the target, the wavelength of the measurement radiation, and optionally one or more other conditions cause the target to redirect primarily zeroth order (although there can be radiation of one or more higher orders). In an embodiment, a majority of the pupil representation is zeroth order redirected radiation. In an embodiment, the pupil representation is of zeroth radiation and separately of $1^{st}$ order radiation, which can then be linearly combined (superposition). The aperture 186 in FIG. 7 can be used to select a particular order, e.g., the zeroth order, of radiation.

Having regard to pupil image 1030 corresponding to the geometrically symmetric unit cell of the first and second structures 1000, 1005, it can be seen that the intensity distribution is essentially symmetric within the pupil image (e.g., with the same symmetry type as of the geometric structure). This is further confirmed by removing the symmetric intensity distribution portion from the pupil image 1030, which results in the derived pupil image 1035. To remove the symmetric intensity distribution portion, a particular pupil image pixel (e.g., a pixel) can have the symmetric intensity distribution portion removed by subtracting from the intensity at that particular pupil image pixel the intensity of a symmetrically located pupil image pixel, and vice versa. In an embodiment, the pixel can correspond to the pixels of the detector (e.g., detector 190), but it need not, for example, a pupil image pixel could be a plurality of the pixels of the detector. In an embodiment, the point or axis of symmetry across which pixel intensities are subtracted corresponds with a point or axis of symmetry of the unit cell. So, for example, considering pupil image 1030, the symmetry intensity distribution portion can be removed by, for example, subtracting from the intensity $I_i$ at that particular pixel shown the intensity $I_i'$ from a symmetrically located pixel, i.e., symmetrically located with respect to axis 1032. Thus, the intensity at a particular pixel with the symmetrical intensity portion removed, $S_i$, is then $S_i=I_i-I_i'$. This can be repeated for a plurality of pixels of the pupil image, e.g., all the pixels in the pupil image. As seen in the derived pupil image 1035, the intensity distribution corresponding to the symmetric unit cell is essentially completely symmetric. Thus, a symmetric target with a symmetric unit cell geometry (and if applicable, a certain periodicity of instances of the unit cell) results in a symmetric pupil response as measured by a metrology apparatus.

Referring now to FIG. 10B, an example of an error in overlay is depicted with respect to the unit cell depicted in FIG. 10A. In this case, the first structure 1000 is shifted in the X-direction with respect to the second structure 1005. In particular, the axis 1010 centered on the lines of the first structure 1000 has shifted to the right in FIG. 10B to axis 1045. Thus, there is an error in the overlay 1040 in the X-direction; that is, an X direction overlay error. Of course, the second structure 1005 could be shifted relative to the first structure 1000 or both could be shifted relative to each other. In any event, the result is an X direction overlay error. However, as should be appreciated from this unit cell arrangement, a purely relative shift in the Y-direction between the first structure 1000 and the second structure 1005 would not change the geometric symmetry of this unit cell. But, with an appropriate geometric arrangement, overlay in two directions or between different combinations of parts of the unit cell can change symmetry and could also be determined, as further discussed below.

As a consequence of the change in the physical configuration of the unit cell from the nominal physical configuration of the unit cell in FIG. 10A and represented by the error in overlay 1040, the result is that the unit cell has become geometrically asymmetric. This can be seen by the arrows 1050 and 1055 of different length, which show that the oval-type shape of the second structure 1005 is unevenly located relative to the lines of the first structure 1000. The symmetry is examined with respect to the point or axis of symmetry of the pupil image 1030, i.e. in that case, axis 1032 which is now shown axis 1034.

The physical instance of the unit cell of FIG. 10B can be illuminated with radiation using, for example, the metrology apparatus of FIG. 7. A pupil image of the redirected radiation can be recorded, e.g., by detector 190. An example of such a pupil image is depicted as pupil image 1060. The pupil image 1060 is effectively an image of the intensity. While the pupil image 1060 has a diamond-type shape, it need not have such a shape; it can be a circular shape or any other shape. Moreover, the pupil image 1060 is of a substantially same axis or coordinate location as pupil image 1030. That is, in this embodiment, an axis of symmetry 1010 in the unit cell of FIG. 10A and the same axis in the unit cell of FIG. 10B align with an axis of symmetry 1032 of the pupil images 1030, 1060.

Having regard to pupil image 1060 corresponding to the geometrically asymmetric unit cell of the first and second structures 1000, 1005, it visually seems like the intensity distribution is essentially symmetric within the pupil image. However, there is an asymmetric intensity distribution portion within the pupil image. This asymmetric intensity distribution portion is due to the asymmetry in the unit cell. Moreover, the asymmetric intensity distribution is significantly lower in magnitude than a symmetric intensity distribution portion in the pupil image.

So, in an embodiment, to more effectively isolate the asymmetric intensity distribution portion, the symmetric intensity distribution portion can be removed from the pupil image 1060, which results in the derived pupil image 1065. Like with obtaining derived pupil image 1035, a particular pupil image pixel (e.g., a pixel) can have the symmetric intensity distribution portion removed by subtracting from the intensity at that particular pupil image pixel the intensity of a symmetrically located pupil image pixel, and vice versa, as discussed above. So, for example, considering pupil image 1060, the symmetry intensity distribution portion can be removed by, for example, subtracting from the intensity $I_i$ at that particular pixel shown the intensity $I_i'$ from a symmetrically located pixel, i.e., symmetrically located with respect to axis 1032 to yield $S_i$. This can be repeated for a plurality of pixels of the pupil image, e.g., all the pixels in the pupil image. In FIGS. 10A and 10B, the full derived pupil images of $S_i$ are depicted for explanation purposes. As will be appreciated, half of a derived pupil image of FIG. 10A or 10B is the same as the other half thereof. So, in an embodiment, the values from only half of the pupil image can be used for further processing discussed herein and so a derived image pupil used in further processing herein can be only half of the $S_i$ values for a pupil.

As seen in the derived pupil image 1065, the intensity distribution measured using a physical instance of an asymmetric unit cell is not symmetric. As seen in regions 1075 and 1080, there is an asymmetric intensity distribution portion visible once the symmetric intensity distribution portion is removed. As noted above, the full derived pupil image 1065 is shown and so the asymmetric intensity distribution portion is shown on both halves (even though they are equal to each other in terms of magnitude and distribution in their respective halves).

Thus, an asymmetry in the geometrical domain corresponds to an asymmetry in the pupil. So, in an embodiment, a method is provided that uses the optical response of a periodic target that possesses, or is capable of, inherent geometric symmetry in its physical instance of a unit cell to determine a parameter corresponding to a physical configuration change that causes a change in geometric symmetry (e.g., cause an asymmetry, or cause a further asymmetry, or cause an asymmetric unit cell to become symmetric) of the physical instance of the unit cell. In particular, in an embodiment, an overlay induced asymmetry (or lack thereof) in the pupil as measured by a metrology apparatus can be exploited to determine the overlay. That is, the pupil asymmetry is used to measure the overlay within the physical instance of the unit cell and thus within the target.

To consider how to determine the parameter corresponding to a physical configuration change that causes a geometric asymmetry in a unit cell, the intensity of a pixel in the pupil image can be considered in terms of the physical characteristics of the target that impact that pixel. To do so, an overlay example will be considered but the techniques and principles can be extended to another parameter corresponding to a physical configuration change that causes a geometric asymmetry in a unit cell (e.g., asymmetric sidewall angle, asymmetric bottom wall tilt, ellipticity in contact holes, etc.).

Referring back to the unit cells of FIGS. 10A and 10B, the intensity of a pixel $I_i$, $I'_i$ in the pupil image 1060 can be evaluated analytically as a combination of intensity components attributable to different physical characteristics of the unit cell. In particular, the physical configuration changes from the symmetric unit cell to the asymmetric unit cell can be evaluated to determine in what manner the intensity distribution changes and specifically within a pupil image.

So, in a very simple example to illustrate the principles, several changes in physical configuration of the unit cell profile can be evaluated (but of course more or different physical configuration changes can occur). One of the physical configuration changes that will be considered is the change in height of the structure 1000 in the Z direction, which is designated as $\Delta x_h$. But, significantly, this change in height will generally be uniform across the physical instance of the unit cell. That is, the $\Delta x_h$ will result in a same changed physical configuration of the unit cell at one side of an axis or point of symmetry as at another side of the axis or point of symmetry. Similarly, other physical configuration changes, such as CD, sidewall angle, etc. changes, will also be generally uniform across the physical instance of the unit cell and thus yield a same changed physical configuration of the unit cell at one side of an axis or point of symmetry as at another side of the axis or point of symmetry. So, for convenience, only $\Delta x_h$ will be considered, but is representative of numerous other physical configuration changes that are uniform across the unit cell.

Another one of the physical configuration changes of the unit cell of interest is the relative shift between structure 1000 and structure 1005, namely the change in overlay 1040. This overlay shift will be referred to as $\Delta x_{ov}$. Of course, the overlay can be considered in a different or additional direction. Significantly, the $\Delta x_{ov}$ will result in a different physical configuration of the unit cell at one side of an axis or point of symmetry than at another side of the axis or point of symmetry; each pair of symmetric pixels has information about overlay. Significantly, while change in most target profile parameters (CD, height, etc.) induce symmetric changes in the pupil (and thus can be considered symmetric parameters), change in overlay results in an asymmetric change in the measured pupil. Thus, a change in overlay gives an asymmetric pupil response. Further, most, if not all, other unit cell profile parameters do not create asymmetry of the unit cell or the pupil response. However, they can have an effect on the measured overlay value. As discussed below, to the first order, other unit cell profile parameters may have no effect. In an embodiment, to a second or higher order, other unit cell profile parameters have an effect on determination of the overlay value. Hence, as discussed in more detail below, by measuring the pupil asymmetry, overlay can be determined therefrom.

Specifically, to evaluate how overlay can be determined from a measured pupil asymmetry, the intensity $I_i$ of a pixel i in the pupil image 1060 can be defined as:

$$I_i = I_0 + a\Delta x_{ov} + d\Delta x_h + b\Delta x_{ov}\Delta x_h + e\Delta x_{ov}^2 + f\Delta x_h^2 + \ldots \\ c\Delta x_{ov}^3 + \ldots \quad (1)$$

where $I_0$ is a base intensity attributable to the illumination radiation and a, e, f and g are coefficients. So, similarly, the intensity of the complementary symmetric pixel $I'_i$ in the pupil image 1060 can be defined as:

$$I'_i = I_0 + a'\Delta x_{ov} + d'\Delta x_h + b'\Delta x_{ov}\Delta x_h + e'\Delta x_{ov}^2 + f'\Delta x_h^2 + \ldots \\ c'\Delta x_{ov}^3 + \ldots \quad (2)$$

where coefficients a', b', c', d', e' and f' are specific to the intensity of the complementary symmetric pixel $I'_i$ and are related to the coefficients a, b, c, d, e and f for the intensity of a pixel it in the pupil image 1060.

The difference of the intensity $S_i = I_i - I'_i$ between the symmetric pixels in the pupil image 1060 can then be evaluated as:

$$S_i = I_i - I'_i = (a-a')\Delta x_{ov} + (b-b')\Delta x_{ov}\Delta x_h + (c-c')\Delta x_{ov}^3 + \ldots \quad (3)$$

It has been discovered that due to, e.g., symmetry, all the terms that can contain only symmetric parameters, such as $e\Delta x_h$, drop out as seen in equation (3). Further, due to, e.g., symmetry, the terms with an even power of overlay have been discovered to be equal for symmetrically positioned pixels and so terms such $\Delta x_{ov}^2$ likewise drop out. That leaves, terms that have a combination of overlay with a symmetric parameter and terms that have only overlay to an odd power (e.g., to the power of 1, 3, 5, 7, etc.).

In equation (3) above, it has been discovered that the difference of the intensity $S_i$ is primarily dependent on $a\Delta x_{ov}$. That is, the difference of the intensity $S_i$ is in great part linearly dependent on overlay or more significantly, overlay is in great part linearly dependent on the intensity, specifically the difference of the intensity $S_i$. Thus, a combination of the intensities of the pixels can yield a good estimated value of the overlay when linearly combined with an appropriate conversion factor.

So, in an embodiment, it has been discovered that an overlay can be determined from a combination of intensities of the pixels that are appropriately weighted (wherein the weighting themselves acts a conversion factor of intensity to overlay or that can be combined with a conversion factor from intensity to overlay). In an embodiment, an overlay signal can be described as:

$$M = \Sigma_i w_i S_i \quad (4)$$

wherein the overlay signal M is the weighted combination of the signal components $S_i$ in the measured pupil and $w_i$ are the respective weights for each of the signal components $S_i$ (and the weights act as a conversion factor between the signal component and overlay; as noted above, instead, a conversion factor could be used in combination with weights that do not act to convert the signal component to overlay). In an embodiment, the weights $w_i$ are a vector whose magnitude is related to the overlay. As noted above, the signal components $S_i$ can be determined for half of the measured pupil. In an embodiment, if the signal components $S_i$ have a substantially same magnitude for all pairs (N/2) of symmetric pixels (N), then the signal components $S_i$ can be averaged and combined with a conversion factor C from the total of the signal components $S_i$ to overlay according to the following formula to yield a total overlay:

$$M = C \frac{2}{N} \sum_{i}^{N/2} S_i.$$

So, in an embodiment, the weights can have two roles—one is as a trust per pair of pixels in respect of its measurement of overlay and the other role is to convert a value of the optical characteristic of the signal component (e.g., intensity level, e.g., gray level) to an overlay value (in terms of, e.g., nanometers), As discussed above, the second role can be delegated to a conversion factor.

But, where, e.g., the signal components S, do not have a substantially same magnitude for all pairs of symmetric pixels, weighting all pixels in the measured pupil equally could result in a low signal-to-noise ratio (poor precision). So, it is desirable to weight those pixels that are sensitive to overlay to have a greater contribution to the calculation of the overlay. So, in an embodiment, pixels sensitive to overlay get different (e.g., higher) weights than those pixels that have low sensitivity to overlay (effectively inactive pixels). As noted above, the pixels in regions 1075 and 1080 of the derived pupil 1065 have relatively higher sensitivity to overlay while the remaining pixels in the derived pupil 1065, which have low to no intensity relative to the pixels in regions 1075 and 1080, have low sensitivity to overlay (and accordingly should be weighted to have lower contribution to the overlay determination).

In an embodiment, the weights are effectively determined for the $a\Delta x_{ov}$ term of equation (3). In an embodiment, the weights can be extended to be determined for the $a\Delta x_{ov}$ term as well as the $b\Delta x_{ov}\Delta x_h$ (and typically other comparable terms for other parameters, such as CD, sidewall angle, etc.). However, this calculation can be more complex than determining the weights effectively only for the $a\Delta x_{ov}$ term of equation (3). Moreover, there is a tradeoff between robustness to non-linear processes (for symmetric parameters) and precision of determining overlay (i.e., in terms of how close the determined values are for each determination of the same actual overlay). So, there can be a sacrifice of precision for enhanced robustness using this calculation. Accordingly, an optimization can be performed to enhance precision (e.g., maximizing the influence of the linear terms and suppressing the non-linear terms), enhance robustness (e.g., maximizing the non-linear terms) or find a balance of both. But, in any event, the use of a combination of intensities linearly combined with associated weightings can lead to a quick determination of overlay as it requires merely a pupil acquisition and simple calculation of equation (4).

In an embodiment, where higher order terms become significant, a non-linear solution technique can be adopted to solve equation (3) having the $c\Delta x_{ov}^3$, and/or other higher order terms. As will be appreciated, a non-linear solution technique can be more complex than simply multiplying each signal components $S_i$ in the measured pupil with a respective weight $w_i$ for each signal components $S_i$ and then adding all of them up. Moreover, there is again tradeoff between robustness to non-linear processes and precision of determining overlay (i.e., in terms of how close the determined values are for each determination of the same actual overlay). So, there can be a sacrifice of precision for enhanced robustness using this calculation. Accordingly, an optimization can be performed to enhance precision and/or enhance robustness.

So, with the realization of an asymmetric intensity distribution arising from a geometric asymmetry of a unit cell caused by overlay, the error in overlay can be determined through an analysis that has a focus on this asymmetric intensity distribution. Thus, a technique for determining overlay from the asymmetric intensity distribution arising due to the change in physical configuration of a target associated with overlay will now be discussed.

Figure 11:
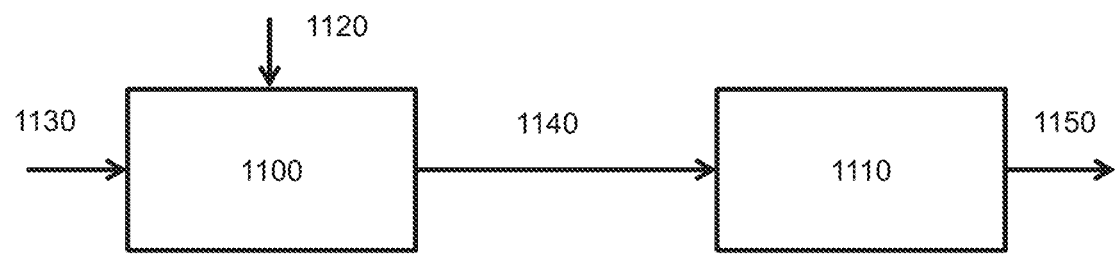
FIG. 11 depicts a high-level flow of obtaining weightings for determining a patterning process parameter from measured radiation.

Referring to FIG. 11, a method of determining the weights is schematically depicted. To enable the weight determination, the reconstruction techniques described above with respect to FIG. 9 will be used to advantage. That is, in an embodiment, CD reconstruction is used to isolate an overlay signal from a pupil image of a physical instance of an asymmetric unit cell.

The method of FIG. 11 involves two processes. A first process 1100 involves using reconstruction techniques for CD and/or one or more other profile parameters of a target to derive a nominal profile of the target (and thus of the one or more physical instances of the unit cell therein) as exposed on a substrate as part of a patterning process. With the nominal profile of the target, the basic engine of the reconstruction technique is used in process 1110 to derive the weightings. The weightings can then be used to derive overlay from a measured pupil as described further in relation to FIG. 12.

So, at process 1100, measurements 1130 of a substrate having one or more physical instances of a unit cell of interest provided thereon as a target, are obtained. In an embodiment, the measurements are of the target after etch. In an embodiment, the measurements are of the target after development but before etch. In an embodiment, the target is a device structure. In an embodiment, the measurements can be made, or have been made, using a metrology apparatus such as the metrology apparatus of FIG. 7. For example, the target can comprise a physical instance of the unit cell of FIG. 10A or FIG. 10B, e.g. a single instance or a plurality of adjacent instance as shown in FIG. 10C. In an embodiment, measurements of a plurality of instances of a target (and thus of a plurality of physical instances of the unit cell) are obtained. In an embodiment, the measurements are of target instances that are distributed across the substrate. In an embodiment, a plurality of substrates, each with one or more target instances (each having one or more physical instances of the unit cell), is measured. So, in an embodiment, a radiation distribution 108 is obtained for each measured target.

Then, a reconstruction process at 1100, such as the reconstruction process described in and with respect to FIG. 9, is used to derive a nominal profile of the physical instance of the unit cell, comparable to the profile 206 of FIG. 9. The reconstruction process obtains an expected profile 1120 of the physical instance of the unit cell to start and facilitate the reconstruction process. In an embodiment, the derived nominal profile is obtained from an average of the profile of target instances across one or more substrates. For example, the radiation distribution 108 for each target can be processed to derive a particular profile of that instance of the target and then the profiles for the plurality of instances of the target can be averaged together to derive the nominal profile. In an embodiment, the nominal profile comprises at least a geometric profile of the target. In an embodiment, the geometric profile is a 3-D profile. In an embodiment, the nominal profile comprises information regarding one or more materials properties of one or more layers making up the physical target.

So, in an embodiment, the nominal profile can be considered as a center of gravity for the values of various parameters of the profile of the target (and thus the unit cell)

obtained from measuring numerous instances of the target across the substrate and optionally on more than one substrate. But, in an embodiment, the nominal profile can have different forms and be more specific. For example, the nominal profile can be defined for one or more particular instances of a target (e.g., by using values from the same target location(s) from multiple substrates). As another example, the nominal profile can be defined for a particular substrate (e.g., by using values from only that substrate). In an embodiment, the nominal profile can be tuned for a particular target and/or substrate as part of the process of FIG. 12. For example, when the target and/or substrate is measured as part of the process of FIG. 12, a reconstruction technique can be used with the measured data to fine tune the nominal profile for that target and/or substrate, the fine-tuned nominal profile can then be used as the nominal profile herein to determine weights and which weighs can then be used with the same measured data to yield one or more overlay values.

The reconstructed nominal profile 1140 is then provided to process 1110. Thus, in an embodiment, process 1110 uses a derived nominal profile of the target, e.g., a geometric after-etch profile of the unit cell of a device derived from measured data. In an embodiment, the nominal profile can be in the form of a parameterized model, like model 206 parameterized in accordance with the measured unit cell. Thus, in an embodiment, process 1110 uses a derived profile model of the unit cell, e.g., a model of the geometric after-etch profile of the physical instance of a unit cell of a device derived from measured data.

The basic engine of the reconstruction technique described herein is used in process 1110, along with the derived profile or the derived profile model, to derive the weightings. In an embodiment, the derived profile model or a derived profile model derived from the derived profile is used to determine pupil pixels sensitive to overlay in the unit cell. In particular, in an embodiment, the sensitivity to overlay of pupil response is determined by, using simulations (e.g., the Maxwell solver), to determine a change in pupil response to an induced change in overlay for the nominal profile.

This can be accomplished by causing the derived profile model to be changed such that an overlay change of a certain amount is induced (e.g., 1 nm) in the model, leaving all other parameters/variables of the derived profile model unchanged. This effectively causes a symmetric unit cell to become asymmetric or causes an already asymmetric unit cell ell can be symmetric) to change symmetry (including to become further asymmetric or to become symmetric from an asymmetric situation).

A pupil as would be expected in the metrology apparatus (e.g., for radiation at a certain measurement beam wavelength, measurement beam polarization, measurement beam intensity, etc.) can then be derived (e.g., using a Maxwell solver, a library search or other reconstruction technique) based on the derived profile model with the induced overlay change. Where the physical instance of the unit cell is smaller than a beam spot, the reconstruction can treat the beam spot as being filled with physical instances of the unit cell. In an embodiment, the derived pupil can be a simulated pupil image 1060 and/or a derived pupil image 1065 based on the simulated pupil image.

The derived pupil can be then used to determine the sensitivities of the intensity in a plurality of the pupil pixels to overlay change, for example by comparison with a derived pupil for the unit cell without the induced overlay (for example, the derived pupil for the unit cell without the induced overlay can be a simulated pupil image 1030 and/or a derived pupil image 1035 based on the simulated pupil image). In an embodiment, these sensitivities form the basis of the weightings.

In an embodiment, the pixels of the pupil (and thus the pixel intensities, signal components $S_i$, etc.) can be expressed as a vector. In an embodiment, the weightings can then be derived from a Jacobian matrix generated in the modelling. In an embodiment, the weightings can be derived from a Moore-Penrose pseudo inverse of the Jacobian matrix generated in the modelling. So, the weights are effectively determined for the $a\Delta x_{ov}$ term of equation (3). The weightings derived from the Jacobian matrix or the Moore-Penrose pseudo inverse of the Jacobian matrix appear to apply well for the relatively modest overlay variations (e.g., within ±3 nm or within ±4 nm or within ±5 nm).

In an embodiment, the weights can be extended to be determined for the $a\Delta x_{ov}$ term as well as the $b\Delta x_{ov}\Delta x_h$ (and typically other comparable terms for other parameters, such as CD, sidewall angle, etc.). In this case, the weightings are, or can be derived from, a Hessian matrix generated in the modelling in addition to the Jacobian matrix. The Hessian shows how the response to the overlay changes due to a change of a certain amount of another (symmetric) parameter (such as CD). So, for every such parameter there is a column in the Hessian. In an embodiment, to be (more) robust, the weights could be altered such that they become more orthogonal to the column (parameter) for which the unit cell is sensitive. To become more orthogonal, the one or more sensitive columns can be concatenated to the Jacobian, and then the Moore-Penrose pseudo inverse can be computed from this Jacobian with one or more columns from the Hessian concatenated thereto. From this computation, the weights follow. However, this calculation can be more complex and thus may be suitable for those situations where overlay values in practice are expected to exceed the overlay variation range for which the weightings derived from the (Moore-Penrose pseudo inverse of) Jacobian matrix show good results.

In an embodiment, the weights can be extended to be determined for other terms of equation (3). In that case, the weightings are, or can be derived from, third order derivatives generated in the modelling in addition to the Jacobian matrix.

As noted above, the nominal profile could be a fine-tuned nominal profile per target or substrate. For example, when the particular target or substrate is measured as part of the process of FIG. 12, a reconstruction technique can be used with the measured data to fine tune the nominal profile for that target or substrate. Now, depending on the fine-tuning, the weights can be (re-)determined and/or a choice made between the type of weighting being made (e.g., Jacobian or a combination of the Jacobian and Hessian). For example, weights, based on a nominal profile that wasn't fine-tuned, may have been previously selected to suppress the effect of $\Delta x_h$, but if the fine-tuning identifies and updates the $\Delta x_h$ for the target and/or substrate, the effect of $\Delta x_h$ may not need to be suppressed. Thus, weights could be chosen that more favor precision over robustness.

So, from process 1110, a collection (e.g., a vector) of weights $w_i$ can be output. The weights $w_i$ themselves can act as a conversion factor of intensity to overlay or they can be combined with a conversion factor from intensity to overlay (which conversion factor can be derived as part of the same modelling). As will be appreciated from pupil image 1065, the pixels in the regions 1075 and 1080 have relatively higher sensitivity to overlay than pixels outside of regions 1075 and 1080 and thus their weightings will be noticeably different (e.g., higher) than the weighting of pixels outside of region 1075 and 1080 (which pixels have relatively low sensitivity to overlay). So, when the weights are combined (such as according to equation (4)) with measured intensity values of a target having one or more physical instances of the unit cell, an overlay signal can be obtained for the particular target (such as a device pattern having a physical instance of the unit cell).

Further, one or more measurement parameters can be determined to form a measurement strategy for use in obtaining the measured intensity values of the target. One or more measurement parameters can affect the overlay sensitivity of pixels. For example, overlay sensitivity varies across different measurement beam wavelengths. So, in an embodiment, one or more measurement parameters (such as wavelength, polarization, dose, a number of optical characteristic readings taken by a detector sensor of a particular one illumination of the target (the readings typically averaged to provide an averaged optical characteristic value for the measurement of the target)) can be varied as part of the modelling process 1110. For example, one or more measurement parameters can be examined for a particular induced overlay change to determine a value of the one or more measurement parameters that reduces an error residual, for example between an overlay obtained when the weightings are for one value of the one or more parameters in relation to overlay obtained when the weightings are for another value of the one or more parameters, to a minimum or below a certain threshold. So, a value of one or more measurement parameters can then be obtained that improve precision.

Further, robustness to process variations differs across different values of one or more measurement parameters. For example, in particular, robustness to process variations differs across different values of measurement beam wavelength and/or measurement polarization. Thus, in an embodiment, the weighting scheme should address at least a dominant contributor to lack of robustness to process variation. So, additionally or alternatively to determining a value of one or more measurement parameters for improved precision, one or more measurement parameters can be examined for different particular induced overlay change values (and/or for particular induced changes of one or more other parameters of the derived profile model, such as a change in CD, side wall angle, etc.) to obtain a value of one or more measurement parameters that enables results using the weightings that have enhanced robustness to process variation. For example, for different amounts of induced overlay change, various values of the one or more measurement parameters can be evaluated to determine a value of the one or more measurement parameters that causes a minimum (or below a threshold) variation in the determined overlay using the weightings associated with the value of the one or more measurement parameters. Of course, a balance can be used in selection of the value of the one or more measurement parameters between precision and enhanced robustness. For example, a weighting can be applied between a value of the one or more measurement parameters determined for precision (e.g., a weight applied to a performance metric that measures precision) and a value of the one or more measurement parameters determined for enhanced robustness (e.g., a weight applied to a performance metric that measures robustness) and then a largest, top ranked, etc. combination can be selected. And of course, a plurality of values of one or more measurement parameters can be determined such that there is in effect a plurality of different measurement strategies in the overall measurement strategy. The plurality of values could be ranked according to one or more performance metrics. Thus, optionally, a measurement strategy can be output from process 1110 for use in obtaining measured intensity values of a target having one or more physical instances of the unit cell.

Further, one or more non-overlay parameters, such as CD, sidewall angle, etc., can affect the weights used for mapping the intensity signal to overlay. As noted above, an example manner of determining the weights in this context is to use a Hessian matrix and/or third order derivatives. So, in an embodiment, various possible weighting schemes are possible to take account of one or more non-overlay parameters so as to still maintain a good overlay value. In an embodiment, the overlay informative overlay pixels and their weightings can be optimized for overlay determination precision. This may require good model quality, i.e., good estimates of the non-overlay parameters. In an embodiment, the overlay informative pixels and their weights can be optimized for increased robustness to process variations such as in the non-overlay parameters. This may be at the expense of precision.

In an embodiment, estimates of the one or more non-overlay parameters can be made using, for example, the reconstruction techniques described in relation to FIG. 9, and fed-forward to tune the derived profile or derived profile model. For example, a CD reconstruction can estimate a CD of a target at a particular location at a substrate and/or for a particular combination of patterning process settings (e.g., exposure dose, exposure focus, etc.) and use that CD estimate to tune the CD parameter of the derived profile or derived profile model. In an embodiment, iterative reconstructions of the exact derived profile or derived profile model parameters can be performed.

Figure 12:
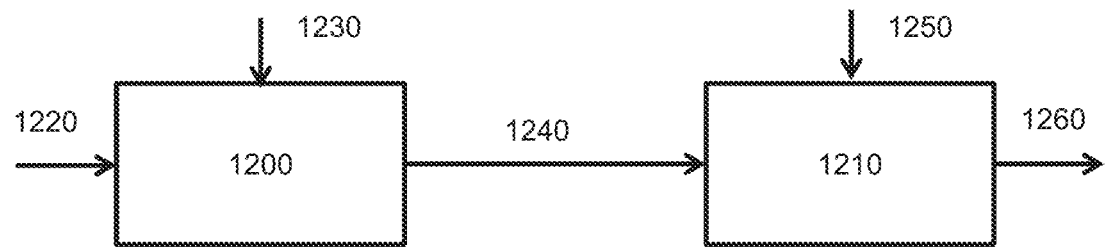
FIG. 12 depicts a high-level flow of determining a patterning process parameter from measured radiation.

Referring to FIG. 12, a method of determining an overlay value for a target having one or more physical instances of a unit cell capable of being geometrically symmetric. This method involves two processes 1200 and 1210. Process 1200 involves obtaining a measurement of the target having the one or more physical instances of the unit cell. Process 1210 involves determining an overlay value for the measured target based on the measurement of the target from process 1200.

Process 1200 takes an input the target 1220 to be measured including one or more physical instances of a unit cell as described herein capable of being geometrically symmetry. In an embodiment, a substrate with one or more instances of the target is provided to a metrology apparatus, such as the metrology apparatus of FIG. 7.

Optionally, process 1200 takes as input a particular measurement strategy 1230 specified for the target. In an embodiment, the measurement strategy can specify a value of one or more measurement parameters, such as one or more selected from: measurement beam wavelength, measurement beam polarization, measurement beam dose, and/or a number of optical characteristic readings taken by a detector sensor of the metrology apparatus of a particular one illumination of the target. In an embodiment, the measurement strategy can comprises a plurality of measurement strategies, each specifying a value of one or more measurement parameters. The measurement strategy can be used to measure the target.

Process 1200 then measures the target using a metrology apparatus according to the optional measurement strategy. In an embodiment, the metrology apparatus obtains a pupil representation of the redirected radiation. In an embodiment, the metrology apparatus can produce a pupil representation such as pupil image 1030 (if, for example, the target has no error in overlay) or pupil image 1060 (if, for example, the target has an error in overlay). Thus, in an embodiment, the process 1200 outputs optical information 1240 regarding the redirected radiation from the target, such as a pupil representation of the radiation.

Process 1210 then receives the optical information 1240 and processes the optical information to determine an overlay value 1260 for the target. In an embodiment, the process 1210 receives as input the weightings 1250 determined from the method of FIG. 11, which then are combined with one or more optical characteristic values (e.g., intensities) obtained or derived from the optical information 1240.

In an embodiment, the process 1210 (or process 1200) can process the optical information to derive a raw overlay signal from the optical information. In an embodiment, the raw overlay signal comprises a differential of the optical information, i.e., a difference in optical characteristic values between symmetric pixels across an axis or point of symmetry. In an embodiment, the derived pupil image 1035 (if, for example, the target has no error in overlay) or derived pupil image 1065 (if, for example, the target has an error in overlay) can be obtained.

In an embodiment, the weightings and optical information with respect to radiation redirected by the target (e.g., the optical information from process 1200 or a processed version of the optical information from process 1200 such as the raw overlay signal) are combined to determine the overlay value. In an embodiment, the use of a combination of redirected measurement beam intensities linearly combined with associated weightings can lead to a quick determination of overlay. For example, in an embodiment, the overlay value can be derived using equation (4) wherein the overlay value M is calculated as the weighted combination of signal components $S_i$ from the raw overlay signal using respective weights w for each of the signal components $S_i$.

In an embodiment, the optical information collected from process 1200 can be used additionally to derive one or more target related parameters other than overlay. For example, the optical information collected from process 1200 can be used in a reconstruction process to derive any one or more geometric profile parameters of the target, such as CD, sidewall angle, bottom floor tilt, etc. So, in an embodiment, a same set of optical information collected from a target, such as an in-die after-etch target, can be used to determine overlay, CD and/or one or more other geometric profile parameters of the target (such as a device structure).

While, as noted above, focus has been on intensity, in an embodiment, the optical characteristic can be reflectivity, the radiation can be polarized and the measurements can be cross-polarization measurements. For example, a target exposed to a certain linear polarization can be measured with that polarization or at a different polarization. So, for symmetric pixels $p_i$ and $p_i'$ (where the apostrophe denotes the symmetric location), then reflectivity R for those pixels can be measured as follows:

$$\bar{R}_i = \begin{bmatrix} R_{ss} & R_{sp} \\ R_{ps} & R_{pp} \end{bmatrix} \quad (4)$$

$$\bar{R}_i' = \begin{bmatrix} R'_{ss} & R'_{sp} \\ R'_{ps} & R'_{pp} \end{bmatrix} \quad (5)$$

wherein s denotes s polarization and p denotes p polarization. Thus, the reflectivity $R_{ss}$ corresponds to reflectivity R of s polarized radiation measured when the target was illuminated using s polarization, reflectivity $R_{sp}$ corresponds to reflectivity R of s polarized radiation measured when the target was illuminated using p polarization, and so on. Moreover, these measurements can be taken at different wavelengths. And, it has been discovered that, in certain embodiments, the overlay for a symmetric unit cell that changes its symmetry in response to overlay change can be found and determined from the congruents $R_{ps}$ and $R_{sp}$.

Further, non-linearity can arise from overlay and/or from other parameters. As discussed above, certain non-linearity can be addressed through appropriate selection of weightings, e.g., by deriving the weightings using a Hessian matrix and/or third order derivatives. In an embodiment, the non-linearity can be addressed by using a non-linear solution to derive the overlay from the measured optical information of redirected radiation from a target.

In an embodiment, the overlay can be determined through using the reconstruction engine as described above used to derive the nominal profile. For example, a non-linear solver working from a model based on the derived nominal profile and/or a derived nominal profile model can be used to derive a simulated version of the optical information expected from redirected radiation from a target of interest, which can be compared to the measured optical information of the target of interest. As noted above, the target of interest comprises one or more physical instances of a unit cell that can be symmetric and that changes its symmetry when subject to overlay. Then, if there is not agreement within a certain threshold, a geometric profile parameter (e.g., overlay) can be varied and the simulated version of the optical information re-computed and compared to the measured optical information until there is agreement within a threshold. Similarly, measured optical information of a target of interest can be compared against a library of the optical information expected from redirected radiation from the target of interest (which library would typically be derived using a non-linear solver). Then, if there is not agreement within a certain threshold, a geometric profile parameter (e.g., overlay) can be varied and the library can be consulted again for a simulated version of the optical information which is compared to the measured optical information until there is agreement within a threshold.

In an embodiment, the use of the reconstruction engine with the measured optical information from a target of interest uses measured optical information from which a symmetric distribution of radiation has been removed as described above, e.g., by subtracting from the optical characteristic value at each pixel the optical characteristic value at a pixel symmetrically located across a point or axis of symmetry. Thus, the optical information relates to substantially only the asymmetric distribution of radiation. Similarly, the simulated or library version of the optical information relates to substantially only the asymmetric distribution of radiation. This will facilitate the speed of calculation and/or comparison as a significant portion of optical information won't need to be calculated or evaluated since it will eliminate through the differencing.

In a further embodiment of a non-linear solution, the expansion of equation (3) can be solved with a non-linear solver to derive $\Delta x_{ov}$. In particular, the values of (a–a'), (b–b'), (c–c'), etc. (as applicable) in equation (3) can be determined as part of the determination of the derived nominal profile and/or the derived nominal profile model of a unit cell of interest. For example, once the derived nominal profile has been determined as part of the non-linear reconstruction, simulated or library optical information for a pupil corresponding to the derived nominal profile (e.g., corresponding to a perturbation of the derived nominal profile for a particular change in overlay (e.g., $\Delta x_{ov}$)) can be obtained and then the values of a, b, c, etc. (as applicable) can be determined for each pixel in the pupil with a non-linear solver that, e.g., iterates through solutions (e.g., responsive to one or more perturbations in overlay (e.g., $\Delta x_{ov}$)) in order to minimize the residual. The result is a vector of a values for the pupil (each a value corresponding to a pixel of the pupil), a vector of b values for the pupil (each b value corresponding to a pixel of the pupil), a vector of c values for the pupil (each a value corresponding to a pixel of the pupil), and so on as applicable. These vectors can then be combined with a vector of $S_i$ values determined from a measured pupil of a target having the unit cell of interest. A non-linear solver that, e.g., iterates through solutions in order to minimize the residual, can take these input vectors and then solve for the overlay $\Delta x_{ov}$.

While the discussion above has focused on using a model that models the physical profile of the unit cell, in an embodiment, the weightings can be derived using a data driven technique that does not require physical profile modelling or can be derived with a data driven technique that supplements physical profile modeling. So, in an embodiment, the data driven technique can advantageously not require a physical profile model; this can be useful, for example, for limiting the sharing of confidential information because the physical profile modeling starts with, and determines, details regarding the unit cell (and thus the target) which can be sensitive information if the unit cell is a device pattern structure. In an embodiment, the data driven technique can be enable relatively quick determination of, for example, the weights as discussed above to translate measured optical information (e.g., pupil intensity) into a patterning process parameter (e.g., overlay). In an embodiment, the data driven technique enables determination of the patterning process parameter in an early stage since as discussed below the data technique driven may need only measured data and an associated reference.

So, in an embodiment, the data driven technique involves processing data measured ("get" data) from one or more substrates having physical instances of the unit cell of interest patterned thereon as one or more targets, with one or more certain set values of the patterning process parameter (e.g., overlay) of interest. This combination of "set" intentional values of a certain patterning process parameter (e.g., overlay) to create patterns along with data measured from those patterns ("get" data) is referred to as a "set-get" process. For example, an overlay of a particular amount of the physical instance of unit cell is created as part of the patterning process and then the target having the physical instance of the unit cell is measured to obtain, e.g., a pupil image thereof (i.e., "get" data). In an embodiment, a plurality of substrates can be patterned and measured in this manner. In an embodiment, a plurality of different set values of overlay are created, which different values of overlay can be on one substrate, can be across different substrates, etc. In an embodiment, each substrate will have a plurality of target instances measured, yielding, e.g., a plurality of pupil images. In an embodiment, the overlay can be created by inducing a magnification change from the design magnification between patterning different parts of the physical instance of the unit cell. In an embodiment, the overlay can be created by providing an intentional translation from the design positioning between patterning different parts of the physical instance of the unit cell. Thus, the result is a deliberate applied overlay in a target that is, e.g., induced by the lithographic apparatus.

In an embodiment, in general, there is obtained measurement data and associated reference values. So, in an embodiment, deliberate overlay need not be provided if there are different overlays but those overlays are determined by another means (e.g., from a scanning electron microscope). In an embodiment, critical dimension uniformity substrates with corresponding reference data (e.g. coming from a CD-SEM) can be used as the input data. With the measured data and the reference values, the data-driven approach can find, as discussed herein, weights such that inferred overlay values resemble the reference values. So, while the discussion of the data-driven technique will focus on measured optical information and pupil representations obtained at intentionally set overlay value, they can be generally applied to more general measurement data and associated reference values (whether measured or intentionally set).

Further, while the techniques here relate to a particular overlay (e.g., an overlay in the X-direction), it will be appreciated that the techniques here can be repeated for different overlays (e.g., an overlay in the Y-direction, overlay between structures in different layers, etc.) using corresponding measurement data and reference values. Thus, different weights sets can be determined for different overlays.

Figure 13:
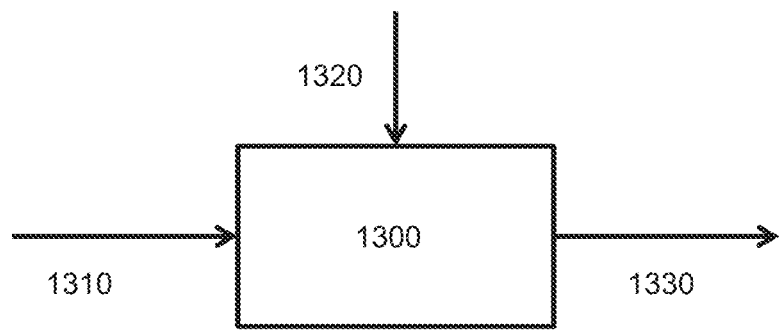
FIG. 13 depicts a high-level flow of an embodiment of a data driven technique.

So, referring to FIG. 13, a high-level flow of an embodiment of a data driven technique is depicted. At 1300, a calculation is performed to derive the weights as discussed above to translate measured optical information (e.g., pupil intensity) into a patterning process parameter (e.g., overlay). In particular, the calculation uses several inputs. One of the inputs is the set values 1320 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1310 for those instances of the target at different set values. In an embodiment, the optical information 1310 is a plurality of pupil representations, each corresponding to an instance of the target. Then, inputs 1310 and 1320 are processed in a data driven technique to arrive at the weights 1330. Examples of such a data driven technique are described hereafter.

In an embodiment, an example of a data driven technique to find a vector of the weights $\underline{w}$ is to minimize the following objective or merit function to arrive at the weights $\underline{w}$:

$$\arg\min_{\underline{w},c} \Sigma_{i=1}^{D} \|P_i^T \underline{w} - \underline{s}_i - \underline{1} c_i\|^2 \qquad (6)$$

wherein $\underline{w}$ is a vector of the weights for combination with values of a measured optical characteristic (e.g., intensity) to determine a patterning process parameter (e.g., overlay), each weight corresponding to a pixel value of the pupil, $P_i$ is a matrix with each column containing the pixel values of the measured optical characteristic from a measured pupil of an instance of a target obtained from a substrate i patterned so as to obtain a particular set value of the patterning process parameter (which matrix is then transposed so that the columns becomes the pixels of the pupil, the rows become the one or more instances of the target on the substrate, and the values in the matrix are the values of measured optical characteristic at the respective pixels), $\underline{s}_i$ is a vector containing the corresponding set values of the patterning process parameter for the one or more instances of the target on the one or more substrates i, each set value corresponding to a patterning process parameter value, $\underline{1}$ is a unit vector of the size of the number of set values, and $c_i$ is an offset difference between the set-values of the patterning process parameter and inferred values of the patterning process parameter ($P_i^T \underline{w}$) for each substrate, and D is the number of substrates measured. The matrix $P_i$ can be combination of different results for each instance of the target. For example, a target can be measured with different wavelengths, different polarizations, etc. So, these results can be concatenated to each column so, for example, a single column can have values for the pixels of a pupil a target measured with a first wavelength and a first polarization, which are followed by values in the column for pixels of a pupil of the target measured with a second different wavelength or followed by values in the column for pixels of a pupil of the target measured with a second different polarization (and which can then be followed by further values at one or more different polarizations and/or wavelengths).

So, in effect, this function finds the weight vector $\underline{w}$, such that the inferred values $P_i^T \underline{w}$ for each substrate i looks as similar as possible (in a L2 regularization norm sense) as the set-values $\underline{s_i}$ apart from an offset $c_i$. In principle, the optimal weights and offsets can be computed by a matrix inversion. Since the pixel values of the measured optical characteristic are taken with one or more particular metrology apparatuses, the obtained weights can be normalized by calibration data to reduce the impact of the particular metrology apparatus itself on the results.

Instead of or in addition to finding the weights as described above using an objective or merit function as the data driven technique, the data driven technique can use a machine learning algorithm, like a neural network, or a non-linear method to determine the weights based on measured pupils of targets with an intentionally provided difference in the patterning process parameter (e.g., overlay) of interest.

In an embodiment, after the training (i.e., using the objective or merit function or the machine learning algorithm), the weights can checked using other data. There is a chance that the training results in an overfit; the data driven approach "just" fits the data to the set values. Therefore, a cross validation is done. New data with known set values are used to check the weights. This new data can also be a subset of the substrates at hand. So, in an embodiment, the training is done on a subset of substrates, and the validation is done on another (disjunct) subset of substrates.

Figure 14:
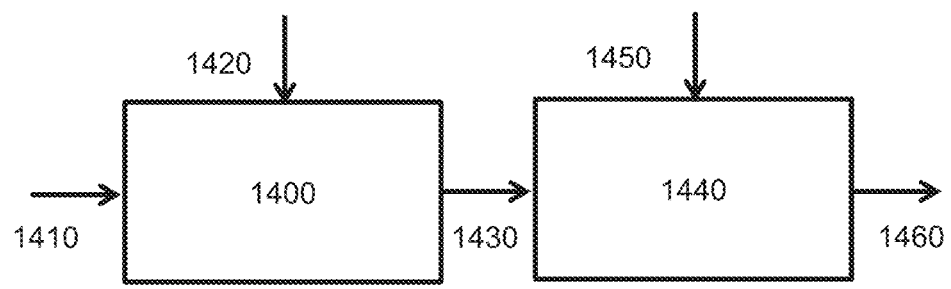
FIG. 14 depicts a high-level flow of an embodiment of a data driven technique in combination with a physical geometric model.

FIG. 14 depicts a high-level flow of an embodiment of a data driven technique in combination with a physical geometric model. In this embodiment, a data driven technique as described in relation to FIG. 13 can be used to derive weights, which are used to tune a physical geometric model (e.g., by using the Hessian to obtain better model nominal values, by changing the model nominal values, etc.) such that weights from physical geometric model (e.g., the (Moore-Penrose pseudo inverse of the) Jacobian of the physical geometric model) are the same or similar (e.g., in value, statistically, etc.) to the weights determined by the data driven technique. Thus, in an embodiment, a (scaled) weight vector $\underline{w}$ can be used to fine-tune the physical geometric model such that the physical geometric model is tuned so that the (Moore-Penrose pseudo inverse of) the Jacobian is similar to the (scaled) weight vector $\underline{w}$.

So, in an embodiment, at 1400, a data driven technique (examples of which are described above) is performed to derive the weights as discussed above. The calculation uses several inputs. One of the inputs is the set values 1420 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1410 for those instances of the target at different set values. In an embodiment, the optical information 1410 is a plurality of pupil representations, each corresponding to an instance of the target. Then, inputs 1410 and 1420 are processed in a data driven technique to arrive at the weights 1430.

The weights 1430 are input to a process 1440 to fine-tune a physical geometric model using the weights 1430. The process 1440 obtains a physical profile 1450 for the unit cell (which the process 1440 uses to derive a physical profile model) or obtains a physical profile model 1450 for the unit cell (which the process 1440 uses). In an embodiment, the physical profile is the derived nominal profile and/or the derived nominal profile model of a unit cell as discussed above.

The process 1440 uses the physical geometric model to derive weights that correspond to weights 1430. Those weights are then compared to the weights 1430. The comparison can involve a matching of magnitudes, a statistical analysis, a fitting evaluation, etc. If there is a significant difference (e.g., by evaluation of the comparison against a threshold), one or more parameters of the physical profile can be tuned. For example, one or more physical profile parameters (e.g., CD, sidewall angle, material heights, etc.) can be tuned so that the results of the comparison come closer than or equal to, e.g., a certain threshold. In an embodiment, the Hessian can be used to do this fine-tuning, or can be done using a non-linear solver (including one or more forward calls (e.g., a Maxwell solver)). The tuning and comparison can be iterated until the threshold is met or crossed. Then, the tuned physical geometric model can output updated weights 1460 for use in combining with measured optical information of a target of interest to derive a patterning process parameter value.

FIG. 15 depicts a high-level flow of a further embodiment of a data driven technique in combination with a physical geometric model. When a physical geometric model behaves similarly as measured data, the physical geometric model can be used to predict the impact of process variations. So, in an embodiment, the Hessian of the physical geometric model can be used to tune the weights such that the weights become (more) orthogonal to process variations that were not in the data used in the data driven technique to obtain the weights used to tune the physical geometric model.

This approach of using the Hessian to tune the weights can also be done without the data driven technique. That is, this technique to use the Hessian to update the weights can be done with a physical geometric model approach described in association with FIG. 11. In this case, for example, the weights can be tuned such that the weights become (more) orthogonal to process variations that were not in the data used to obtain the derived nominal profile and/or the derived nominal profile model of a unit cell as discussed above. Through such tuning, the weights become more robust to process variations not observed in measured data used to create the physical geometric model.

So, in an embodiment, at 1500, a data driven technique (examples of which are described above) is performed to derive the weights as discussed above. The calculation uses several inputs. One of the inputs is the set values 1510 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1505 for those instances of the target at different set values. In an embodiment, the optical information 1505 is a plurality of pupil representations, each corresponding to an instance of the target. Then, inputs 1505 and 1510 are processed in a data driven technique to arrive at the weights 1515.

The weights 1515 are input to a process 1520 to fine-tune a physical geometric model using the weights 1515. The process 1520 obtains a physical profile 1525 for the unit cell (which the process 1520 uses to derive a physical profile model) or obtains a physical profile model 1525 for the unit cell (which the process 1520 uses). In an embodiment, the physical profile is the derived nominal profile and/or the derived nominal profile model of a unit cell as discussed above.

The process 1520 uses the physical geometric model to derive weights that correspond to weights 1515. Those weights are then compared to the weights 1515. The comparison can involve a matching of magnitudes, a statistical analysis, a fitting evaluation, etc. If there is a significant difference (e.g., by evaluation of the comparison against a threshold), one or more parameters of the physical profile can be tuned. For example, one or more physical profile parameters (e.g., CD, sidewall angle, material heights, etc.) can be tuned so that the results of the comparison come closer than or equal to, e.g., a certain threshold. In an embodiment, the Hessian can be used to do this fine-tuning, or can be done using a non-linear solver (including one or more forward calls (e.g., a Maxwell solver)). The tuning and comparison can be iterated until the threshold is met or crossed.

But, as will be appreciated, a patterning process can vary during execution and differently for different executions of the patterning process. Thus, data obtained for the data driven technique doesn't account for all the possible patterning process variations. But, when the tuning of the physical geometric model has made it so that behaves similarly as measured data, the physical geometric model can be used to predict the impact of process variations and adjust the weights accordingly.

So, in an embodiment, the tuned physical geometric model 1530 is used to compute the Hessian of the tuned physical geometric model at 1535. The Hessian 1540 is then used to tune the weights at 1545 such that the weights become (more) orthogonal (i.e., robust) to process variations that were not in the data used in the data driven technique to obtain the weights used to tune the physical geometric model. In other words, the weights are tuned to be more likely to yield an accurate result when combined with measurement data from a substrate even when the substrate is subject to process variation.

A non-limiting example of how the Hessian can be used to fine-tune the weights is described here in the context of overlay; a different patterning process parameter could be used as appropriate. In this example, it is assumed only one overlay type is evaluated (e.g., overlay in the X direction). Fine-tuning with multiple overlay types is also possible.

In this embodiment of using the Hessian to fine-tune the weights, an overlay response is estimated from data measured from one or more set-get substrates by applying a single value decomposition to the data. It is assumed that an eigenvector $\underline{d}$ (which has length 1) corresponds to the overlay response. Then the following equation is solved to find vector $\underline{\Delta p}$:

$$\arg\min_{\underline{\Delta p}} \left\| \underline{d} - \frac{\underline{J} + H\underline{\Delta p}}{\|\underline{J} + H\underline{\Delta p}\|} \right\| \qquad (7)$$

wherein $\underline{J}$ is the Jacobian with respect to the overlay parameter, and the Hessian H is a matrix where the columns contain the partial derivatives with respect to a process variation (e.g., a variation in CD, material height, etc.) and the overlay parameter (both the Jacobian and the Hessian are obtained from the model as described above). The determined vector $\underline{\Delta p}$ then corresponds to the delta parameters to be applied to the non-overlay parameters in the model to obtain an updated (e.g., better) model.

To make the weights robust to process variations (i.e. orthogonal to the process variations), the following technique can be used. A pupil $\underline{I}$ can be defined by the following second order Taylor expansion:

$$\underline{I} = \underline{J}o + H\underline{\Delta p}o \qquad (8)$$

where $\underline{J}$ is the Jacobian with respect to the overlay parameter, and H is a matrix where the columns contain the partial derivatives with respect to a process variation (e.g., a variation in CD, material height, etc.) and the overlay parameter. The vector $\underline{\Delta p}$ contains the corresponding process variations. Thus, for a given structure and for a given process variation instance $\underline{\Delta p}$ with an overlay value o, the pupil equals (approximately) $\underline{I}$. As will be appreciated, the above formulation can be extended to more overlay parameters by adding these contributions as well. Moreover, this formulation is an approximation because the higher orders in the Taylor expansion are neglected.

Now, if the impact of the process variations is small, the weights are computed using the Penrose-Moore inverse of the Jacobian $\underline{J}$. In the case of only one overlay parameter, the weights equal to $$\underline{w} = \frac{\underline{J}}{\|\underline{J}\|^2}.$$

And indeed, the weighted average (inner product) with the pupil results in the overlay value o ($\Delta p=0$), i.e., $$\langle \underline{I}, \underline{w} \rangle = \langle \underline{J}o, \underline{w} \rangle = \frac{o}{\|\underline{J}\|^2} \langle \underline{J}, \underline{J} \rangle = o \qquad (9)$$

However, when the process variations have a large impact, the overlay response changes:

$$\underline{I} = (\underline{J} + H\underline{\Delta p})o = \underline{J}o \qquad (10)$$

To make the weights robust to these variations, $$H\underline{w} = \underline{0} \qquad (11)$$

This can be achieved by taking the weights $\underline{w}$ equal to the first row of the pseudo inverse of the matrix $[\underline{J}\ H]$. Or in other words, the Hessian matrix H is concatenated to the Jacobian before the inversion. In this way, the weights become orthogonal to the process variations (but at some cost of precision).

Thus, from tuning 1545, tuned weights 1550 are output for use in combining with measured optical information of a target of interest to derive a patterning process parameter value.

FIG. 16 depicts a high-level flow of a further embodiment of a data driven technique in combination with a physical geometric model. In this embodiment, the data input to the data driven technique is extended by including synthetic optical information (e.g., pupil representations) that contains process variations for the patterning process (e.g. the patterning process variation can be obtained from CD measurements). The synthetic optical information alone or in combination with the measured optical information can be used to find new weights using the data driven technique.

So, in an embodiment, at 1500, a data driven technique (examples of which are described above) is performed to derive the weights as discussed above. The calculation uses several inputs. One of the inputs is the set values 1510 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1505 for those instances of the target at different set values. In an embodiment, the optical information 1505 is a plurality of pupil representations, each corresponding to an instance of the target. Then, inputs 1505 and 1510 are processed in a data driven technique to arrive at the weights 1515.

The weights 1515 are input to a process 1520 to fine-tune a physical geometric model using the weights 1515. The process 1520 obtains a physical profile 1525 for the unit cell (which the process 1520 uses to derive a physical profile model) or a physical profile model 1525 for the unit cell (which the process 1520 uses). In an embodiment, the physical profile is the derived nominal profile and/or the derived nominal profile model of a unit cell as discussed above.

The process 1520 uses the physical geometric model to derive weights that correspond to weights 1515. Those weights are then compared to the weights 1515. The comparison can involve a matching of magnitudes, a statistical analysis, a fitting evaluation, etc. If there is a significant difference (e.g., by evaluation of the comparison against a threshold), one or more parameters of the physical profile can be tuned. For example, one or more physical profile parameters (e.g., CD, sidewall angle, material heights, etc.) can be tuned so that the results of the comparison come closer than or equal to, e.g., a certain threshold. The tuning and comparison can be iterated until the threshold is met or crossed.

So, in an embodiment, the tuned physical geometric model 1530 is used to compute the Hessian of the tuned physical geometric model at 1535. The Hessian 1600 is then used to generate at 1610 synthetic optical information (e.g., one or more pupil representations). Synthetic optical information is simulated optical information. The synthetic optical information is intended to mimic one or more expected process variations in the patterning process. In an embodiment, data 1620 regarding one or more process variations in the patterning process can be used in combination with the Hessian 1600 to derive the synthetic optical information. In an embodiment, a synthetic pupil $\underline{I}$ can be generated by substituting different overlay values o and different parameter variations $\underline{\Delta p}$ in the equation (8) above, wherein the weights correspond to $$\underline{w} = \frac{\underline{J}}{\|\underline{J}\|^2}.$$

While equation (8) described above is directed to a single overlay parameter, the technique can be extended to more overlay parameters by adding those contributions as well. Furthermore, the technique using equation (8) is an approximation, because the higher orders in the Taylor expansion are neglected. The data 1620 can comprise, for example, information that describes the kind and extent of a process variation (e.g., an indication that overlay, CD, etc. can vary by a certain percentage). The data 1620 can be obtained by a measurement in the patterning process, e.g., overlay, CD, etc. measurement. The data 1620 is thus used with the Hessian 1600 to generate simulated optical information 1630 that includes an expected process variation. The synthetic optical information 1630 can also include one or more associated estimated set values associated with the synthetic optical information 1630. The synthetic optical information 1630 (and any associated set values) is then input to the data driven technique 1500 for analysis alone or in combination with the measured optical information, to find new weights using the data driven technique.

Figure 17:
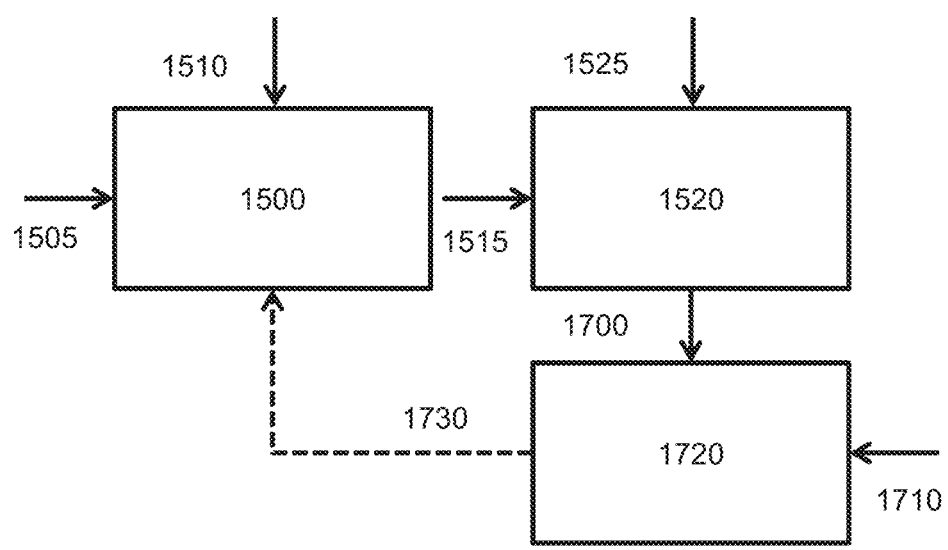
FIG. 17 depicts a high-level flow of an embodiment of a data driven technique in combination with a physical geometric model.

FIG. 17 depicts a high-level flow of a further embodiment of a data driven technique in combination with a physical geometric model. This embodiment is similar to the embodiment of FIG. 16 except that instead of computing a Hessian a forward call is made to a non-linear solver (e.g., a Maxwell solver) for every process variation to obtain the synthetic optical information.

So, in an embodiment, at 1500, a data driven technique (examples of which are described above) is performed to derive the weights as discussed above. The calculation uses several inputs. One of the inputs is the set values 1510 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1505 for those instances of the target at different set values. In an embodiment, the optical information 1505 is a plurality of pupil representations, each corresponding to an instance of the target. Then, inputs 1505 and 1510 are processed in a data driven technique to arrive at the weights 1515.

The weights 1515 are input to a process 1520 to fine-tune a physical geometric model using the weights 1515. The process 1520 obtains a physical profile 1525 for the unit cell (which the process 1520 uses to derive a physical profile model) or a physical profile model 1525 for the unit cell (which the process 1520 uses). In an embodiment, the physical profile is the derived nominal profile and/or the derived nominal profile model of a unit cell as discussed above.

The process 1520 uses the physical geometric model to derive weights that correspond to weights 1515. Those weights are then compared to the weights 1515. The comparison can involve a matching of magnitudes, a statistical analysis, a fitting evaluation, etc. If there is a significant difference (e.g., by evaluation of the comparison against a threshold), one or more parameters of the physical profile can be tuned. For example, one or more physical profile parameters (e.g., overlay, CD, sidewall angle, etc.) can be tuned so that the results of the comparison come closer than or equal to, e.g., a certain threshold. The tuning and comparison can be iterated until the threshold is met or crossed.

So, in an embodiment, the tuned physical geometric model 1700 is used to compute at 1720 synthetic optical information like as discussed above. Like as discussed above, data 1710 regarding one or more process variations in the patterning process can be used in combination with the tuned physical geometric model 1700 to derive the synthetic optical information. For example, the data 1710 can comprise information that describes the kind and extent of a process variation (e.g., an indication that overlay, CD, etc. can vary by a certain percentage). The data 1710 can be obtained by a measurement in the patterning process, e.g., overlay, CD, etc. measurement. As noted above, the process at 1720 can use a forward call to a non-linear solver (e.g., a Maxwell solver) for the process variation to obtain the synthetic optical information. The data 1710 is thus used with the tuned physical geometric model 1700 to generate simulated optical information 1730 that includes an expected process variation. The synthetic optical information 1730 can also include one or more associated estimated set values associated with the synthetic optical information 1730. The synthetic optical information 1730 (and any associated set values) is then input to the data driven technique 1500 for analysis alone or in combination with the measured optical information, to find new weights using the data driven technique.

In FIGS. 10A-10C, a relatively simple example of a unit cell was presented in which an overlay in essentially only one direction caused a change in the symmetry of the unit cell. In particular, in the unit cell of FIGS. 10A-10C, an overlay change in the X direction resulted in a change in the symmetry/asymmetry of the unit cell, while an overlay change in the Y direction does not result in a change in the symmetry of the unit cell. This is a consequence of the unit cell of FIGS. 10A-10C having two structures 1000, 1005 which are configured in a particular geometric way such that an overlay in essentially only one direction caused a change in the symmetry of the unit cell. Of course, this can be designed in this manner by appropriate selection of structures. However, it could be that an existing structure, such as a device structure, can be identified that has a particular geometry such that an overlay in essentially only one direction causes a change in the symmetry of the unit cell. So, various unit cells can be chosen or designed that enable determination of an overlay in essentially only one direction (which need not be in the X direction).

However, advantageously, a unit cell can be identified or designed that is configured so that a change in the symmetry of the unit cell results for two or more different overlays. In an embodiment, the different overlays can be in different directions. Specifically, in an embodiment, a first overlay can be in the X direction, while a second overlay can be in the Y direction. In an embodiment, the different overlays can each be between a different combination of structures or parts of the unit cell. In an embodiment, those structures can be in a same layer and/or in different layers of the target. Specifically, in an embodiment, a first overlay can be between a first structure and a second structure of the unit cell and a second overlay can be between the first structure (or second structure) and a third structure of the unit cell or between a third structure and a fourth structure of the unit cell. In this case, the first overlay and second overlay can be in the same direction. Naturally, there can be a combination of different overlays in different directions and different overlays from combinations of structures of the unit cell. For example, a first overlay can be in the X direction for a first structure in a first layer and a second structure in a second lower layer and a second overlay can be in the Y direction for the first structure in the first layer and a third structure in the a third layer lower than the second layer. Thus, numerous combinations of overlay can be determined through appropriate identification or design of the unit cell (and thus the target).

Moreover, as will be appreciated, a determination of an overlay in the X direction and the Y direction can enable through appropriate combination determine a total overlay (in X and Y). Similarly, to enable the determination of total overlay for multiple different structures between which overlay can occur, the overlay for each of those structures needs to be determined. So, as an example, for a unit cell that has 4 distinct structures in 4 layers between which overlay can occur (with one of the layers being a reference layer), then 6 overlays (X and Y for each layer) could be determined to enable determination of the total overlay for the unit cell. Of course, a sub-combination could be determined as desired to arrive at one or more different overlays of interest among the 4 layers.

Figure 18:
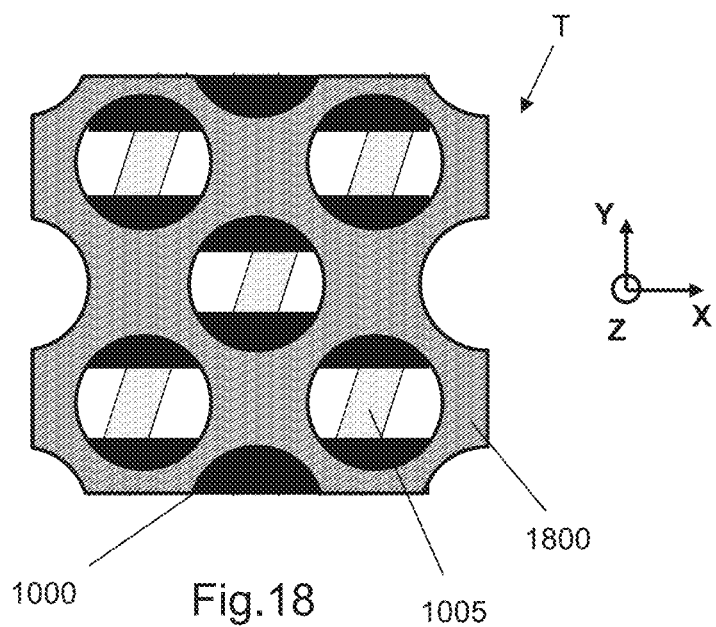
FIG. 18 schematically depicts an embodiment of a multiple overlay unit cell of a target.

FIG. 18 depicts an example embodiment of a multiple overlay unit cell of a target. Like the unit cells of FIGS. 10A-10C, this unit cell comprises a first structure 1000 and a second structure 1005. Additionally, this unit cell has a third structure 1800 that is in this embodiment in a layer above, in the Z direction, the first and second structures 1000, 1005. In this embodiment, asymmetry of this unit cell can be created by one or more different overlays. For example, a relative shift between the structure 1005 and the structure 1800 in the X direction can yield an overlay in the X direction which causes asymmetry. As another example, a relative shift between the structure 1005 and the structure 1000 in the Y direction can yield an overlay in the Y direction which causes asymmetry. As a further example, a relative shift between the structure 1000 and the structure 1800 in the Y direction can yield a further overlay in the Y direction which causes asymmetry.

Figure 19:
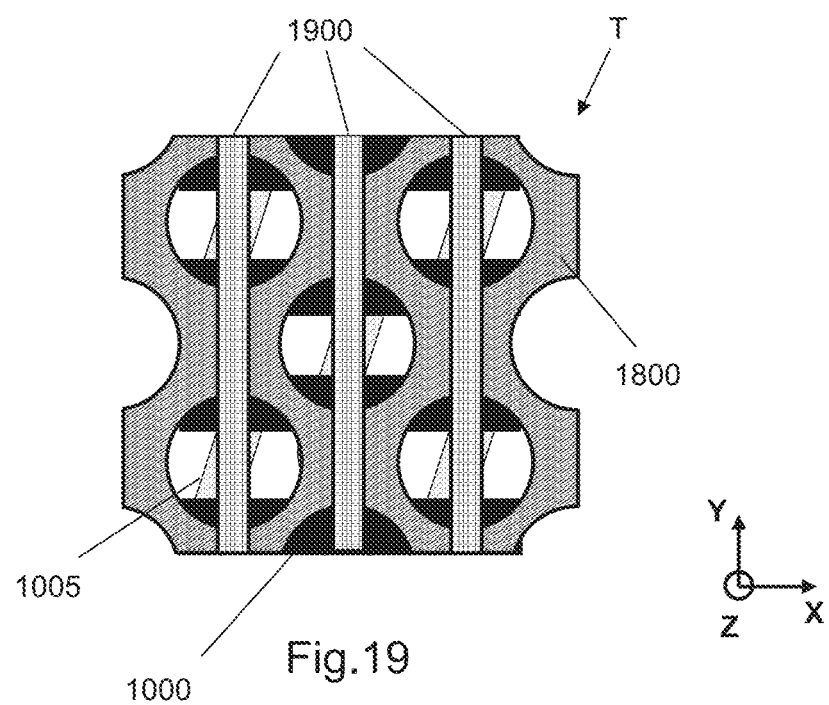
FIG. 19 schematically depicts an embodiment of a multiple overlay unit cell of a target.

FIG. 19 depicts a further example embodiment of a multiple overlay unit cell of a target. Like the unit cells of FIGS. 10A-10C, this unit cell comprises a first structure 1000 and a second structure 1005. Additionally, like the unit cell of FIG. 18, this unit cell has a third structure 1800 that is in this embodiment in a layer above, in the Z direction, the first and second structures 1000, 1005. Further, this unit cell has a fourth structure 1900 that is in this embodiment in a layer above, in the Z direction, the first, second and third structures 1000, 1005, 1800. Like the unit cell of FIG. 18, in this embodiment, asymmetry of this unit cell can be created by one or more different overlays. For example, a relative shift between the structure 1005 and the structure 1800 in the X direction can yield an overlay in the X direction which causes asymmetry. As another example, a relative shift between the structure 1005 and the structure 1900 in the X direction can yield an overlay in the X direction which causes asymmetry. As another example, a relative shift between the structure 1005 and the structure 1000 in the Y direction can yield an overlay in the Y direction which causes asymmetry. As a further example, a relative shift between the structure 1000 and the structure 1800 in the Y direction can yield a further overlay in the Y direction which causes asymmetry.

Thus, in an embodiment, measurement of an illuminated physical instance of the unit cell of FIG. 18 or of FIG. 19 will yield optical information that could potentially include multiple different overlays if there are in fact multiple different overlays. For example, referring to FIG. 18, if the symmetry of the unit cell of FIG. 18 represents zero overlay and there is a shift in the X and Y of the structure 1005 (e.g., a shift in direction that is not 0, 90, 180 or 270 degrees) from its zero overlay position relative to its overlying structures, that shift would cause an asymmetry due to the relative shift between the structure 1005 and the structure 1800 in the X direction and the relative shift between the structure 1005 and the structure 1000 in the Y direction. So, it would be desirable to determine both the overlay for structure 1005 in the X and Y directions (which combination will yield the total overlay of structure 1005).

As discussed hereafter, a technique is presented that can determine, from the optical characteristic values, a value of a first overlay for the physical instance of the unit cell separately from a second overlay for the physical instance of the unit cell that is also obtainable from the same optical characteristic values, wherein the first overlay is in a different direction than the second overlay (e.g., X direction overlay and Y direction overlay) or between a different combination of parts of the unit cell than the second overlay (e.g., a first overlay between structure 1005 and structure 1800 and a second overlay between structure 1005 and structure 1000 or between structure 1000 and structure 1800, where the first overlay and the second overlay could possibly be in the same direction).

That is, in an embodiment, weights are determined to decouple first overlay information in an optical characteristic value from second (or more) overlay information in the same optical characteristic value. Thus, in an embodiment, by applying specially selected weights, the combination of the weights with optical characteristic values will yield a particular overlay of interest as distinguished from other possible overlay information in the same optical characteristic values. In effect, the weights will feature the overlay of interest and lessen one or more other overlays. Of course, different sets of weights can be constructed for each overlay of interest such that the optical characteristic values can be processed to yield different values for each of the different overlays of interest.

Figure 20:
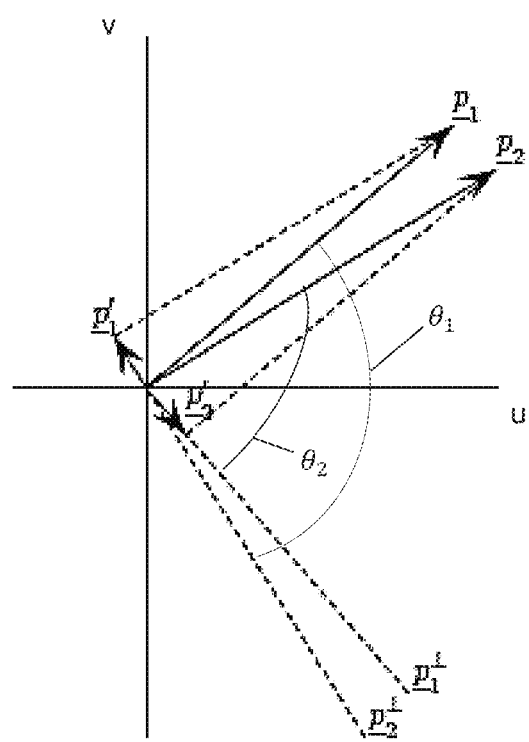
FIG. 20 depicts an example graph of two vectors corresponding to two different overlays.

This technique will be described in respect of the graph of FIG. 20. The graph of FIG. 20 presents a graphical presentation of the technique but in practice the graph need not be constructed as all the processing can be done mathematically without the need to create the graph. Further, the technique is described in respect of the model of FIG. 11. But, models (and associated other techniques) described in respect of other Figures herein could be used.

Further, this example is presented in terms of deriving the linear version of the weights from the model. That is, in an embodiment, the weights are derived from the (Moore-Penrose pseudo inverse of) the Jacobian.

So, in this linear case, to reconstruct a particular parameter such as an overlay in a certain direction, the Jacobian can be inverted. But, how the column of the parameter of interest is correlated to the remaining columns determines how easily it will be to reconstruct this parameter.

So, having, e.g., the nominal profile model for a unit cell of interest (e.g., the unit cell of FIG. 18), at least two vectors can be generated. A first overlay vector $\underline{p}_1$ represents a first overlay of interest (e.g., a X-direction overlay) within the unit cell and a second overlay vector $\underline{p}_2$ represents a second overlay of interest (e.g., a Y-direction overlay). As will be appreciated, further vectors can be created for additional overlays of interest.

Further, for each of the two overlay vectors, one or more pixels of a pupil representation corresponding to an expected measurement of the physical instance of the unit cell are selected. In this embodiment, a pair of pixels is selected for each overlay vector, wherein each pair of pixels comprises symmetrically located pixels as described earlier. Desirably, the pairs of pixels are selected from the asymmetric radiation distribution portion of the pupil representation as discussed above.

Now, the first overlay vector $\underline{p}_1$ corresponds to the response (in this case, asymmetric signal between the pixels creating a pair) in the pairs of pixels to a change in the first overlay of interest for the first overlay vector (leaving all other parameters unchanged, i.e., no change in the second overlay of interest). This response can be generated using the nominal profile model by inducing a change in the first overlay of interest (e.g., 1 nm change) and then calculating the optical response (e.g., intensity) in the pairs of pixels to that change.

Similarly, the second overlay vector $\underline{p}_2$ corresponds to the response (in this case, asymmetric signal between the pixels creating a pair) in the pairs of pixels to a change in the second overlay of interest for the second overlay vector (leaving all other parameters unchanged, i.e., no change in the first overlay of interest). This response can be generated using the nominal profile model by inducing a change in the second overlay of interest (e.g., 1 nm change) and then calculating the optical response (e.g., intensity) in the pairs of pixels.

The resulting vectors are graphed in FIG. 20 wherein the horizontal axis u corresponds to the asymmetric intensity $(I_i-I_i')$ between symmetrically positioned pixels of the first pixel pair and the vertical axis v corresponds to the asymmetric intensity $(I_i-I_i')$ between symmetrically positioned pixels of the second pixel pair. So, FIG. 20 shows two highly correlating vectors $\underline{p}_1$ and $\underline{p}_2$.

So, to decouple and separate the contributions of the first and second overlays of interest to the pixel pairs, the vector $\underline{p}_1$ is back-projected onto a vector $\underline{P}_2^\perp$, which is a vector orthogonal to the vector $\underline{p}_2$, to form vector $p_1'$ and the length of projected vector $p_1'$ is divided by the cosine of the angle $\theta_1$ between vector $\underline{p}_1$ and $\underline{P}_2^\perp$. This vector then helps to isolate the first overlay of interest from the intensity of the pixel pairs (and by extension other pixel pairs in the pupil representation).

Additionally or alternatively, the vector $\underline{p}_2$ is back-projected onto a vector $\underline{P}_1^\perp$, which is a vector orthogonal to the vector $\underline{p}_1$, to form vector $p_2'$ and the length of projected vector $p_2'$ is divided by the cosine of the angle $\theta_2$ between vector $\underline{p}_2$ and $\underline{P}_1^\perp$. This vector then helps to isolate the second overlay of interest from the intensity of the pixels pairs (and by extension other pixel pairs in the pupil representation).

So, referring back to equations (3) and (4), $S_i$ represents the asymmetric intensity $(I_i-I_i')$ between symmetrically positioned pixels of a pixel pair. So, the first overlay vector $\underline{p}_1$ can correspond to the response in a first pixel pair having $S_i$ of $U_0$ and a second pixel pair having $S_i$ of $V_0$ to a change in the first overlay of interest. Similarly, the second overlay vector $\underline{p}_2$ can correspond to the response in those first and second pixel pairs to a change in the second overlay of interest. Accordingly, the vector $p_1'$ and/or the vector $p_2'$ can be constructed; here both are constructed for explanatory purposes. The vector $p_1'$ and the vector $p_2'$ are defined in terms of the intensity u corresponding to the first pixel pair corresponding to $U_0$ and in terms of the intensity v corresponding to the second pixel pair corresponding to $V_0$. So, vector $p_1'$ and vector $p_2'$ can be specified as:

$$p_1'=(u_1',v_1') \quad (12)$$

$$p_2'=(u_2',v_2') \quad (13)$$

So, now in the linear context described above and referring to equation (4), an overlay value of the first overlay of interest can then be defined based on $U_0$, $V_0$, and vectors $p_1'$ and $p_2'$ as follows:

$$OV_{p1}=(u_1'U_0+v_1'V_0)/\cos\theta_1 \quad (14)$$

Additionally or alternatively, an overlay value of the second overlay of interest can then be defined based on $U_0$, $V_0$ and vectors $p_1'$ and $p_2'$ as follows $$OV_{p2}=(u_2'U_0+v_2'V_0)/\cos\theta_2 \quad (15)$$

So, from equation (14), the weights to determine the first overlay of interest are, for respectively $U_0$ and $V_0$, the following:

$$\frac{u_1'}{\cos\theta_1}, \frac{v_1'}{\cos\theta_1} \quad (16)$$

Further, from equation (15), the weights to determine the second overlay of interest are, for respectively $U_0$ and $V_0$, the following:

$$\frac{u_2'}{\cos\theta_2}, \frac{v_2'}{\cos\theta_2} \quad (17)$$

So, as will be appreciated, this can be repeated for all, or substantially all, of the pixel pairs in the pupil representation so as to arrive at a set of weights $w_i$ for the first overlay of interest ($w_i^1$) and/or to arrive at a set of weights $w_i$ for the second overlay of interest ($w_i^2$). One or both of these can then applied to measured optical characteristic values in accordance with equation (4) to arrive at an overlay value for the respective overlay of interest. Of course, one or more further overlays of interest can be evaluated and one or more appropriate weight sets determined for them. As will be appreciated, in an embodiment, the sensitivity (e.g., Jacobian) to all of the different overlays of interest is included in the weights definition for a particular overlay of interest.

So, for example for a unit cell having 4 layers (with one of the layers being a reference layer) wherein a shift in each of the layers in the X and Y directions could cause a change in symmetry (e.g., cause an asymmetry, or cause a further asymmetry, or cause an asymmetric unit cell to become symmetric), then 6 vectors can be created (each being associated with a different pixel pair), the 6 vectors comprising a X-direction overlay vector for each of the layers and a Y-direction overlay vector for each of the layers. There could thus be 6 sets of weights to derive the respective overlays. Of course not all of the weight sets need to be derived if one of the vectors is not of interest (but in an embodiment, the sensitivity (e.g., Jacobian) to all of the different overlays of interest is included in the weights definition for the particular overlay of interest). Any other overlay can then be determined by appropriate mathematical combination of two or more of these overlays.

As will be appreciated, some shifts of a layer in a unit cell would not cause a change in symmetry and so the overlay corresponding to that shift cannot be determined from the unit cell. So, obviously, no vector would be defined for such a shift. So, taking FIG. 18 as an example, three vectors could be defined for that unit cell—one for the X-direction overlay and two for the different Y-direction overlays. So, one sets of weights can be determined that will give the overlay in the X-direction when combined with measured optical characteristic values. Or, a set of weights can be determined that will give one of the overlays in the Y-direction when combined with measured optical characteristic values and/or a set of weights can be determined that will give the other of the overlays in the Y-direction when combined with measured optical characteristic values. Of course, all three sets of weights can be determined or just two.

The discussion above has focused on a target formed by one or more instances of a symmetrical unit cell made up of structures of a device. Such a target can enable, through on-product measurement of radiation redirected by the on-product target, determination of an on-product value of a patterning process parameter. However, as described above, the target need not be made up of only device structures. In other words, a non-product target can be provided whose structures don't exclusively comprise device structures. For example, in an embodiment, a target can be specially created of structures that are not used to form the device but rather are merely used for measurement. Such a target can be provided, e.g., in a scribe lane away from the device (and thus provided in a part of a device patterning pattern away from the device pattern). In an embodiment, the target can be provided in among the device pattern (and thus provided among the features of a device pattern of a patterning device pattern). Where appropriate, a non-product target can comprise one or more device structures and one or more specially created structures that are not used to form the device but rather are merely used for measurement.

A non-product target can be useful if, for example, a patterning process parameter is being determined for a device pattern that cannot present symmetric unit cell instances. As another example, a non-product target can be useful if, for example, a patterning process parameter is being determined for a portion of a device pattern that doesn't have a symmetrical unit cell as described above that can give a measure of that patterning process parameter. For example, there can be cases of a structure for overlay after etch is desired to be determined using the symmetrical unit cell methods described above but has no symmetry. For example, logic circuits or structures have many process layers\steps that are each able to introduce a different overlay component that can break the symmetry of the structure. In the case of logic circuits for example, measurement on the device pattern typically cannot be performed due to the lack of a symmetric unit cell of logic circuit structures.

As a further example, the non-product target can be used in association with a device pattern that can present symmetric unit cell instances (and even if the unit cell can give a measure of all patterning process parameters of interest). This can be, for example, if the device pattern is complex, which can require significant computation time. Further, the device pattern may present potential cross-talk with signals of patterning process parameters not of interest. As an example, the pupil correlations of different overlay components might be so large that it is impossible to separate the different overlay errors.

Thus, a non-product target can be used with a device pattern that has instances of a symmetrical unit cell for a beam spot or with a device pattern that can't present instances of a symmetrical unit for the beam spot. Details of configuration, design, measurement and use of a non-product target are described in detailed in U.S. patent application Ser. No. 15/445,612, filed on Feb. 28, 2017, which is incorporated herein in its entirety by reference.

The measurement accuracy and/or sensitivity of a target (whether a product target or non-product target and irrespective of whether that target has a symmetry that is broken as discussed herein by a certain physical phenomenon represented by a certain parameter (such as overlay)) may vary with respect to one or more attributes of the target itself and/or one or more attributes of the measurement radiation provided onto the target, for example, the wavelength of the radiation, the polarization of the radiation, the intensity distribution (i.e., angular or spatial intensity distribution) of the radiation, and/or the incident angle of a chief ray of the measurement radiation. In an embodiment, the wavelength range of the radiation is limited to one or more wavelengths selected from a range (e.g., selected from the range of about 400 nm to 900 nm). Further, a selection of different polarizations of the radiation beam (e.g., TE polarized radiation, TM polarized radiation, vertical linear polarization, horizontal linear polarization, etc.) may be provided and various illumination distributions and/or angles can be provided using, for example, a plurality of different apertures.

So, to enable such selection and measurement, a metrology recipe can be used that specifies one or more parameters of the measurement using the measurement system. In an embodiment, the term "metrology recipe" includes one or more parameters of the measurement itself, one or more parameters of a pattern of the target measured, or both.

In this context, a pattern of the target measured (also referred to as a "target structure") may be a pattern that is optically measured, e.g., whose diffraction is measured. The target pattern measured may be a pattern specially designed or selected for measurement purposes (such as a non-product target). Multiple copies of a target may be placed on many places across a substrate (e.g., within or near a plurality of dies across the substrate).

In an embodiment, if the metrology recipe comprises one or more parameters of the measurement itself, the one or more parameters of the measurement itself can include one or more parameters relating to a measurement beam and/or measurement apparatus used to make the measurement. For example, if the measurement used in a metrology recipe is a diffraction-based optical measurement, one or more parameters of the measurement itself may include a wavelength of measurement radiation, and/or a polarization of measurement radiation, and/or measurement radiation intensity distribution, and/or an illumination angle (e.g., incident angle, azimuth angle, etc.) relative to the substrate of measurement radiation, and/or the relative orientation relative to a pattern on the substrate of diffracted measurement radiation, and/or a number of measured points or instances of the target, and/or the locations of instances of the target measured on the substrate. The one or more parameters of the measurement itself may include one or more parameters of the metrology apparatus used in the measurement, which can include detector sensitivity, numerical aperture, etc.

In an embodiment, if the metrology recipe comprises one or more parameters of a pattern measured, the one or more parameters of the pattern measured may include one or more geometric characteristics (such as a shape of at least part of the pattern, and/or orientation of at least part of the pattern, and/or a pitch of at least part of the pattern (e.g., pitch of a periodic structure including the pitch of an upper periodic structure in a layer above that of a lower periodic structure and/or the pitch of the lower periodic structure), and/or a size (e.g., CD) of at least part of the pattern (e.g., the CD of a feature of a periodic structure, including that of a feature of the upper periodic structure and/or the lower periodic structure), and/or a segmentation of a feature of the pattern (e.g., a division of a feature of a periodic structure into sub-structures), and/or a length of a periodic structure or of a feature of the periodic structure), and/or a materials property (e.g., refractive index, extinction coefficient, material type, etc.) of at least part of the pattern, and/or an identification of the pattern (e.g., distinguishing a pattern being from another pattern), etc.

A metrology recipe may be expressed in a form like ($r_1$, $r_2$, $r_3$, . . . $r_n$; $t_1$, $t_2$, $t_3$, . . . $t_m$), where $r_i$ are one or more parameters of the measurement and $t_j$ are one or more parameters of one or more patterns measured. As will be appreciated, in and m can be 1. Further, the metrology recipe does not need to have both one or more parameters of the measurement and one or more parameters of one or more patterns measured, it can have just one or more parameters of the measurement or have just one or more parameters of one or more patterns measured.

A target may be subjected to measurement using two metrology recipes A and B, e.g., differ on the stage at which a target is measured (e.g., A measures a target when it comprises a latent image structure and B measures a target when it doesn't comprise a latent image structure) and/or differ on the parameters of their measurement. Metrology recipes A and B can at least differ on the target measured (e.g., A measures a first target and B measures a second different target). Metrology recipes A and B may differ on the parameters of their measurement and target measured. Metrology recipes A and B may not even be based on the same measurement technique. For example recipe A may be based on diffraction-based measurement and recipe B may be based on scanning electron microscope (SEM) or atomic force microscopy (AFM) measurement.

As noted, a particular substrate will have a plurality of instances of target. So, in an embodiment, there will typically be a sampling scheme to select a subset of the target instances on the substrate for measurement on the substrate to facilitate, e.g., throughput of the measurement process.

As discussed above, one or more parameters of interest (such as CD and/or overlay) can be determined from a structure of a target (e.g., a diffracting target within a product pattern or a diffracting target specially designed for measurement and separate from a device pattern) by illuminating the target, collecting the redirected radiation from the structure using an objective lens, and detecting the redirected radiation by a pupil detector in a Fourier plane of the objective lens. Such a measured pupil can be processed using, for example, an inference method as described herein that obtains signal components therefrom, which signal components are combined with an appropriate set of weights to yield, e.g., an overlay value. Additionally or alternatively, a method such as described with respect to FIG. 9 can use such a measured pupil to determine, e.g., CD.

In an embodiment, the radiation used to illuminate the target is linearly-polarized electromagnetic radiation. Linear polarization has the electric field of the electromagnetic radiation confined to a single plane along the direction of propagation. In an embodiment, a first type of linear polarization in a first direction perpendicular to the direction of propagation is designated herein for convenience as "H" or horizontal linear polarization and a second type of linear polarization in a second direction that is orthogonal to the first direction and is perpendicular to the direction of propagation is designated herein for convenience as "V" or vertical linear polarization. Of course, the radiation need not be vertical or horizontal. The first linear polarization can be p polarization and the second linear polarization can be s polarization. Of course, the first and second linear polarization can be labelled with other designations.

A diffracting structure (e.g., a diffraction grating) and other similarly complex structure changes the polarization state of illumination radiation. So, in an embodiment, the optical properties of a target comprising a structure under study can be characterized by a reflectivity matrix as follows:

$$\begin{pmatrix} R_{HH} & R_{HV} \\ R_{VH} & R_{VV} \end{pmatrix} \quad (18)$$

wherein R is the reflectivity and the subscripts correspond to the applicable linear polarization. In particular, the first index of the subscript refers to the polarization state of the outgoing radiation from the target, and the second index of the subscripts refers to the polarization state of the illumination radiation onto the target. For example, $R_{HV}$ means reflectivity to the H polarization from V-polarized illumination. Each element of this matrix depends on wavelength, and polar and azimuthal angles of incidence. Of course, the structures can be characterized by the reflectivity matrices in a s and p polarization basis or other basis. Further, while embodiments are described herein in terms of reflectivity, a different or additional optical characteristic can be used than reflectivity, which different or additional optical characteristic can be determined in similar respects at different illumination polarizations and outgoing polarizations. Further, while embodiments are described herein in terms of two different types of linear polarization, more than two types of linear polarization can be used.

In a metrology apparatus, the observable quantities by a detector can be total reflected intensities. That is, the detection is not polarization-sensitive. Therefore, if illumination is H-polarized, then the detected intensity is directly proportional to:

$$|R_{HH}|^2 + |R_{VH}|^2 \quad (19)$$

and if illumination is V-polarized, then the detected intensity is proportional to:

$$|R_{VV}|^2 + |R_{HV}|^2 \quad (20)$$

However, it is expected that different polarization channels (i.e. different elements of the reflectivity matrix) carry different information about a parameter of interest such as CD and/or overlay. Therefore, in an embodiment, it is advantageous to detect outgoing H linear polarization and V linear polarization radiation from the target to, for example, separately de-correlate more profile parameters (e.g., as part of the inference method) and increase sensitivity to them. Thus, in an embodiment, a combination of values associated with at least two selected from $R_{HH}$, $R_{VH}$, $R_{VV}$, and $R_{HV}$ (or an additional or different optical characteristic as described above) are used to derive a parameter of interest (e.g., overlay, CD, etc.). As will be appreciated, the combination can be used to derive a single value of the parameter of interest. In an embodiment, values corresponding to $R_{HH}$, $R_{VH}$, $R_{VV}$, and $R_{HV}$ are used together to derive a parameter of interest. In an alternative embodiment, only values corresponding to $R_{VH}$ and $R_{HV}$ are used to derive the parameter of interest.

Figure 21:
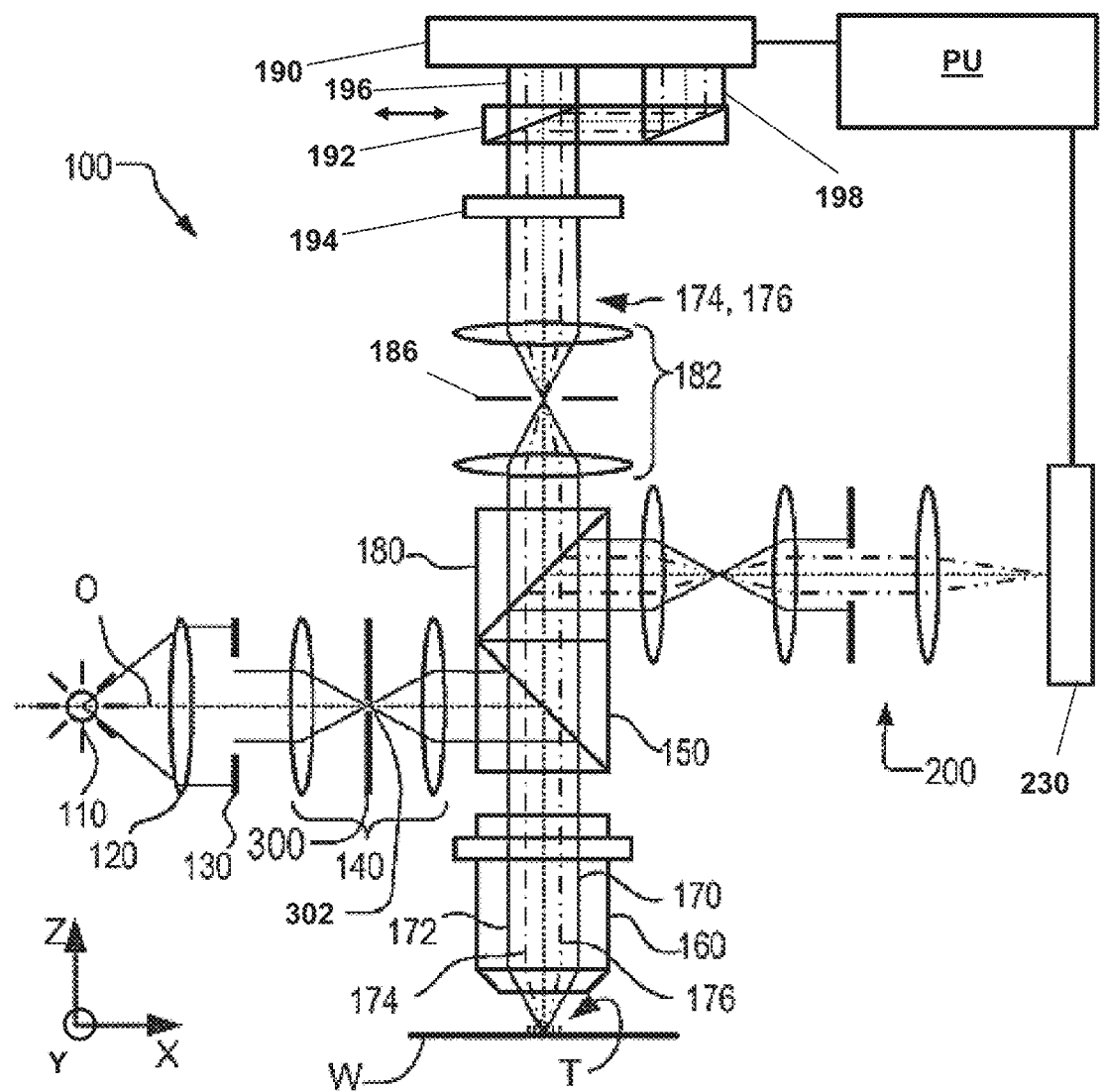
FIG. 21 schematically depicts an example metrology apparatus according to an embodiment.

So, FIG. 21 schematically depicts an example metrology apparatus according to an embodiment to enable separate detection of outgoing H- and V-polarizations from the target. This embodiment is similar to the metrology apparatus of FIG. 7 with some changes. In particular, in an embodiment, the metrology apparatus comprises a cross-polarizing element 192 before the pupil sensor 190 to separate the outgoing polarization states of radiation into a first portion 196 having a first linear polarization and a second portion 198 having a second different linear polarization. This means the ability to measure values associated with $R_{HH}$, $R_{VH}$, $R_{VV}$, and $R_{H}V$ separately, such as $|R_{HH}|^2$, $|R_{VH}|^2$, $|R_{VV}|^2$, and $|R_{HV}|^2$ respectively, by applying horizontal linear polarization illumination radiation to the target and separately applying vertical linear polarization illumination radiation to the same target. Thus, for the H polarization, the cross-polarizing element 192 enables the outgoing V and H polarization to be separately measured to obtain $|R_{VH}|^2$ and $|R_{VV}|^2$ respectively. Similarly, for the V polarization, the cross-polarizing element 192 enables the outgoing V and H polarization to be separately measured to obtain $|R_{VV}|^2$ and $|R_{HV}|^2$ respectively.

In an embodiment, the different polarizations can be alternately provided to the target. For example, in an embodiment, the source 110 can alternately provide in time H and V polarization. In an embodiment, a polarizing element in the optical path between the source 110 and the target can be used to alternately provide in time H and V polarization (e.g., using a polarizer 170 as depicted in FIG. 9 and which can be similarly provided between the source 110 and the objective 160 in FIGS. 7 and 21).

In an embodiment, a plurality of illumination spots can be provided in parallel, one or more of those illumination spots having H polarization and one or more other of those illuminations having V polarization. So, in an embodiment having two illuminations spots with one spot having V polarization and the other H polarization, the cross-polarizing element 192 can split the polarizations from each of the spots separately to measure 4 sets of linear polarization—V polarized outgoing radiation from the target for V illumination, H polarized outgoing radiation from the target for V illumination, V polarized outgoing radiation from the target for H illumination, and H polarized outgoing radiation from the target for H illumination.

In an embodiment, the cross-polarizing element 192 can be differently arranged. For example, it can be in a polarizing beam splitter-type arrangement where a particular linear polarization passes through the beam splitting surface in a first direction toward one sensor 190 in the first direction and the orthogonal linear polarization reflects off the beam splitting surface in a second direction substantially orthogonal to the second direction to another sensor 190 in the second direction. Other arrangements are possible including other beam directing components.

However, a cross-polarized detection alone is not sensitive to phases of reflectivity coefficients, as only their absolute values are measured. In order to be able to measure at least some relative phases, a retarder 194 (e.g., a quarter-wave plate) is positioned before the cross-polarizing element 192. In such a retarder 194 and cross-polarizing element 192 configuration, two output intensity channels for H polarized illumination of the target are:

$$|R_{HH} \pm iR_{VH}|^2 = |R_{HH}|^2 + |R_{VH}|^2 \pm 2\ \mathrm{Im}(R_{HH}R_{VH}^*) \quad (21)$$

and for V polarized illumination of the target are:

$$|R_{VV} \pm iR_{HV}|^2 = |R_{VV}|^2 + |R_{HV}|^2 \pm 2\ \mathrm{Im}(R_{VV}R_{VH}^*) \quad (22)$$

The interference terms carry information about relative phases between on-diagonal and off-diagonal channels of the reflectivity matrix. So, a retarder 194 and cross-polarizing element 192 configuration can be particularly useful in metrology techniques described herein (e.g., the overlay inference method based on signal components from a pupil combined with weightings) that take advantage of a relatively strong signal typically found only in the tonsil areas (e.g., areas 1075 and 1080) because it spreads the energy of the parameter of interest (e.g., overlay) signal across a relatively large area of the pupil as compared to a configuration not having the retarder 194 (i.e., having a cross-polarizing element 192 but not the retarder 194).

Figure 22:
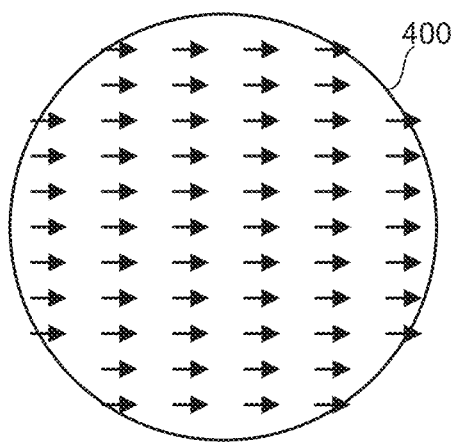
FIG. 22 schematically depicts an orientation of polarization in a pupil plane for H polarization radiation.
Figure 23:
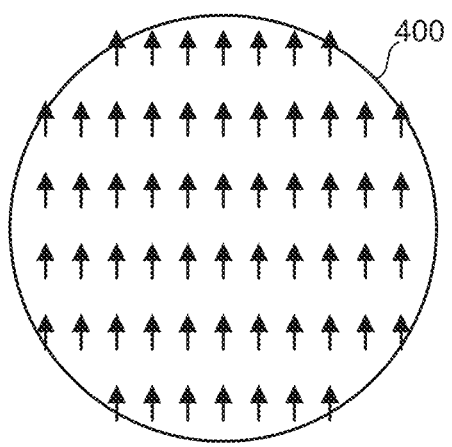
FIG. 23 schematically depicts an orientation of polarization in a pupil plane for V polarization radiation.

An orientation of polarization in a pupil plane 400 of H polarization radiation is depicted schematically in FIG. 22. An orientation of polarization in a pupil plane 400 of V polarization radiation is depicted schematically in FIG. 23. In each case, the direction of polarization is pointing in the same direction for all points in the pupil plane 400. Such polarization can be achieved relatively easily by a polarizer that acts uniformly on radiation across the pupil plane 400. The reflectivity properties of a target structure are more accurately characterized by reference to reflectivity in the sp-basis. The sp-basis is intrinsic to the target structure. Light polarized orthogonally to the plane of incidence of the light onto the target structure is referred to as s-polarized light in the sp-basis. The plane of incidence is the plane containing both the normal vector to the plane of the substrate W on which the target structure is formed and the wave vector of the incident light. Light polarized within the plane of incidence is referred to as p-polarized light. In contrast to the H and V polarizations discussed above, the directions of the s- and p-polarizations both vary as a function of position within the pupil plane. This variation is due to the correspondence between the position at which radiation passes through the pupil plane and the resulting polar and azimuthal angles of incidence of the radiation onto the target structure.

The reflectivity matrix of the target structure in the sp-basis may be written as follows:

$$\begin{pmatrix} R_{pp} & R_{ps} \\ R_{sp} & R_{ss} \end{pmatrix}$$

Each element of the reflectivity matrix depends on wavelength and on the polar and azimuthal angles of incidence of the polarized radiation onto the target structure. The first index refers to the polarization state of the redirected radiation. The second index refers to the polarization state of the incident radiation. Thus, $R_{ps}$ for example describes the efficiency and phase of conversion of incident s-wave radiation into redirected p-wave radiation.

In the metrology apparatus described above with reference to FIG. 21, when H or V polarized radiation is provided in the illumination pupil plane, the objective 160 effectively decomposes the H or V polarized radiation into corresponding s- and p-polarized radiation when the radiation is incident onto the target structure. The target structure redirects the radiation according to the reflectivity matrix in sp-basis given above. The redirected radiation passes again through the objective 160. The objective 160 converts the s- and p-polarized radiation back into H and V polarized radiation which are separated by the cross-polarizing element 192 and detected by the pupil sensor 190. Thus, for an external observer using such an apparatus, a target structure can only be characterized by the reflectivity matrix in hv-basis (i.e. in terms of H polarization radiation and V polarization radiation). The hv-basis is related to the reflectivity matrix of the target structure in sp-basis via the following formula:

$$\begin{pmatrix} R_{hh} & R_{hv} \\ R_{vh} & R_{vv} \end{pmatrix} = \begin{pmatrix} \cos\varphi & -\sin\varphi \\ \sin\varphi & \cos\varphi \end{pmatrix} \begin{pmatrix} R_{pp} & R_{ps} \\ R_{sp} & R_{ss} \end{pmatrix} \begin{pmatrix} \cos\varphi & \sin\varphi \\ -\sin\varphi & \cos\varphi \end{pmatrix}$$

Here $\varphi$ is the angular coordinate in the pupil plane (azimuthal angle of incidence as seen by the target structure). The first rotation matrix describes propagation through the objective 160 from illumination pupil plane to the target structure. The second rotation matrix (which is an inverse of the first rotation matrix) describes propagation though the objective 160 back to the detection pupil plane. The resulting reflectivity components in hv-basis are given as follows:

$R_{hh} = R_{pp}\cos^2\varphi - R_{ps}\cos\varphi\sin\varphi - R_{sp}\cos\varphi\sin\varphi + R_{ss}\sin^2\varphi$ $R_{hv} = R_{pp}\cos\varphi\sin\varphi + R_{ps}\cos^2\varphi - R_{sp}\sin^2\varphi - R_{ss}\cos\varphi\sin\varphi$ $R_{vh} = R_{pp}\cos\varphi\sin\varphi - R_{ps}\sin^2\varphi + R_{sp}\cos^2\varphi - R_{ss}\cos\varphi\sin\varphi$ $R_{vv} = R_{pp}\sin^2\varphi + R_{ps}\cos\varphi\sin\varphi + R_{sp}\cos\varphi\sin\varphi + R_{ss}\cos^2\varphi$ The metrology apparatus of FIG. 21 is able to detect intensities corresponding to $|R_{hh}|^2$, $|R_{vv}|^2$, $|R_{vh}|^2$, and $|R_{hv}|^2$. For certain classes of target structure, for example 1D or 2D gratings with rectangular unit cells (e.g. logic applications), information about parameters of interest such as overlay, or other symmetries in the target structure (e.g. side wall angle), may be contained predominantly or entirely in the $|R_{vh}|^2$ and $|R_{hv}|^2$ and not in either of the $|R_{hh}|^2$ or $|R_{vv}|^2$ components. Selectively detecting V or H polarization radiation from the target structure may therefore be effective for isolating information about the parameter of interest from background noise. However, because the hv-basis is not the intrinsic basis of the target structure, this may not be the optimal approach, particularly where the target structure has a more complex unit cell. A more complex unit cell may mean that all of the polarization components carry useful signal (albeit with different strengths). Embodiments of the present disclosure discussed below aim to improve the flexibility or sensitivity with which information about a parameter of interest may be extracted. Polarization dependent measurements are described which provide improved access to reflectivity properties of the target structure in the intrinsic sp-basis.

All intensity components derived from reflectivity components in the hv-basis listed above contain terms such as the following: $|R_{pp}|^2$, $|R_{ss}|^2$, $|R_{ps}|^2$, and $|R_{sp}|^2$ and cross-terms like $\text{Re}(R_{pp}R_{ps}^*)$, $\text{Re}(R_{pp}R_{sp}^*)$, $\text{Re}(R_{ss}R_{sp}^*)$, and $\text{Re}(R_{sp}R_{ps}^*)$ and others. For example, a total detected intensity of all polarization components of radiation redirected in the case of H polarization illumination radiation is given as follows:

$I_h = |R_{hh}|^2 + |R_{vh}|^2 = (|R_{pp}|^2 + |R_{sp}|^2)\cos^2\varphi + (|R_{ps}|^2 + |R_{ss}|^2)\sin^2\varphi - 2\,\text{Re}(R_{pp}R_{ps}^* + R_{ss}R_{sp}^*)\cos\varphi\sin\varphi.$ Computer modelling each term in the above expression for a simple target structure comprising a grating on a grating in a rectangular unit cell demonstrates that the $|R_{pp}|^2$ and $|R_{ss}|^2$ terms do not carry any signal about overlay. Information about overlay is only present in the cross-polarization reflectivities in this example.

It is desirable to remove contributions to a detected signal that do not contain information about a parameter of interest, such as $|R_{pp}|^2$ and $|R_{ss}|^2$ in the above example. Removing $|R_{hh}|^2$ and $|R_{vv}|^2$ components by selectively detecting $|R_{hv}|^2$ or $|R_{vh}|^2$, as may be achieved using the metrology apparatus of FIG. 21, provides significant improvement over strategies which do not use polarization dependent detection. However, as described above, $|R_{hv}|^2$ and $|R_{vh}|^2$ both contain contributions from terms proportional to $|R_{pp}|^2$ and $|R_{ss}|^2$. Radiation that does not contain information about the parameter of interest may thus not be optimally removed using this strategy. Further improvement may be achieved by performing measurements in the sp-basis more directly, which allows contributions from terms such as $|R_{pp}|^2$ and $|R_{ss}|^2$, or other terms which do not contain useful information, to be removed more effectively. An example apparatus for performing such measurements is depicted in FIG. 24 and described below.

Figure 24:
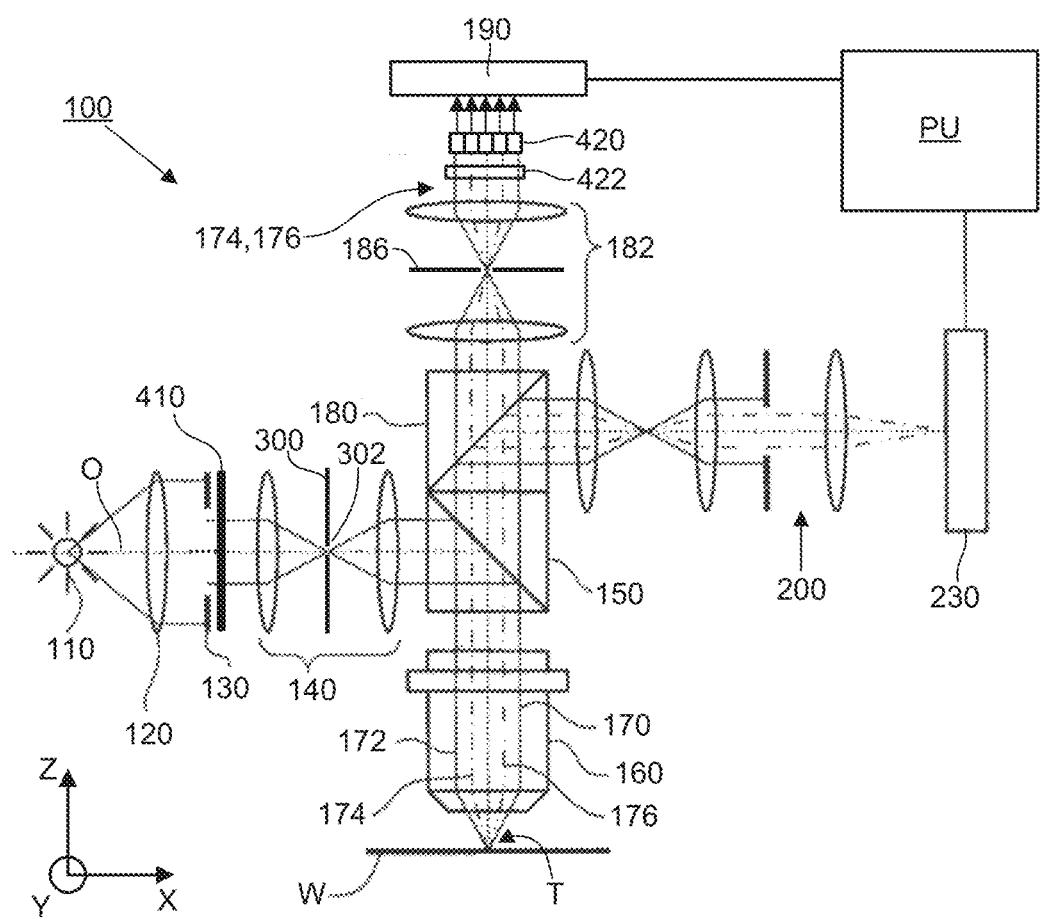
FIG. 24 schematically depicts an example metrology apparatus according to an embodiment.

In an embodiment, an example of which is depicted in FIG. 24, a metrology apparatus 100 is provided for measuring a target structure on a substrate W. The metrology apparatus 100 comprises an optical system that focuses radiation onto the target structure and directs radiation after reflection from the target structure onto a detection system. The metrology apparatus 100 is similar to the metrology apparatus 100 of FIG. 21 with some changes. In particular, a beam processing device 420 is provided for selectively extracting a plurality of different components of the radiation beam after reflection from the target structure. The beam processing device 420 directs each of the extracted components to the detection system such that each component can be detected independently of each other component. In the embodiment shown, the detection system comprises a pupil sensor 190 configured as described above with reference to FIG. 21.

Figure 25:
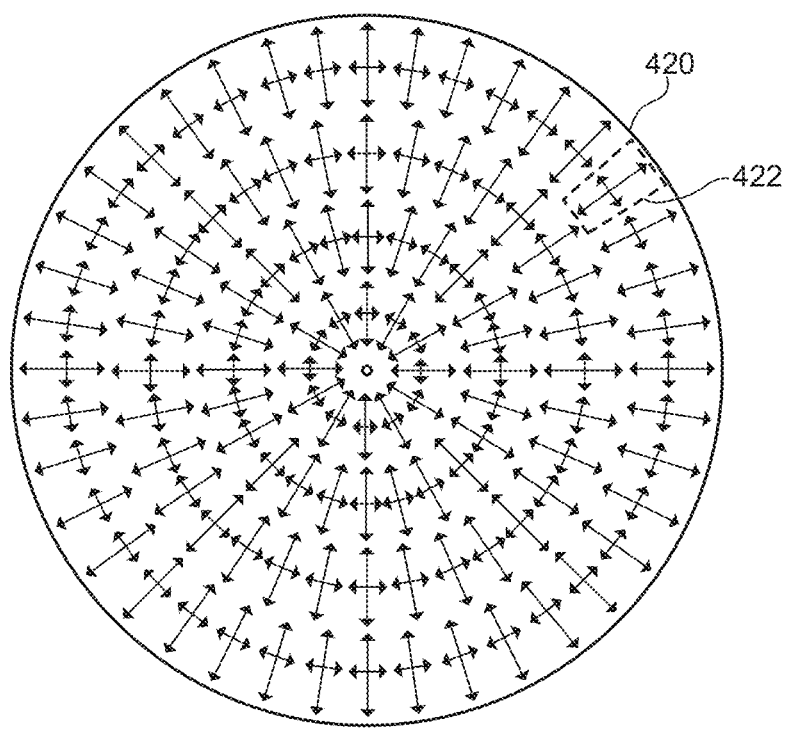
FIG. 25 schematically depicts a beam processing device in a downstream pupil plane, viewed perpendicularly to the downstream pupil plane.

An example beam processing device 420 is depicted in FIG. 25. The beam processing device 420 is configured such that the selective extraction comprises, for each component: 1) selecting radiation from one of a plurality of predetermined regions in a downstream pupil plane of the optical system downstream from the structure, the selected predetermined region being different for each of at least a subset of the components; and 2) selecting radiation from one of two predetermined orthogonal polarization states, the predetermined orthogonal polarization states being oriented differently as a pair for each of at least a subset of the components comprising radiation selected from different predetermined regions in the downstream pupil plane. In an embodiment, the beam processing device 420 is positioned in the downstream pupil plane. A region of the beam processing device 420 corresponding to one of the predetermined regions in the downstream pupil plane is marked by a broken line delimited region labeled 422. Many other predetermined regions may be present. In the example of FIG. 25, each pair of crossed double ended arrows is located in one such predetermined region. Each pair of crossed double ended arrows schematically represents example directions for the predetermined orthogonal polarization states for the corresponding predetermined region.

The predetermined orthogonal polarization states available for selection are oriented differently as a pair (e.g. non-parallel) for at least a subset of the plurality of predetermined regions in the downstream pupil plane. This is illustrated in FIG. 25, where the pair of polarization states for each region are oriented differently for most regions at different azimuthal positions in the pupil plane.

In an embodiment, the predetermined orthogonal polarization states for each of at least a subset of the plurality of predetermined regions of the downstream pupil plane comprise a substantially radially oriented polarization state and a substantially circumferentially oriented polarization state. In the particular example of FIG. 25, the predetermined orthogonal polarization states for each of the plurality of predetermined regions of the downstream pupil plane comprise a substantially radially oriented polarization state and a substantially circumferentially oriented polarization state. The example beam processing device 420 is thus configured to selectively measure p- and s-polarized components of the radiation redirected from the target structure for a subset or for all of the predetermined regions of the downstream pupil plane.

In an embodiment, the beam processing device 420 selectively directs the different extracted components onto different regions on the pupil sensor 190 to allow independent measurement of the components. In other embodiments, the beam processing device 420 selectively directs the different extracted components onto plural different sensors, such as a plurality of photodiodes disposed in a 2D array.

The ability to selectively measure radiation from different pairs of orthogonal polarization states in different regions of the downstream pupil plane provides increased flexibility to extract information about a parameter of interest that influences how the target structure reflects radiation. The functionality allows more direct measurement of radiation corresponding to p- or s-polarized radiation in multiple regions of the downstream pupil plane.

In an embodiment, the metrology apparatus 100 further comprises a polarization system 410. The polarization system 410 polarizes the radiation focused onto the target structure. In an embodiment, the polarization system 410 applies a set of polarizations to a plurality of predetermined regions in an upstream pupil plane of the optical system. In an embodiment, the polarization system 410 is positioned in the upstream pupil plane, as depicted in FIG. 24. The upstream pupil plane is upstream from the target structure. The set of polarizations comprises different polarizations for at least a subset of the plurality of predetermined regions in the upstream pupil plane. The set of polarizations may thus be made to correspond more closely to p- and s-polarized radiation than is possible using purely H polarization incident radiation or purely V polarization incident radiation.

In an embodiment, the different polarizations comprise linear polarizations that are oriented in different directions.

In an embodiment, the set of polarizations are oriented substantially radially in the upstream pupil plane, thereby substantially corresponding to p-polarized radiation.

In an embodiment, the set of polarizations are oriented substantially circumferentially in the upstream pupil plane, thereby substantially corresponding to s-polarized radiation.

In an embodiment, the polarization system 410 is switchable between a first polarizing state and a second polarizing state. In an embodiment, the polarization system 410 comprises a plurality of liquid crystal spatial light modulators that are capable of being switched to change their polarizing properties and thereby switch the polarization system 410 from the first polarizing state to the second polarizing state or vice versa.

Figure 26:
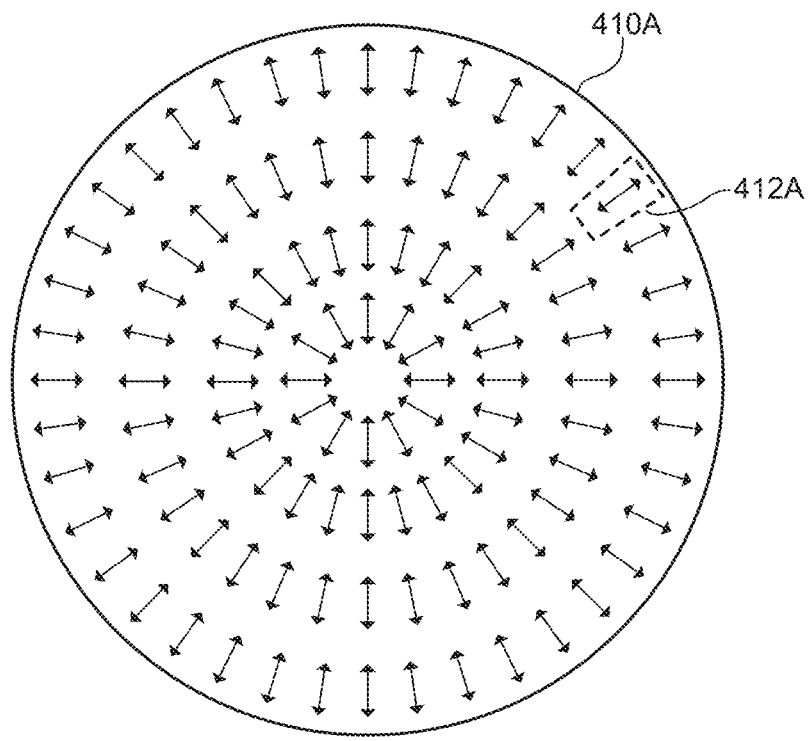
FIG. 26 schematically depicts a polarization system in a first polarizing state in an upstream pupil plane, viewed perpendicularly to the upstream pupil plane.

In an embodiment, the first polarizing state is such as to apply the set of polarizations that are oriented substantially radially in the upstream pupil plane. An example polarization system 410A in the first polarizing state is depicted schematically in FIG. 26. A region of the polarization system 410A corresponding to one of the predetermined regions in the upstream pupil plane is marked by a broken line delimited region labeled 412A in FIG. 26.

Figure 27:
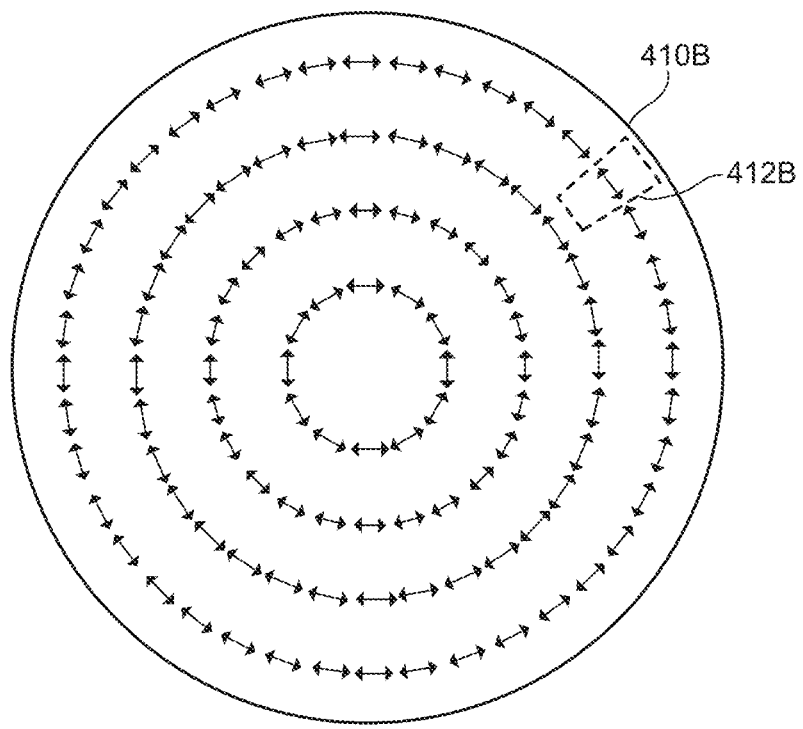
FIG. 27 schematically depicts a polarization system in a second polarizing state in an upstream pupil plane, viewed perpendicularly to the upstream pupil plane.

In an embodiment, the second polarizing state is such as to apply the set of polarizations that are oriented substantially circumferentially in the upstream pupil plane. An example polarization system 410B in the second polarizing state is depicted schematically in FIG. 27. A region of the second polarizing element 410B corresponding to one of the predetermined regions in the upstream pupil plane is marked by a broken line delimited region labeled 412B in FIG. 27.

The polarization system 410 is configured so that the different sets of polarizations corresponding to each of the first and second polarization states can be applied at different times.

The combination of the beam processing device 420 and the polarization system 410 makes it possible to illuminate the target structure in the sp-basis and detect redirected radiation in the sp-basis. In particular, the detection system is able to independently detect intensities corresponding to $|R_{pp}|^2$, $|R_{ss}|^2$, $|R_{ps}|^2$, and $|R_{sp}|^2$. In the case of measuring a parameter of interest such as overlay which is not normally present in the $|R_{pp}|^2$ and $|R_{ss}|^2$ component, background radiation from these components can be more effectively avoided or suppressed, thereby providing improved sensitivity in the measurement of the parameter of interest.

Further information may be obtained from cross-terms, such as the following: $\text{Re}(R_{pp}R_{ps}^*)$, $\text{Re}(R_{pp}R_{sp}^*)$, $\text{Re}(R_{ss}R_{sp}^*)$, and $\text{Re}(R_{sp}R_{ps}^*)$. Access to such cross-terms can be achieved by arranging for the predetermined orthogonal polarization states for each of at least a subset of the plurality of predetermined regions of the downstream pupil plane to comprise a polarization state oriented at a common oblique angle to the radial direction (i.e. the same oblique angle for a plurality of the predetermined regions).

In an embodiment, the beam processing device 420 is switchable between a first state and a second state. The first state is such that, for each of at least a subset of the plurality of predetermined regions of the downstream pupil plane, the predetermined orthogonal polarization states comprise a substantially radially oriented polarization state and a substantially circumferentially oriented polarization state. The second state is such that, for each of the at least a subset of the plurality of predetermined regions of the downstream pupil plane, the predetermined orthogonal polarization states comprise a polarization state oriented at a common oblique angle to the radial direction. The same beam processing device 420 can therefore be configured to extract radial and circumferentially polarized radiation when in the first state, and polarized radiation that is respectively rotated by the common oblique angle relative to the radial and circumferential directions when in the second state.

In an embodiment, the common oblique angle is set to 45 degrees. Thus, each of the polarization directions depicted in FIG. 25 would be rotated by 45 degrees. The reflectivity matrix up to detection by the detection system in such an embodiment is given as follows:

$$\begin{pmatrix} \cos\frac{\pi}{4} & \sin\frac{\pi}{4} \\ -\sin\frac{\pi}{4} & \cos\frac{\pi}{4} \end{pmatrix} \begin{pmatrix} R_{pp} & R_{ps} \\ R_{sp} & R_{ss} \end{pmatrix} = \frac{1}{\sqrt{2}} \begin{pmatrix} R_{pp} + R_{sp} & R_{ps} + R_{ss} \\ -R_{pp} + R_{sp} & -R_{ps} + R_{ss} \end{pmatrix}$$

For p-polarized illumination, for example, two detection channels are provided:

$$I_1 = |R_{pp} + R_{sp}|^2 = |R_{pp}|^2 + |R_{sp}|^2 + 2\,\text{Re}(R_{pp}R_{sp}^*)$$

$$I_2 = |R_{pp} - R_{sp}|^2 = |R_{pp}|^2 + |R_{sp}|^2 - 2\,\text{Re}(R_{pp}R_{sp}^*)$$

The interference cross-terms may be isolated by forming a differential channel, as follows:

$$(I_1 - I_2)/2 = 2\,\text{Re}(R_{pp}R_{sp}^*)$$

The procedure can be repeated for s-polarized illumination to obtain a different cross-term.

In a further embodiment, beam processing device 420 further comprises a plurality of retarders 422. Each retarder of the plurality of retarders 422 overlaps, when viewed along a direction of incidence of radiation onto the retarder, with one of the predetermined regions in the downstream pupil plane and has axes aligned at a common angle with respect to the predetermined orthogonal polarization states corresponding to the predetermined region with which the retarder overlaps. In an embodiment, the common angle is substantially 45 degrees. In an embodiment, the plurality of retarders 422 comprises a plurality of quarter wave plates. In an embodiment, the plurality of retarders 422 is implemented using spatial light modulators. In an embodiment, the plurality of retarders comprises birefringent plates. The reflectivity matrix up to detection by the detection system in such an embodiment is given as follows:

$$\frac{1}{\sqrt{2}} \begin{pmatrix} 1 & i \\ i & 1 \end{pmatrix} \begin{pmatrix} R_{pp} & R_{ps} \\ R_{sp} & R_{ss} \end{pmatrix} = \frac{1}{\sqrt{2}} \begin{pmatrix} R_{pp} + iR_{sp} & R_{ps} + iR_{ss} \\ i(R_{pp} - iR_{sp}) & i(R_{ps} - iR_{ss}) \end{pmatrix}$$

For p-polarized illumination, for example, two detection channels are provided:

$$I_1 = |R_{pp} + iR_{sp}|^2 = |R_{pp}|^2 + |R_{sp}|^2 + 2\,\text{Im}(R_{pp}R_{sp}^*)$$

$$I_2 = |R_{pp} - iR_{sp}|^2 = |R_{pp}|^2 + |R_{sp}|^2 - 2\,\text{Im}(R_{pp}R_{sp}^*)$$

The interference cross-terms may be isolated by forming a differential channel, as follows:

$$(I_1 - I_2)/2 = 2\,\text{Im}(R_{pp}R_{sp}^*)$$

The procedure can be repeated for s-polarized illumination to obtain a different cross-term. Such interference terms (proportional to imaginary parts of cross-terms) can be even stronger than interference terms proportion to real parts of cross-terms. Providing the ability to access these terms may therefore allow parameters of interest to be detected more flexibly and/or with increased sensitivity.

The above embodiments thus provide increased freedom in accessing information about the reflectivity properties of the target structure, including the ability not only to measure absolute values of reflectivity components in the intrinsic sp-basis, but also relative phases between different components in the sp-basis. This increased freedom may provide increased sensitivity in measurements of parameters of interest related to asymmetries in the target structure, such as overlay or asymmetric differences in side wall angles. Alternatively or additionally, the additional information may improve CD profile characterization because different parameters of the CD profile typically contribute differently to absolute values and phases of reflectivities.

In the case where the parameter of interest is related to an asymmetry in the target structure, such as overlay or asymmetric differences in side wall angles, information can be obtained by making use of the fact that the parameter of interest causes the following inequality $R_{sp} \neq R_{ps}$. In an embodiment, the target structure is illuminated with p-polarized radiation and s-polarized radiation is detected, thereby obtaining $|R_{sp}|^2$. The target structure is then illuminated with s-polarized radiation and p-polarized radiation is detected, thereby obtaining $|R_{ps}|^2$. Information about the asymmetry in the target structure, such as overlay or asymmetric differences in side wall angles, can be obtained from the difference between the obtained $|R_{sp}|^2$ and $|R_{ps}|^2$. Detecting these intensities in the intrinsic sp-basis is expected to provide a stronger signal than detecting corresponding intensities in the hv-basis.

Asymmetries within a target structure that are not caused by overlay can contribute to asymmetry in radiation reflected from the target structure during a metrology process and thereby interfere with accurate determination of overlay. The optical response from non-overlay related asymmetry in the target structure may have a different dependence on properties of the illumination radiation such as wavelength or polarization in comparison with the optical response from overlay induced asymmetry. This provides a basis for decoupling effects of overlay from other contributions to asymmetry, thereby allowing overlay to be measured more accurately.

The polarization dependence of a target structure is defined most accurately by reference to the intrinsic sp-basis of the target structure, as described above. When a target structure is illuminated with spatially uniform polarization, for example the H or V polarizations discussed above, the illumination comprises a mixture of s- and p-polarizations for radiation from all points in the pupil plane except points lying along axes parallel or perpendicular to the direction of the uniform polarization. The radiation reflected from the target structure will then contain a mixture of response to both s- and p-polarizations. When the reflected radiation is detected as an image in an image plane, the image will be a mixture of a mixture of s- and p-polarization responses because all points in the pupil plane from which radiation is provided will contribute to each and every point in the image. The result of this is that the difference of optical responses to asymmetries between reflected radiation resulting from illumination with different directions of uniform polarization (e.g. between H polarized illumination and V polarized illumination) can be very small. The following embodiments allow the polarization dependence of a target structure to be measured with improved sensitivity and/or accuracy.

In an embodiment, a method of measuring a target structure formed on a substrate W is provided. The method may be implemented using at least a portion of the metrology apparatus 100 depicted in FIG. 24. The method uses an optical system to perform one or more measurement processes. Each measurement process comprises illuminating the target structure with radiation and detecting radiation redirected (e.g. reflected) by the target structure. The radiation may be detected by a detection system. In an embodiment, the detection system is configured to detect an image in an image plane. The detection system may be implemented by the sensor 230 in FIG. 24 for example. In this case, the optical system would comprise the optical elements in the optical path between the radiation source 110 and the sensor 230. Optical elements leading from the partially reflecting surface 150 to the sensor 190 are optional for these embodiments.

In each of one or more of the measurement processes, the radiation illuminating the target structure consists of at least 90%, optionally at least 95%, optionally at least 98%, optionally at least 99%, optionally at least 99.9% p-polarized radiation or consists of at least 90%, optionally at least 95%, optionally at least 98%, optionally at least 99%, optionally at least 99.9% s-polarized radiation.

In an embodiment, either or both of the p-polarized radiation and the s-polarized radiation is produced by applying a uniform polarization to radiation upstream from the target structure and removing a portion of the radiation in a pupil plane upstream from the target structure using an aperture. The removed portion of the radiation is such as to increase a proportion of the p- or s-polarized radiation in the radiation passed by the aperture, thereby achieving the desired level of purity of polarization. In an embodiment, the uniform polarization is provided by a polarizer. The polarizer may be provided for example as part of the polarization system 410 of FIG. 24. The uniform polarization is spatially uniform, for example spatially uniform (e.g. pointing in the same direction) at all positions in the pupil plane. The uniform polarization may be the H or V polarization discussed above.

Figure 28:
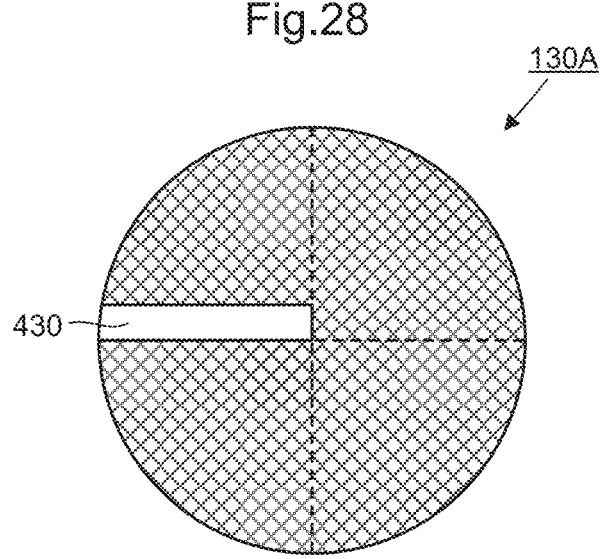
FIG. 28 schematically depicts an example aperture for illuminating a periodic target structure parallel to a direction of periodicity of the target structure.
Figure 29:
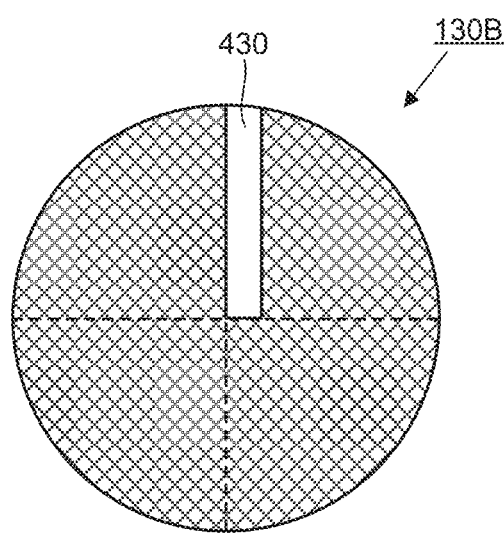
FIG. 29 schematically depicts an example aperture for illuminating a periodic target structure perpendicularly to a direction of periodicity of the target structure.

FIGS. 28 and 29 depict example apertures 130A, 130B. In an embodiment, the apertures 130A, 130B each comprise an aperture plate 130 positioned in a pupil plane, as depicted in FIG. 24. Each aperture 130A, 130B comprises an opening 430 through which radiation can pass. Radiation is not allowed to pass through the cross-hatched region. Any radiation incident on the cross-hatched region is thus removed.

In an embodiment, the apertures 130A, 130B are configured so that the opening 430 is aligned parallel to or orthogonal to the direction of uniform polarization provided by the polarizer. In an embodiment, the opening 430 is elongate (as depicted in FIGS. 28 and 29) with the longest axis lying parallel to or orthogonal to the direction of uniform polarization. Thus, in a case where the polarizer provides H polarized radiation, with a polarization direction being horizontal in the plane of the page of FIGS. 28 and 29, the opening 430 in aperture 130A would pass predominantly p-polarized light (oriented radially) and the opening 430 in aperture 130B would pass predominantly s-polarized light (oriented azimuthally). In a case where the polarizer provides V polarized radiation, with a polarization direction being vertical in the plane of the page of FIGS. 28 and 29, the opening 430 in aperture 130A would pass predominantly s-polarized light (oriented azimuthally) and the opening 430 in aperture 130B would pass predominantly p-polarized light (oriented radially).

In some embodiments, the target structure is a periodic structure having a periodicity in a first direction. For example, the target structure may comprise a grating comprising parallel lines evenly spaced apart from each other along the first direction. Each line may be orthogonal to the first direction in this example. The optical response from the target structure is expected to be significantly different for radiation illuminating the target structure from directions parallel to the first direction (e.g. perpendicular to the grating lines) in comparison to radiation illuminating the target structure from directions perpendicular to the first direction (e.g. parallel to the grating lines), when viewing the substrate W perpendicularly to the plane of the substrate. Useful information can be obtained by measuring these two optical responses separately from each other. The following embodiment allows this to be done while also allowing the predominantly (or purely) p- or s-polarized radiation to be used to illuminate the target structure.

In an embodiment, in each of one or more of the measurement processes, at least 90%, optionally at least 95%, optionally at least 98%, optionally at least 99%, optionally at least 99.9%, of the radiation illuminating the target structure is orientated so that the component of the wavevector of the radiation in the plane of the substrate W is aligned within 10 degrees, optionally within 5 degrees, optionally within 2 degrees, optionally within 1 degree, optionally within 0.1 degrees of the first direction. In an embodiment, this is achieved by arranging for the aperture 130A to exclusively pass radiation that will be orientated at the substrate W such that the component of the wavevector of the radiation in the plane of the substrate W is aligned within 10 degrees, optionally within 5 degrees, optionally within 2 degrees, optionally within 1 degree, optionally within 0.1 degrees of the first direction. If the target structure is oriented so that the first direction is horizontal in the plane of the page relative to the orientation of the aperture 130A of FIG. 28, the alignment with the first direction can be achieved using aperture 130A. Thus, the target structure can be illuminated perpendicularly to the grating lines of a target structure with p-polarized radiation by using aperture 130A in combination with H polarized radiation and with s-polarized radiation by using aperture 130A in combination with V polarized radiation.

In an embodiment, in each of one or more of the measurement processes, at least 90%, optionally at least 95%, optionally at least 98%, optionally at least 99%, optionally at least 99.9%, of the radiation illuminating the target structure is orientated so that the component of the wavevector of the radiation in the plane of the substrate W is aligned within 10 degrees, optionally within 5 degrees, optionally within 2 degrees, optionally within 1 degree, optionally within 0.1 degrees of orthogonal to the first direction. In an embodiment, this is achieved by arranging for the aperture 130B to exclusively pass radiation that will be orientated at the substrate W such that the component of the wavevector of the radiation in the plane of the substrate W is aligned within 10 degrees, optionally within 5 degrees, optionally within 2 degrees, optionally within 1 degree, optionally within 0.1 degrees of orthogonal to the first direction. If the target structure is oriented so that the first direction is horizontal in the plane of the page relative to the orientation of the aperture 130B of FIG. 29, the alignment with the orthogonal to the first direction can be achieved using aperture 130B. Thus, the target structure can be illuminated parallel to the grating lines of a target structure with s-polarized radiation by using aperture 130B in combination with H polarized radiation and with p-polarized radiation by using aperture 130B in combination with V polarized radiation.

Figure 30:
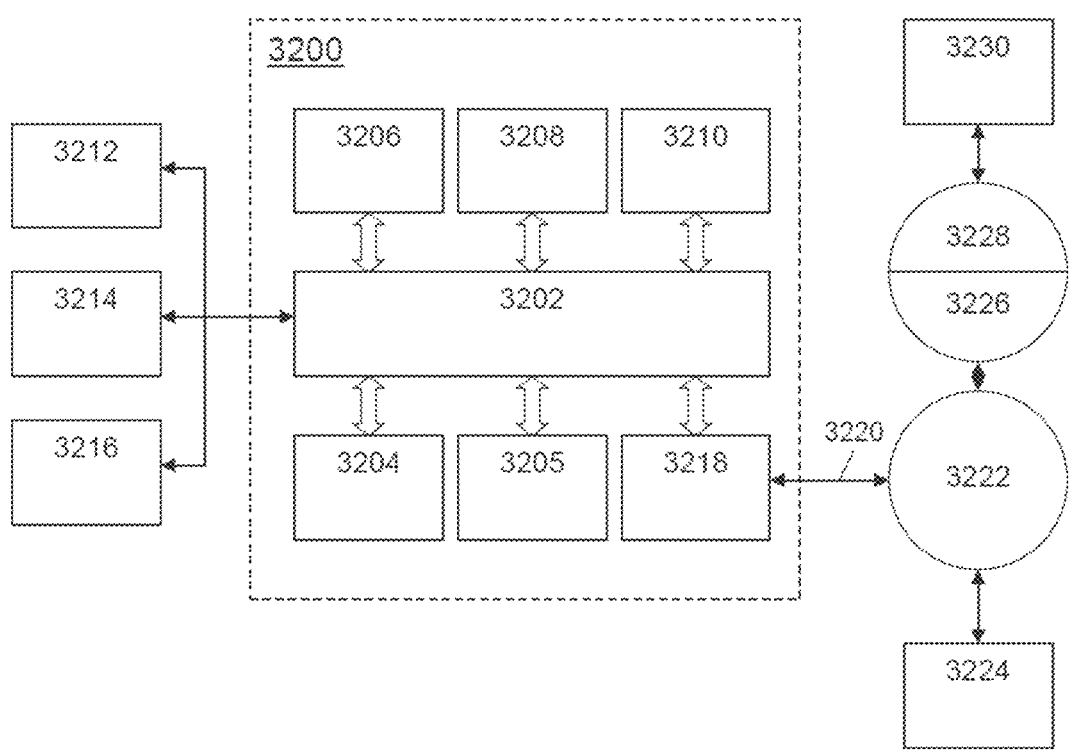
FIG. 30 schematically depicts a computer system which may implement embodiments of this disclosure.

Referring to FIG. 30, a computer system 3200 is shown. The computer system 3200 includes a bus 3202 or other communication mechanism for communicating information, and a processor 3204 (or multiple processors 3204 and 3205) coupled with bus 3202 for processing information. Computer system 3200 also includes a main memory 3206, such as a random access memory (RAM) or other dynamic storage device, coupled to bus 3202 for storing information and instructions to be executed by processor 3204. Main memory 3206 also may be used for storing temporary variables or other intermediate information during execution of instructions to be executed by processor 3204. Computer system 3200 further includes a read only memory (ROM) 3208 or other static storage device coupled to bus 3202 for storing static information and instructions for processor 3204. A storage device 3210, such as a magnetic disk or optical disk, is provided and coupled to bus 3202 for storing information and instructions.

Computer system 3200 may be coupled via bus 3202 to a display 3212, such as a cathode ray tube (CRT) or flat panel or touch panel display for displaying information to a computer user. An input device 3214, including alphanumeric and other keys, is coupled to bus 3202 for communicating information and command selections to processor 3204. Another type of user input device is cursor control 3216, such as a mouse, a trackball, or cursor direction keys for communicating direction information and command selections to processor 3204 and for controlling cursor movement on display 3212. This input device typically has two degrees of freedom in two axes, a first axis (e.g., x) and a second axis (e.g., y), that allows the device to specify positions in a plane. A touch panel (screen) display may also be used as an input device.

The computer system 3200 may be suitable to function as a processing unit herein in response to processor 3204 executing one or more sequences of one or more instructions contained in main memory 3206. Such instructions may be read into main memory 3206 from another computer-readable medium, such as storage device 3210. Execution of the sequences of instructions contained in main memory 3206 causes processor 3204 to perform a process described herein. One or more processors in a multi-processing arrangement may also be employed to execute the sequences of instructions contained in main memory 3206. In alternative embodiments, hard-wired circuitry may be used in place of or in combination with software instructions. Thus, embodiments are not limited to any specific combination of hardware circuitry and software.

The term "computer-readable medium" as used herein refers to any medium that participates in providing instructions to processor 3204 for execution. Such a medium may take many forms, including but not limited to, non-volatile media, volatile media, and transmission media. Non-volatile media include, for example, optical or magnetic disks, such as storage device 3210. Volatile media include dynamic memory, such as main memory 3206. Transmission media include coaxial cables, copper wire and fiber optics, including the wires that comprise bus 3202. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 3204 for execution. For example, the instructions may initially be borne on a magnetic disk of a remote computer. The remote computer can load the instructions into its dynamic memory and send the instructions over a telephone line using a modem. A modem local to computer system 3200 can receive the data on the telephone line and use an infrared transmitter to convert the data to an infrared signal. An infrared detector coupled to bus 3202 can receive the data carried in the infrared signal and place the data on bus 3202. Bus 3202 carries the data to main memory 3206, from which processor 3204 retrieves and executes the instructions. The instructions received by main memory 3206 may optionally be stored on storage device 3210 either before or after execution by processor 3204.

Computer system 3200 may also include a communication interface 3218 coupled to bus 3202. Communication interface 3218 provides a two-way data communication coupling to a network link 3220 that is connected to a local network 3222. For example, communication interface 3218 may be an integrated services digital network (ISDN) card or a modem to provide a data communication connection to a corresponding type of telephone line. As another example, communication interface 3218 may be a local area network (LAN) card to provide a data communication connection to a compatible LAN. Wireless links may also be implemented. In any such implementation, communication interface 3218 sends and receives electrical, electromagnetic or optical signals that carry digital data streams representing various types of information.

Network link 3220 typically provides data communication through one or more networks to other data devices. For example, network link 3220 may provide a connection through local network 3222 to a host computer 3224 or to data equipment operated by an Internet Service Provider (ISP) 3226. ISP 3226 in turn provides data communication services through the worldwide packet data communication network, now commonly referred to as the "Internet" 3228. Local network 3222 and Internet 3228 both use electrical, electromagnetic or optical signals that carry digital data streams. The signals through the various networks and the signals on network link 3220 and through communication interface 3218, which carry the digital data to and from computer system 3200, are exemplary forms of carrier waves transporting the information.

Computer system 3200 can send messages and receive data, including program code, through the network(s), network link 3220, and communication interface 3218. In the Internet example, a server 3230 might transmit a requested code for an application program through Internet 3228, ISP 3226, local network 3222 and communication interface 3218. In accordance with one or more embodiments, one such downloaded application provides for a method as disclosed herein, for example. The received code may be executed by processor 3204 as it is received, and/or stored in storage device 3210, or other non-volatile storage for later execution. In this manner, computer system 3200 may obtain application code in the form of a carrier wave.

An embodiment of the disclosure may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

Any controllers described herein may each or in combination be operable when the one or more computer programs are read by one or more computer processors located within at least one component of the lithographic apparatus. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers may include data storage medium for storing such computer programs, and/or hardware to receive such medium. So the controller(s) may operate according the machine readable instructions of one or more computer programs.

Although specific reference may be made in this text to the use of a metrology apparatus in the manufacture of ICs, it should be understood that the metrology apparatus and processes described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or one or more various other tools. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the disclosure in the context of optical lithography, it will be appreciated that the disclosure may be used in other applications, for example nanoimprint lithography, and where the context allows, is not limited to optical lithography. In the case of nanoimprint lithography, the patterning device is an imprint template or mold.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

References herein to crossing or passing a threshold may include something having a value lower than a specific value or lower than or equal to a specific value, something having a value higher than a specific value or higher than or equal to a specific value, something being ranked higher or lower than something else (through e.g., sorting) based on, e.g., a parameter, etc.

References herein to correcting or corrections of an error include eliminating the error or reducing the error to within a tolerance range.

The term "optimizing" and "optimization" as used herein refers to or means adjusting a lithographic apparatus, a patterning process, etc. such that results and/or processes of lithography or patterning processing have more a desirable characteristic, such as higher accuracy of projection of a design layout on a substrate, a larger process window, etc. Thus, the term "optimizing" and "optimization" as used herein refers to or means a process that identifies one or more values for one or more variables that provide an improvement, e.g. a local optimum, in at least one relevant metric, compared to an initial set of one or more values for those one or more variables. "Optimum" and other related terms should be construed accordingly. In an embodiment, optimization steps can be applied iteratively to provide further improvements in one or more metrics.

In an optimization process of a system, a figure of merit of the system or process can be represented as a cost function. The optimization process boils down to a process of finding a set of parameters (design variables) of the system or process that optimizes (e.g., minimizes or maximizes) the cost function. The cost function can have any suitable form depending on the goal of the optimization. For example, the cost function can be weighted root mean square (RMS) of deviations of certain characteristics (evaluation points) of the system or process with respect to the intended values (e.g., ideal values) of these characteristics, the cost function can also be the maximum of these deviations (i.e., worst deviation). The term "evaluation points" herein should be interpreted broadly to include any characteristics of the system or process. The design variables of the system can be confined to finite ranges and/or be interdependent due to practicalities of implementations of the system or process. In the case of a lithographic apparatus or patterning process, the constraints are often associated with physical properties and characteristics of the hardware such as tunable ranges, and/or patterning device manufacturability design rules, and the evaluation points can include physical points on a resist image on a substrate, as well as non-physical characteristics such as dose and focus.

While specific embodiments of the disclosure have been described above, it will be appreciated that the disclosure may be practiced otherwise than as described. For example, the disclosure may take the form of a computer program containing one or more sequences of machine-readable instructions describing a method as disclosed above, or a data storage medium (e.g. semiconductor memory, magnetic or optical disk) having such a computer program stored therein.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, third party content delivery networks may host some or all of the information conveyed over networks, in which case, to the extent information (e.g., content) is said to be supplied or otherwise provided, the information may be provided by sending instructions to retrieve that information from a content delivery network.

Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims.

Modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, certain features may be utilized independently, and embodiments or features of embodiments may be combined, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

Further embodiments according to the present invention are further described in below numbered clauses:

1. A metrology apparatus for measuring a structure formed on a substrate, comprising:

an optical system configured to focus radiation onto the structure and direct radiation after reflection from the structure onto a detection system; and a beam processing device configured to selectively extract a plurality of different components of the radiation beam after reflection from the structure, and to direct each of the extracted components to the detection system such that each component can be detected independently of each other component, wherein:

the selective extraction comprises, for each component:

1) selecting radiation from one of a plurality of predetermined regions in a downstream pupil plane of the optical system downstream from the structure, the selected predetermined region being different for each of at least a subset of the components; and 2) selecting radiation from one of two predetermined orthogonal polarization states, the predetermined orthogonal polarization states being oriented differently as a pair for each of at least a subset of the components comprising radiation selected from different predetermined regions in the downstream pupil plane.

2. The apparatus of clause 1, further comprising a polarization system configured to polarize the radiation focused onto the structure.

3. The apparatus of clause 2, wherein the polarization system is configured to apply a set of polarizations to a plurality of predetermined regions in an upstream pupil plane of the optical system upstream from the structure, the set of polarizations comprising different polarizations for at least a subset of the plurality of predetermined regions.

4. The apparatus of clause 3, wherein the different polarizations comprise linear polarizations that are oriented in different directions.

5. The apparatus of clause 3 or 4, wherein the set of polarizations are oriented substantially radially in the upstream pupil plane.

6. The apparatus of clause 3 or 4, wherein the set of polarizations are oriented substantially circumferentially in the upstream pupil plane.

7. The apparatus of any of clauses 3-6, wherein the polarization system is configured so that two different sets of polarizations can be applied selectively at different times.

8. The apparatus of clause 7, wherein the two different set of polarizations comprise:
a first set oriented substantially radially in the upstream pupil plane; and
a second set orientated substantially circumferentially in the upstream pupil plane.

9. The apparatus of any preceding clause, wherein the predetermined orthogonal polarization states for each of at least a subset of the plurality of predetermined regions of the downstream pupil plane comprise a substantially radially oriented polarization state and a substantially circumferentially oriented polarization state.

10. The apparatus of any preceding clause, wherein the predetermined orthogonal polarization states for each of at least a subset of the plurality of predetermined regions of the downstream pupil plane comprise a polarization state oriented at a common oblique angle to the radial direction.

11. The apparatus of any preceding clause, wherein:
the beam processing device is switchable between a first state and a second state;
the first state is such that, for each of at least a subset of the plurality of predetermined regions of the downstream pupil plane, the predetermined orthogonal polarization states comprise a substantially radially oriented polarization state and a substantially circumferentially oriented polarization state; and
the second state is such that, for each of the at least a subset of the plurality of predetermined regions of the downstream pupil plane, the predetermined orthogonal polarization states comprise a polarization state oriented at a common oblique angle to the radial direction.

12. The apparatus of clause 10 or 11, wherein the common oblique angle is substantially 45 degrees.

13. The apparatus of any preceding clause, wherein the beam processing device further comprises a plurality of retarders, each retarder overlapping, when viewed along a direction of incidence of radiation onto the retarder, with one of the predetermined regions in the downstream pupil plane and having axes aligned at a common angle with respect to the predetermined orthogonal polarization states corresponding to the predetermined region with which the retarder overlaps.

14. The apparatus of clause 13, wherein the common angle is substantially 45 degrees.

15. The apparatus of clause 13 or 14, wherein the retarder comprises a quarter wave plate.

16. The apparatus of any preceding clause, configured to use the detected components to obtain information about one or more of the following reflection intensities for each of a plurality of the predetermined regions in the downstream pupil plane of the optical system:

$|R_{pp}|^2$, where $R_{pp}$ represents a reflectivity for a p-polarized component of the reflected radiation beam when the corresponding radiation incident on the structure is p-polarized;

$|R_{ss}|^2$, where $R_{ss}$ represents a reflectivity for an s-polarized component of the reflected radiation beam when the corresponding radiation incident on the structure is s-polarized;

$|R_{sp}|^2$, where $R_{sp}$ represents a reflectivity for an s-polarized component of the reflected radiation beam when the corresponding radiation incident on the structure is p-polarized;

$|R_{ps}|^2$, where $R_{ps}$ represents a reflectivity for a p-polarized component of the reflected radiation beam when the corresponding radiation incident on the structure is s-polarized, where p-polarized radiation is radiation that is polarized in the plane of incidence of the radiation onto the structure and s-polarized radiation is radiation that is polarized orthogonally to the plane of incidence of the radiation onto the structure, the plane of incidence of the radiation onto the structure being the plane that contains the normal vector to the plane of the structure and the wavevector of the incident radiation.

17. A method of measuring a structure formed on a substrate, comprising:
focusing radiation onto the structure and directing radiation after reflection from the structure onto a detection system; and
selectively extracting a plurality of different components of the radiation beam after reflection from the structure, and detecting each of the extracted components independently of each other component using the detection system, wherein:
the selective extraction comprises, for each component:
1) selecting radiation from one of a plurality of predetermined regions in a downstream pupil plane of the optical system downstream from the structure, the selected predetermined region being different for each of at least a subset of the components; and
2) selecting radiation from one of two predetermined orthogonal polarization states, the predetermined orthogonal polarization states being oriented differently as a pair for each of at least a subset of the components comprising radiation selected from different predetermined regions in the downstream pupil plane.

18. The method of clause 17, wherein the radiation focused onto the structure is polarized.

19. The method of clause 18, wherein a set of polarizations are applied to a plurality of predetermined regions in an upstream pupil plane of the optical system upstream from the structure, the set of polarizations comprising different polarizations for at least a subset of the plurality of predetermined regions.

20. The method of clause 19, wherein the different polarizations comprise linear polarizations that are oriented in different directions.

21. The method of clause 19 or 20, wherein the set of polarizations are oriented substantially radially in the upstream pupil plane.

22. The method of clause 19 or 20, wherein the set of polarizations are oriented substantially circumferentially in the upstream pupil plane.

23. The method of any of clauses 19-22, wherein two different sets of polarizations are applied at different times.

24. The method of clause 23, wherein the two different sets of polarizations comprise:
a first set oriented substantially radially in the upstream pupil plane; and a second set orientated substantially circumferentially in the upstream pupil plane.

25. The method of any of clauses 17-24, wherein the predetermined orthogonal polarization states for each of at least a subset of the plurality of predetermined regions of the downstream pupil plane comprise a substantially radially oriented polarization state and a substantially circumferentially oriented polarization state.

26. The method of any of clauses 17-25, wherein the predetermined orthogonal polarization states for each of at least a subset of the plurality of predetermined regions of the downstream pupil plane comprise a polarization state oriented at a common oblique angle to the radial direction.

27. The method of clause 26, wherein the common oblique angle is substantially 45 degrees.

28. The method of any of clauses 17-27, further comprising using a plurality of retarders, each retarder overlapping, when viewed along a direction of incidence of radiation onto the retarder, with one of the predetermined regions in the downstream pupil plane and having axes aligned at a common angle with respect to the predetermined orthogonal polarization states corresponding to the predetermined region with which the retarder overlaps.

29. The method of clause 28, wherein the common angle is substantially 45 degrees.

30. The method of clause 28 or 29, wherein the retarder comprises a quarter wave plate.

31. The method of any of clauses 17-30, wherein the detected components are used to obtain information about one or more of the following reflection intensities for each of a plurality of the predetermined regions in the downstream pupil plane of the optical system:

$|R_{pp}|^2$, where $R_{pp}$ represents a reflectivity for a p-polarized component of the reflected radiation beam when the corresponding radiation incident on the structure is p-polarized;

$|R_{ss}|^2$, where $R_{ss}$ represents a reflectivity for an s-polarized component of the reflected radiation beam when the corresponding radiation incident on the structure is s-polarized;

$|R_{sp}|^2$, where $R_{sp}$ represents a reflectivity for an s-polarized component of the reflected radiation beam when the corresponding radiation incident on the structure is p-polarized;

$|R_{ps}|^2$, where $R_{ps}$ represents a reflectivity for a p-polarized component of the reflected radiation beam when the corresponding radiation incident on the structure is s-polarized, where p-polarized radiation is radiation that is polarized in the plane of incidence of the radiation onto the structure and s-polarized radiation is radiation that is polarized orthogonally to the plane of incidence of the radiation onto the structure, the plane of incidence of the radiation onto the structure being the plane that contains the normal vector to the plane of the structure and the wavevector of the incident radiation.

32. The method of clause 31, wherein a difference between $|R_{sp}|^2$ and $|R_{ps}|^2$ is used to determine a parameter of interest.

33. The method of clause 32, wherein the parameter of interest comprises an asymmetry in the structure.

34. The method of clause 32 or 33, wherein the parameter of interest comprises overlay error between different layers in the structure.

35. The method of any of clauses 17-32, further comprising using the detected components to determine an asymmetry in the structure.

36. The method of any of clauses 17-32, further comprising using the detected components to determine an overlay error between different layers in the structure.

37. The method of any of clauses 17-36, wherein the detected components are of primarily zeroth order radiation.

38. The method of any of clauses 17-37, wherein the structure comprises a device structure or a non-device structure within a substrate die comprising a device structure.

39. A device manufacturing method, comprising:
using a patterning process to form a structure on a substrate;
focusing radiation onto the structure and directing radiation after reflection from the structure onto a detection system; and
selectively extracting a plurality of different components of the radiation beam after reflection from the structure, and detecting each of the extracted components independently of each other component using the detection system, wherein:
the selective extraction comprises, for each component:
1) selecting radiation from one of a plurality of predetermined regions in a downstream pupil plane of the optical system downstream from the structure, the selected predetermined region being different for each of at least a subset of the components; and
2) selecting radiation from one of two predetermined orthogonal polarization states, the predetermined orthogonal polarization states being oriented differently as a pair for each of at least a subset of the components comprising radiation selected from different predetermined regions in the downstream pupil plane.

40. A method of measuring a structure formed on a substrate, comprising:
performing one or more measurement processes, each measurement process comprising illuminating the structure with radiation and detecting radiation redirected by the structure, wherein:
in each of one or more of the measurement processes, the radiation illuminating the structure consists of at least 90% p-polarized radiation or consists of at least 90% s-polarized radiation, wherein p-polarized radiation is radiation that is polarized in the plane of incidence of the radiation onto the structure and s-polarized radiation is radiation that is polarized orthogonally to the plane of incidence of the radiation onto the structure, the plane of incidence of the radiation onto the structure being the plane that contains the normal vector to the plane of the structure and the wavevector of the incident radiation; and
either or both of the at least 90% p-polarized radiation and the at least 90% s-polarized radiation is produced by applying a uniform polarization to radiation upstream from the structure and removing a portion of the radiation in a pupil plane upstream from the structure using an aperture.

41. The method of clause 40, comprises detecting an image in an image plane.

42. The method of clause 40 or 41, wherein the structure is a periodic structure having a periodicity in a first direction.

43. The method of clause 42, wherein, in each of one or more of the measurement processes, at least 90% of the radiation illuminating the structure is orientated so that the component of the wavevector of the radiation in the plane of the substrate is aligned within 10 degrees of the first direction.

44. The method of clause 43, wherein the aperture exclusively passes radiation that will be orientated at the substrate such that the component of the wavevector of the radiation in the plane of the substrate is aligned within 10 degrees of the first direction.

45. The method of clause 42, wherein, in each of one or more of the measurement processes, at least 90% of the radiation illuminating the structure is orientated so that the component of the wavevector of the radiation in the plane of the substrate is aligned within 10 degrees of orthogonal to the first direction.

46. The method of clause 45, wherein the aperture exclusively passes radiation that will be orientated at the substrate such that the component of the wavevector of the radiation in the plane of the substrate is aligned within 10 degrees of orthogonal to the first direction.

47. A metrology apparatus for measuring a structure formed on a substrate, comprising:
an optical system configured to perform one or more measurement processes, each measurement process comprising illuminating the structure with radiation and detecting radiation redirected by the structure with a detection system, wherein:
the apparatus is configured such that, in each of one or more of the measurement processes:
the radiation illuminating the structure consists of at least 90% p-polarized radiation or consists of at least 90% s-polarized radiation, wherein p-polarized radiation is radiation that is polarized in the plane of incidence of the radiation onto the structure and s-polarized radiation is radiation that is polarized orthogonally to the plane of incidence of the radiation onto the structure, the plane of incidence of the radiation onto the structure being the plane that contains the normal vector to the plane of the structure and the wavevector of the incident radiation; and
the optical system comprises a polarizer and an aperture, and is configured such that either or both of the at least 90% p-polarized radiation and the at least 90% s-polarized radiation is produced by using the polarizer to apply a uniform polarization to radiation upstream from the structure and using the aperture to remove a portion of the radiation in a pupil plane upstream from the structure.

48. The apparatus of clause 47, wherein the detection system is configured to detect an image in an image plane.

49. The apparatus of clause 47 or 48, wherein the structure is a periodic structure having a periodicity in a first direction.

50. The apparatus of clause 49, wherein the optical system is configured such that, in each of one or more of the measurement processes, at least 90% of the radiation illuminating the structure is orientated so that the component of the wavevector of the radiation in the plane of the substrate is aligned within 10 degrees of the first direction.

51. The apparatus of clause 50, wherein the aperture is configured to exclusively pass radiation that will be orientated at the substrate such that the component of the wavevector of the radiation in the plane of the substrate is aligned within 10 degrees of the first direction.

52. The apparatus of clause 49, wherein the optical system is configured such that, in each of one or more of the measurement processes, at least 90/o of the radiation illuminating the structure is orientated so that the component of the wavevector of the radiation in the plane of the substrate is aligned within 10 degrees of orthogonal to the first direction.

53. The apparatus of clause 52, wherein the aperture is configured to exclusively pass radiation that will be orientated at the substrate such that the component of the wavevector of the radiation in the plane of the substrate is aligned within 10 degrees of orthogonal to the first direction.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an" element or "a" element includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every.

To the extent certain U.S. patents, U.S. patent applications, or other materials (e.g., articles) have been incorporated by reference, the text of such U.S. patents, U.S. patent applications, and other materials is only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference herein.

The descriptions above are intended to be illustrative, not limiting. Thus, it will be apparent to one skilled in the art that modifications may be made to the disclosure as described without departing from the scope of the claims set out below.

The invention claimed is:
1. A metrology apparatus for measuring a structure formed on a substrate, comprising:
an optical system configured to focus radiation onto the structure and direct radiation after reflection from the structure onto a detection system; and a beam processing device configured to selectively extract a plurality of different components of the radiation beam after reflection from the structure, and to direct each of the extracted components to the detection system such that each component can be detected independently of each other component, wherein:

the selective extraction comprises, for each component:

selecting radiation from one of a plurality of predetermined regions in a downstream pupil plane of the optical system downstream from the structure, the selected predetermined region being different for each of at least a subset of the components; and selecting radiation from one of two predetermined orthogonal polarization states, the predetermined orthogonal polarization states being oriented as a pair defined by a sub-region of the beam processing device corresponding to the one of the plurality of predetermined regions, and being oriented differently from other predetermined orthogonal polarization states defined by other sub-regions of the beam processing device corresponding to different predetermined regions at different azimuthal positions in the downstream pupil plane.

2. The apparatus of claim 1, further comprising a polarization system configured to polarize the radiation focused onto the structure.

3. The apparatus of claim 2, wherein the polarization system is configured to apply a set of polarizations to a plurality of predetermined regions in an upstream pupil plane of the optical system upstream from the structure, the set of polarizations comprising different polarizations for at least a subset of the plurality of predetermined regions.

4. The apparatus of claim 3, wherein the different polarizations comprise linear polarizations that are oriented in different directions.

5. The apparatus of claim 3, wherein the set of polarizations are oriented substantially radially in the upstream pupil plane.

6. The apparatus of claim 3, wherein the set of polarizations are oriented substantially circumferentially in the upstream pupil plane.

7. The apparatus of any of claim 3, wherein the polarization system is configured so that two different sets of polarizations can be applied selectively at different times.

8. The apparatus of claim 7, wherein the two different sets of polarizations comprise:

a first set oriented substantially radially in the upstream pupil plane; and a second set orientated substantially circumferentially in the upstream pupil plane.

9. The apparatus of claim 1, wherein the predetermined orthogonal polarization states for each of at least a subset of the plurality of predetermined regions of the downstream pupil plane comprise a substantially radially oriented polarization state and a substantially circumferentially oriented polarization state.

10. The apparatus of claim 1, wherein the predetermined orthogonal polarization states for each of at least a subset of the plurality of predetermined regions of the downstream pupil plane comprise a polarization state oriented at a common oblique angle to the radial direction.

11. The apparatus of claim 1, wherein:

the beam processing device is switchable between a first state and a second state;

the first state is such that, for each of at least a subset of the plurality of predetermined regions of the downstream pupil plane, the predetermined orthogonal polarization states comprise a substantially radially oriented polarization state and a substantially circumferentially oriented polarization state; and the second state is such that, for each of the at least a subset of the plurality of predetermined regions of the downstream pupil plane, the predetermined orthogonal polarization states comprise a polarization state oriented at a common oblique angle to the radial direction.

12. The apparatus of claim 10, wherein the common oblique angle is substantially 45 degrees.

13. The apparatus of claim 1, wherein the beam processing device further comprises a plurality of retarders, each retarder overlapping, when viewed along a direction of incidence of radiation onto the retarder, with one of the predetermined regions in the downstream pupil plane and having axes aligned at a common angle with respect to the predetermined orthogonal polarization states corresponding to the predetermined region with which the retarder overlaps.

14. The apparatus of claim 13, wherein the common angle is substantially 45 degrees.

15. The apparatus of claim 13, wherein the retarder comprises a quarter wave plate.

* * * * *